US010435701B2

(12) United States Patent
Crawford et al.

(10) Patent No.: US 10,435,701 B2
(45) Date of Patent: Oct. 8, 2019

(54) METHODS AND COMPOSITIONS FOR PLANT PEST CONTROL

(71) Applicant: Monsanto Technology LLC, St. Louis, MO (US)

(72) Inventors: Michael J. Crawford, St. Louis, MO (US); Michelle L. Gasper, St. Charles, MO (US); Xiangqian Li, Chesterfield, MO (US); Barry J. Shortt, New Melle, MO (US); Deryck Jeremy Williams, University City, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/682,205

(22) Filed: Aug. 21, 2017

(65) Prior Publication Data

US 2018/0037899 A1 Feb. 8, 2018

Related U.S. Application Data

(63) Continuation of application No. 14/209,108, filed on Mar. 13, 2014, now abandoned.

(60) Provisional application No. 61/783,260, filed on Mar. 14, 2013.

(51) Int. Cl.
*C12N 15/82* (2006.01)

(52) U.S. Cl.
CPC ..... *C12N 15/8218* (2013.01); *C12N 15/8285* (2013.01); *C12N 15/8282* (2013.01); *Y02A 40/164* (2018.01)

(58) Field of Classification Search
None
See application file for complete search history.

(56) References Cited

U.S. PATENT DOCUMENTS 3,687,808 A 8/1972 De et al.
3,850,752 A 11/1974 Schuurs et al.
3,935,074 A 1/1976 Rubenstein et al.
4,023,525 A 5/1977 Weber
4,079,696 A 3/1978 Weber
4,476,301 A 10/1984 Imbach et al.
4,535,060 A 8/1985 Comai
4,581,847 A 4/1986 Hibberd et al.
4,761,373 A 8/1988 Anderson et al.
4,769,061 A 9/1988 Comai
4,810,648 A 3/1989 Stalker
4,940,835 A 7/1990 Shah et al.
4,971,908 A 11/1990 Kishore et al.
5,004,863 A 4/1991 Umbeck
5,013,659 A 5/1991 Bedbrook et al.
5,015,580 A 5/1991 Christou et al.
5,023,243 A 6/1991 Tullis
5,034,506 A 7/1991 Summerton et al.
5,094,945 A 3/1992 Comai
5,141,870 A 8/1992 Bedbrook et al.
5,145,783 A 9/1992 Kishore et al.
5,159,135 A 10/1992 Umbeck
5,166,315 A 11/1992 Summerton et al.
5,177,196 A 1/1993 Meyer, Jr. et al.
5,185,444 A 2/1993 Summerton et al.
5,188,642 A 2/1993 Shah et al.
5,188,897 A 2/1993 Suhadolnik et al.
5,192,659 A 3/1993 Simons
5,214,134 A 5/1993 Weis et al.
5,216,141 A 6/1993 Benner
5,235,033 A 8/1993 Summerton et al.
5,264,562 A 11/1993 Matteucci
5,264,564 A 11/1993 Matteucci
5,304,732 A 4/1994 Anderson et al.
5,310,667 A 5/1994 Eichholtz et al.
5,312,910 A 5/1994 Kishore et al.
5,331,107 A 7/1994 Anderson et al.
5,378,824 A 1/1995 Bedbrook et al.
5,399,676 A 3/1995 Froehler
5,405,938 A 4/1995 Summerton et al.
5,405,939 A 4/1995 Suhadolnik et al.
5,416,011 A 5/1995 Hinchee et al.
5,453,496 A 9/1995 Caruthers et al.
5,455,233 A 10/1995 Spielvogel et al.
5,463,174 A 10/1995 Moloney et al.
5,463,175 A 10/1995 Barry et al.
5,470,967 A 11/1995 Huie et al.
5,476,925 A 12/1995 Letsinger et al.
(Continued)

FOREIGN PATENT DOCUMENTS

CN 101914540 A 12/2010
EP 1416049 A1 5/2004
(Continued)

OTHER PUBLICATIONS

Xu et al (Computational Estimation and Experimental Verification of Off-Target Silencing during Posttranscriptional Gene Silencing in Plants. Plant physiology. 142:429-440, 2006).*
Schmutz et al (Genome sequence of the palaeopolyploid Soybean. Nature. 463: 178-184, 2010).*
Office Action dated Feb. 17, 2014, in Mexican Patent Application No. MX/a/2012/010479.
Office Action for UA Application No. 201211548 dated Jul. 23, 2015.
Office Action for U.S. Appl. No. 13/612,985 dated Nov. 10, 2015.
Office Action dated Jan. 6, 2015, in Japanese Patent Application No. 2012-557165.
Office Action dated Nov. 19, 2014, in Eurasian Patent Application No. 201201264/28.
(Continued)

*Primary Examiner* — Medina A Ibrahim
*Assistant Examiner* — Wayne Zhong
(74) *Attorney, Agent, or Firm* — Thompson Coburn LLP; William A. Holtz; Amanda J. Carmany-Rampey

(57) ABSTRACT

Provided are methods and compositions to improve fungal disease resistance and/or nematode resistance in various crop plants. Also provided are combinations of compositions and methods to improve fungal disease resistance and/or nematode resistance in various crop plants.

17 Claims, 3 Drawing Sheets

Specification includes a Sequence Listing.

(56) References Cited

U.S. PATENT DOCUMENTS

| | | | |
|---|---|---|---|
| 5,489,520 | A | 2/1996 | Adams et al. |
| 5,489,677 | A | 2/1996 | Sanghvi et al. |
| 5,491,288 | A | 2/1996 | Chaubet et al. |
| 5,506,559 | A | 4/1996 | Yamaguchi |
| 5,510,471 | A | 4/1996 | Lebrun et al. |
| 5,519,126 | A | 5/1996 | Hecht |
| 5,536,821 | A | 7/1996 | Agrawal et al. |
| 5,538,880 | A | 7/1996 | Lundquist et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,550,318 | A | 8/1996 | Adams et al. |
| 5,561,225 | A | 10/1996 | Maddry et al. |
| 5,561,236 | A | 10/1996 | Leemans et al. |
| 5,563,253 | A | 10/1996 | Agrawal et al. |
| 5,569,834 | A | 10/1996 | Hinchee et al. |
| 5,571,799 | A | 11/1996 | Tkachuk et al. |
| 5,587,361 | A | 12/1996 | Cook et al. |
| 5,591,616 | A | 1/1997 | Hiei et al. |
| 5,593,874 | A | 1/1997 | Brown et al. |
| 5,596,086 | A | 1/1997 | Matteucci et al. |
| 5,602,240 | A | 2/1997 | De Mesmaeker et al. |
| 5,605,011 | A | 2/1997 | Bedbrook et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,061 | A | 5/1997 | Barry et al. |
| 5,633,360 | A | 5/1997 | Bischofberger et al. |
| 5,633,435 | A | 5/1997 | Barry et al. |
| 5,633,448 | A | 5/1997 | Lebrun et al. |
| 5,639,024 | A | 6/1997 | Mueller et al. |
| 5,646,024 | A | 7/1997 | Leemans et al. |
| 5,648,477 | A | 7/1997 | Leemans et al. |
| 5,663,312 | A | 9/1997 | Chaturvedula |
| 5,677,437 | A | 10/1997 | Teng et al. |
| 5,677,439 | A | 10/1997 | Weis et al. |
| 5,719,046 | A | 2/1998 | Guerineau et al. |
| 5,721,138 | A | 2/1998 | Lawn |
| 5,731,180 | A | 3/1998 | Dietrich |
| 5,767,361 | A | 6/1998 | Dietrich |
| 5,767,373 | A | 6/1998 | Ward et al. |
| 5,780,708 | A | 7/1998 | Lundquist et al. |
| 5,804,425 | A | 9/1998 | Barry et al. |
| 5,824,877 | A | 10/1998 | Hinchee et al. |
| 5,866,775 | A | 2/1999 | Eichholtz et al. |
| 5,874,265 | A | 2/1999 | Adams et al. |
| 5,876,739 | A | 3/1999 | Turnblad et al. |
| 5,879,903 | A | 3/1999 | Strauch et al. |
| 5,891,246 | A | 4/1999 | Lund |
| 5,914,451 | A | 6/1999 | Martinell et al. |
| 5,919,675 | A | 7/1999 | Adams et al. |
| 5,922,602 | A | 7/1999 | Kumagai et al. |
| 5,928,937 | A | 7/1999 | Kakefuda et al. |
| 5,939,602 | A | 8/1999 | Volrath et al. |
| 5,969,213 | A | 10/1999 | Adams et al. |
| 5,981,840 | A | 11/1999 | Zhao et al. |
| 5,985,793 | A | 11/1999 | Sandbrink et al. |
| RE36,449 | E | 12/1999 | Lebrun et al. |
| 6,040,497 | A | 3/2000 | Spencer et al. |
| 6,056,938 | A | 5/2000 | Unger et al. |
| 6,069,115 | A | 5/2000 | Pallett et al. |
| 6,084,155 | A | 7/2000 | Volrath et al. |
| 6,118,047 | A | 9/2000 | Anderson et al. |
| 6,121,513 | A | 9/2000 | Zhang et al. |
| 6,130,366 | A | 10/2000 | Herrera-Estrella et al. |
| 6,153,812 | A | 11/2000 | Fry et al. |
| 6,160,208 | A | 12/2000 | Lundquist et al. |
| 6,177,616 | B1 | 1/2001 | Bartsch et al. |
| 6,225,105 | B1 | 5/2001 | Sathasivan et al. |
| 6,225,114 | B1 | 5/2001 | Eichholtz et al. |
| 6,245,968 | B1 | 6/2001 | Boudec et al. |
| 6,248,876 | B1 | 6/2001 | Barry et al. |
| RE37,287 | E | 7/2001 | Lebrun et al. |

| | | | |
|---|---|---|---|
| 6,268,549 | B1 | 7/2001 | Sailland et al. |
| 6,271,359 | B1 | 8/2001 | Norris et al. |
| 6,282,837 | B1 | 9/2001 | Ward et al. |
| 6,288,306 | B1 | 9/2001 | Ward et al. |
| 6,288,312 | B1 | 9/2001 | Christou et al. |
| 6,294,714 | B1 | 9/2001 | Matsunaga et al. |
| 6,326,193 | B1 | 12/2001 | Liu et al. |
| 6,329,571 | B1 | 12/2001 | Niel |
| 6,348,185 | B1 | 2/2002 | Piwnica-Worms |
| 6,365,807 | B1 | 4/2002 | Christou et al. |
| 6,384,301 | B1 | 5/2002 | Martinell et al. |
| 6,385,902 | B1 | 5/2002 | Schipper et al. |
| 6,399,861 | B1 | 6/2002 | Anderson et al. |
| 6,403,865 | B1 | 6/2002 | Koziel et al. |
| 6,414,222 | B1 | 7/2002 | Gengenbach et al. |
| 6,421,956 | B1 | 7/2002 | Boukens et al. |
| 6,453,609 | B1 | 9/2002 | Soli et al. |
| 6,582,516 | B1 | 6/2003 | Carlson |
| 6,635,805 | B1 | 10/2003 | Baulcombe et al. |
| 6,644,341 | B1 | 11/2003 | Chemo et al. |
| 6,768,044 | B1 | 7/2004 | Boudec et al. |
| 6,791,007 | B1 | 9/2004 | Schulze-Lefert et al. |
| 6,800,748 | B2 | 10/2004 | Holzberg et al. |
| 6,870,075 | B1 | 3/2005 | Beetham et al. |
| 6,992,237 | B1 | 1/2006 | Habben et al. |
| 7,022,896 | B1 | 4/2006 | Weeks et al. |
| 7,026,528 | B2 | 4/2006 | Cheng et al. |
| RE39,247 | E | 8/2006 | Barry et al. |
| 7,105,724 | B2 | 9/2006 | Weeks et al. |
| 7,122,719 | B2 | 10/2006 | Hakimi et al. |
| 7,297,541 | B2 | 11/2007 | Moshiri et al. |
| 7,304,209 | B2 | 12/2007 | Zink et al. |
| 7,312,379 | B2 | 12/2007 | Andrews et al. |
| 7,323,310 | B2 | 1/2008 | Peters et al. |
| 7,371,927 | B2 | 5/2008 | Yao et al. |
| 7,405,347 | B2 | 7/2008 | Hammer et al. |
| 7,406,981 | B2 | 8/2008 | Remo et al. |
| 7,485,777 | B2 | 2/2009 | Nakajima et al. |
| 7,525,013 | B2 | 4/2009 | Hildebrand et al. |
| 7,622,301 | B2 | 11/2009 | Ren et al. |
| 7,671,254 | B2 | 3/2010 | Tranel et al. |
| 7,714,188 | B2 | 5/2010 | Castle et al. |
| 7,838,263 | B2 | 11/2010 | Dam et al. |
| 7,838,733 | B2 | 11/2010 | Wright et al. |
| 7,842,856 | B2 | 11/2010 | Tranel et al. |
| 7,884,262 | B2 | 2/2011 | Clemente et al. |
| 7,910,805 | B2 | 3/2011 | Duck |
| 7,935,869 | B2 | 5/2011 | Allett et al. |
| 7,943,819 | B2 | 5/2011 | Baum et al. |
| 7,973,218 | B2 | 7/2011 | Vlccutchen et al. |
| 8,143,480 | B2 | 3/2012 | Axtell et al. |
| 8,642,505 | B2 | 2/2014 | Kohn |
| 9,121,022 | B2 | 9/2015 | Sammons et al. |
| 9,422,557 | B2 | 8/2016 | Ader et al. |
| 9,840,715 | B1 | 12/2017 | Deikman et al. |
| 2001/0042257 | A1 | 11/2001 | Connor-Ward et al. |
| 2002/0114784 | A1 | 8/2002 | Li et al. |
| 2003/0150017 | A1 | 8/2003 | Mesa et al. |
| 2003/0167537 | A1 | 9/2003 | Jiang |
| 2003/0235916 | A1 | 12/2003 | Monahan et al. |
| 2004/0053289 | A1 | 3/2004 | Christian et al. |
| 2004/0055041 | A1 | 3/2004 | Labate et al. |
| 2004/0126845 | A1 | 7/2004 | Eenennaam et al. |
| 2004/0133944 | A1 | 7/2004 | Hake et al. |
| 2004/0147475 | A1 | 7/2004 | Li et al. |
| 2004/0177399 | A1 | 9/2004 | Hammer et al. |
| 2004/0244075 | A1 | 12/2004 | Cai et al. |
| 2005/0026290 | A1 | 2/2005 | Ciardi et al. |
| 2005/0239728 | A1 | 10/2005 | Pachuk et al. |
| 2006/0021087 | A1 | 1/2006 | Baum et al. |
| 2006/0064775 | A1 | 3/2006 | Frank et al. |
| 2006/0111241 | A1 | 5/2006 | Gerwick et al. |
| 2006/0130172 | A1 | 6/2006 | Whaley et al. |
| 2006/0135758 | A1 | 6/2006 | Wu |
| 2006/0200878 | A1 | 9/2006 | Lutfiyya et al. |
| 2006/0247197 | A1 | 11/2006 | Van De Craen et al. |
| 2006/0272049 | A1 | 11/2006 | Waterhouse et al. |
| 2006/0276339 | A1 | 12/2006 | Windsor et al. |
| 2007/0011775 | A1 | 1/2007 | Allen et al. |

(56) References Cited

U.S. PATENT DOCUMENTS

2007/0050863 A1 3/2007 Tranel et al.
2007/0124836 A1 5/2007 Baum et al.
2007/0199095 A1 8/2007 Allen et al.
2007/0250947 A1 10/2007 Boukharov et al.
2007/0259785 A1 11/2007 Heck et al.
2007/0281900 A1 12/2007 Cui et al.
2007/0300329 A1 12/2007 Allen et al.
2008/0022423 A1 1/2008 Roberts et al.
2008/0050342 A1 2/2008 Fire et al.
2008/0092256 A1 4/2008 Kohn
2008/0155716 A1 6/2008 Sonnewald et al.
2008/0214443 A1 9/2008 Baum et al.
2009/0011934 A1 1/2009 Zawierucha et al.
2009/0018016 A1 1/2009 Duck et al.
2009/0098614 A1 4/2009 Zamore et al.
2009/0137395 A1 5/2009 Chicoine et al.
2009/0165153 A1 6/2009 Wang et al.
2009/0165166 A1 6/2009 Feng et al.
2009/0188005 A1* 7/2009 Boukharov ........ C07K 14/4354 800/279
2009/0205079 A1 8/2009 Kumar et al.
2009/0293148 A1 11/2009 Ren et al.
2009/0307803 A1 12/2009 Baum et al.
2010/0005551 A1 1/2010 Roberts et al.
2010/0068172 A1 3/2010 Van De Craen
2010/0071088 A1 3/2010 Sela et al.
2010/0100988 A1 4/2010 Tranel et al.
2010/0122381 A1 5/2010 Buehler et al.
2010/0154083 A1 6/2010 Ross et al.
2010/0192254 A1 7/2010 Frank et al.
2010/0247578 A1 9/2010 Salaam
2010/0306875 A1 12/2010 Rikkerink et al.
2011/0035836 A1 2/2011 Eudes et al.
2011/0098180 A1 4/2011 Michel et al.
2011/0105327 A1 5/2011 Nelson
2011/0126310 A1 5/2011 Feng et al.
2011/0126311 A1 5/2011 Velcheva et al.
2011/0152346 A1 6/2011 Karleson et al.
2011/0152353 A1 6/2011 Koizumi et al.
2011/0160082 A1 6/2011 Woo et al.
2011/0166022 A1 7/2011 Israels et al.
2011/0166023 A1 7/2011 Nettleton-Hammond et al.
2011/0171176 A1 7/2011 Baas et al.
2011/0171287 A1 7/2011 Saarma et al.
2011/0177949 A1 7/2011 Krapp et al.
2011/0185444 A1 7/2011 Li et al.
2011/0185445 A1 7/2011 Bogner et al.
2011/0191897 A1 8/2011 Poree et al.
2011/0296555 A1 12/2011 Ivashuta et al.
2011/0296556 A1 12/2011 Sammons et al.
2012/0036594 A1 2/2012 Cardoza et al.
2012/0137387 A1 5/2012 Baum et al.
2012/0156784 A1 6/2012 Adams, Jr. et al.
2012/0159672 A1 6/2012 Alexandrov et al.
2012/0164205 A1 6/2012 Baum et al.
2012/0185967 A1 7/2012 Sela et al.
2013/0003213 A1 1/2013 Kabelac et al.
2013/0041004 A1 2/2013 Drager et al.
2013/0047297 A1 2/2013 Sammons et al.
2013/0067618 A1* 3/2013 Ader ........................ A01H 3/04 800/278
2013/0096073 A1 4/2013 Sidelman
2013/0097726 A1 4/2013 Ader et al.
2013/0212739 A1 8/2013 Giritch et al.
2013/0247247 A1 9/2013 Ader et al.
2013/0254940 A1 9/2013 Ader et al.
2013/0254941 A1 9/2013 Ader et al.
2013/0288895 A1 10/2013 Ader et al.
2013/0318657 A1 11/2013 Avniel et al.
2013/0318658 A1 11/2013 Ader et al.
2013/0326731 A1 12/2013 Ader et al.
2013/0333061 A1* 12/2013 Wu ...................... C07K 14/415 800/260
2014/0018241 A1 1/2014 Sammons et al.
2014/0057789 A1 2/2014 Sammons et al.
2014/0059714 A1* 2/2014 Matarasso ............ C07K 14/415 800/281
2014/0109258 A1 4/2014 Van De Craen et al.
2014/0215656 A1 7/2014 Crawford et al.
2014/0230090 A1 8/2014 Avniel et al.
2014/0274712 A1 9/2014 Finnessy et al.
2014/0283211 A1 9/2014 Crawford et al.
2014/0296503 A1 10/2014 Avniel et al.
2015/0247153 A1 9/2015 Fillatti et al.

FOREIGN PATENT DOCUMENTS

EP 2 530 159 A1 12/2012
JP 2006343473 A 12/2006
WO 1989/11789 A1 12/1989
WO 94/03607 A1 2/1994
WO 1996/005721 A1 2/1996
WO 1996/033270 A1 10/1996
WO 1996/038567 A2 12/1996
WO 1996/040964 A2 12/1996
WO 1999/024585 A1 5/1999
WO 99/32619 A1 7/1999
WO 1999/32619 A1 7/1999
WO 99/67367 A1 12/1999
WO 1999/61631 A1 12/1999
WO 00/32757 A2 6/2000
WO 2000/044914 A1 8/2000
WO 2001/007596 A1 2/2001
WO WO 2001007596 * 2/2001
WO 2002/14472 A2 2/2002
WO 2003/106636 A2 12/2003
WO 2004/005485 A2 1/2004
WO 2004/009761 A2 1/2004
WO 2004/022771 A2 3/2004
WO 2004/074443 A2 9/2004
WO 2005/003362 A2 1/2005
WO 2005/007860 A1 1/2005
WO 2005/107437 A2 11/2005
WO 2005/110068 A2 11/2005
WO 2006/074400 A2 7/2006
WO 2006/138638 A1 12/2006
WO 2007/007316 A1 1/2007
WO 2007/035650 A2 3/2007
WO 2007/039454 A1 4/2007
WO 2007/051462 A2 5/2007
WO 2007/070389 A2 6/2007
WO 2007/074405 A2 7/2007
WO 2007/080126 A2 7/2007
WO 2007/080127 A2 7/2007
WO 2008/007100 A2 1/2008
WO 2008/063203 A2 5/2008
WO 2008/148223 A1 12/2008
WO 2009/046384 A1 4/2009
WO 2009/116558 A1 9/2009
WO 2009/125401 A2 10/2009
WO 2010/078912 A1 7/2010
WO 2010/083179 A2 7/2010
WO 2010/104217 A1 9/2010
WO 2010/108611 A1 9/2010
WO 2010/112826 A2 10/2010
WO 2010/116122 A2 10/2010
WO 2010/119906 A1 10/2010
WO 2010/130970 A1 11/2010
WO 2011/001434 A1 1/2011
WO 2011/003776 A2 1/2011
WO 2011/067745 A2 6/2011
WO 2011/080674 A2 7/2011
WO 2011/112570 A1 9/2011
WO 2011/132127 A1 10/2011
WO 2012/001626 A1 1/2012
WO 2012/056401 A1 5/2012
WO 2012/092580 A2 7/2012
WO 2013/010691 A1 1/2013
WO 2013/025670 A1 2/2013
WO 2013/039990 A1 3/2013
WO 2013/040005 A1 3/2013
WO 2013/040021 A1 3/2013
WO 2013/040033 A1 3/2013
WO 2013/040049 A1 3/2013

(56) References Cited

FOREIGN PATENT DOCUMENTS

| | | | |
|---|---|---|---|
| WO | 2013/040057 | A1 | 3/2013 |
| WO | 2013/040116 | A9 | 3/2013 |
| WO | 2013/040117 | A1 | 3/2013 |
| WO | 2013/040117 | A9 | 6/2013 |
| WO | 2013/175480 | A1 | 11/2013 |
| WO | 2014/106837 | A2 | 7/2014 |
| WO | 2014/106838 | A2 | 7/2014 |
| WO | 2014/151255 | A1 | 9/2014 |
| WO | 2014/164761 | A1 | 10/2014 |
| WO | 2014/164797 | A1 | 10/2014 |
| WO | 2015/010026 | A2 | 1/2015 |

OTHER PUBLICATIONS

Office Action dated Nov. 3, 2014, in Chinese Patent Application No. 201180012795.2.

Office Action dated Oct. 8, 2014, in Mexican Patent Application MX/a/2012/010479.

Paddison et al., "Stable suppression of gene expression by RNAi in mammalian cells," Proc. Natl Acad. Sci. USA, 99(3):1443-1448 (2002).

Palauqui et al., "Activation of systemic acquired silencing by localised introduction of DNA," Current Biology, 9:59-66 (1999).

Parera et al., "Dehydration Rate after Solid Matrix Priming Alters Seed Performance of Shrunken-2 Corn," J. Amer Soc. Hort. Sci., 119(3):629-635 (1994).

Peretz et al., "A Universal Expression/Silencing Vector in Plants," Plant Physiology, 145:1251-1263 (2007).

Pomprom et al., "Glutamine synthetase mutation conferring target-site-based resistance to glufosinate in soybean cell selections," Pest Manag Sci, 2009; 65(2):216-222 (2009).

Pratt et al., "*Amaranthus rudis* and *A. tuberculatus*, One Species or Two?," Journal of the Torrey Botanical Society, 128(3):282-296 (2001).

Preston et al., "Multiple effects of a naturally occurring proline to threonine substitution within acetolactate synthase in two herbicide-resistant populations of Lactuca serriola," Pesticide Biochem. Physiol., 84(3):227-235 (2006).

Qiwei,"Progress in DNA interference," Progress in Veterinary Medicine, 30(1):71-75 (2009).

Rajur et al., "Covalent Protein-Oligonucleotide Conjugates for Efficient Delivery of Antisense Molecules," Bioconjug Chem., 8:935-940 (1997).

Reddy et al., "Aminomethylphosphonic Acid Accumulation in Plant Species Treated with Glyphosate," J. Agric. Food Chem., 56(6):2125-2130 (2008).

Reither et al., "Specificity of DNA triple helix formation analyzed by a Fret assay," BMC Biochemistry, 3:27 (2002).

Riggins et al., "Characterization of De Nova Transcriptome for Waterhemp (*Amaranthus tuberculalus*) Using Gs-Flx 454 Pyrosequeneing and Its Application for Studies of Herbicide Target-Site Genes," Pest Manag. Sci., 56:1042-1052 (2010).

Rose et al., "Functional Polarity Is Introduced by Dicer Processing of Short Substrate RNAs," Nucleic Acids Research, 33(13):4140-4156 (2005).

Santoro et al., "A general purpose RNA-cleaving DNA enzyme," Proc. Natl. Acad. Sci. USA, 94:4262-4266 (1997).

Sathasivan et al., "Nucleotide sequence of a mutant acetolactate synthase gene from an imidazolinone-resistant *Arabidopsis thaliana* var. *Columbia*," Nucleic Acids Research, 18(8):2188-2193 (1990).

Schwab et al., "RNA silencing amplification in plants: Size matters," PNAS, 107(34):14945-14946 (2010).

Schweizer et al., "Double-Stranded RNA Interferes with Gene Function at the Single-Cell Level in Cereals", The Plant Journal, 2000, pp. 895-903, vol. 24, No. 6.

Schwember et al., "Drying Rates following Priming Affect Temperature Sensitivity of Germination and Longevity of Lettuce Seeds," HortScience, 40(3):778-781 (2005).

Second Chinese Office Action issued in Chinese Patent Application No. 201180012795.2, dated Jun. 10, 2014.

Seidman et al., "The potential for gene repair via triple helix formation," J Clin Invest., 112(4):487-494 (2003).

Selvarani et al., "Evaluation of seed priming methods to improve seed vigour of onion (*Allium cepa* cv. *Aggregatum*) and carrot (*Daucus carota*)," Journal of Agricultural Technology, 7(3):857-867 (2011).

Senthil-Kumar et al., "A Systematic Study to Determine the Extent of Gene Silencing in *Nicotiana benthamiana* and Other Solanaccac Species When Heterologous Gene Sequences Are Used for Virus-Induced Gene Silencing", New Phylologist, 176:782-791 (2007).

Sharma et al., "A simple and efficient Agrobacterium-mediated procedure for transformation of tomato," J. Biosci., 34(3):423 433 (2009).

Sijen et al., "On the Role of RNA Amplification in dsRNA-Triggered Gene Silencing," Cell, 107:465-476 (2001).

Singh et al., "Absorption and translocation of glyphosate with conventional and organosilicone adjuvants," Weed Biology and Management, 8:104-111 (2008).

Snead et al., "Molecular Basis for Improved Gene Silencing by Dicer Substrate Interfering RNA Compared With Other siRNA Variants," Nucleic Acids Research, 41(12):6209-6221 (2013).

Steeves et al., "Transgenic soybeans expressing siRNAs specific to a major sperm protein gene suppress Heterodera glycines reproduction," Funct. Plant Biol., 33:991-999 (2006).

Stevens et al., "New Formulation Technology—Sil Wet® Organosilicone Surfactants Have Physical and Physiological Properties Which Enhance the Performance of Sprays", Proceedings of the 9th Australian Weeds Conference, pp. 327-331 (1990).

Stevens, "Organosilicone Surfactants as Adjuvants for Agrochemicals", Journal of Pesticide Science, 1993, pp. 103-122, vol. 38.

Stock et al., "Possible Mechanisms for Surfactant-Induced Foliar Uptake of Agrochemicals", Pesticide Science, 1993, pp. 165-177, vol. 38.

Strat et al., "Specific and nontoxic silencing in mammalian cells with expressed long dsRNAs," Nucleic Acids Research, 34(13):3803-3810 (2006).

Street, "Why is DNA (and not RNA) a Stable Storage Form for Genetic Information?," Biochemistry Revisited, pp. 1-4 (2008).

Sudarsan et al., "Metabolite-binding RNA domains are present in the genes of eukaryotes," RNA, 9:644-647 (2003).

Sun et al., "A Highly efficient Transformation Protocol for Micro-Tom, a Model Cultivar for Tomato Functional Genomics," Plant Cell Physiol., 47(3):426-431 (2006).

Supplementary European Search Report for EP 12831567.8 dated Jan. 29, 2015.

Supplementary European Search Report for EP 12832415.9 dated Jan. 21, 2015.

Sutton et al., "Activity of Mesotrione on Resistant Weeds in Maize," Pest Manag. Sci., 58:981-984 (2002).

Takasaki et al., "An Effective Method for Selecting siRNA Target Sequences in Mammalian Cells," Cell Cycle, 3:790-795 (2004).

Tank Mixing Chemicals Applied to Peanut Crops: Are the Chemicals. Compatible?, College of Agriculture & Life Sciences, NC State University, AGW-653, pp. 1-11 (2004).

Taylor, "Seed Storage, Germination and Quality," The Physiology of Vegetable Crops, pp. 1-36 (1997).

Templeton et al., "Improved DNA: liposome complexes for increased systemic delivery and gene expression," Nature Biotechnology, 15:647-652 (1997).

Tepfer, "Risk assessment of virus resistant transgenic plants," Annual Review of Phytopathology, 40:467-491 (2002).

The Seed Biology Place, Website Gerhard Leubner Lab Royal Holloway, University of London, http://www.seedbiology.de/seedtechnology.asp, last updated May 2, 2012.

Isaacs et al., "Engineered riboregulators enable post-transcriptional control of gene expression," Nature Biotechnology, 22(7):841-847 (2004).

Ji et al., "Regulation of small RNA stability: methylation and beyond," Cell Research, 22:624-636 (2012).

Jofre-Garfias El al., "Agrobacerium-Mediated Transformation of Amaranthus Hypochondriacus: Light- and Tissue-Specific Expres-

(56) References Cited

OTHER PUBLICATIONS sion of a Pea Chlorophyll A/B-Binding Protein Promoter," Plant Cell Reports, 16:847-852 (1997).
Josse et al., "A DELLA in Disguise: SPATULA Restrains the Growth of the Developing *Arabidopsis* Seedling," Plant Cell, 23:1337-1351 (2011).
Kam et al., "Nanotube Molecular Transporters:? Internalization of Carbon Nanotube?Protein Conjugates into Mammalian Cells," J. Am. Chem. Soc., 126(22):6850-6851 (2004).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khan et al., "Matriconditioning of Vegetable Seeds to Improve Stand Establishment in Early Field Plantings," .1 Amer. Soc. Hon. Sci., 1 17(1):41-47 (1992).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kim et al., "Synthetic dsRNA Dicer substrates enhance RNAi potency and efficacy," Nature Biotechnology, 23(2):222-226 (2005).
Kirkwood, "Herbicides and Plants", Botanical Journal of Scotland, Jan. 1, 1993, pp. 447-462, vol. 46 Issue 3.
Kronenwett et al., "Oligodeoxyribonucleotide Uptake in Primary Human Hematopoietic Cells Is Enhanced by Cationic Llipids and Depends on the Hematopoietic Cell Subset," Blood, 91(3):852-862 (1998).
Kusaba, "RNA interference in crop plants", Current Opinion in Biotechnology, 2004, pp. 139-143, vol. 15, No. 2.
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Leopold et al., "Chapter 4: Moisture as a Regulator of Physiological Reaction in Seeds," Seed Moisture, CSSA Special Publication No. 14, pp. 51-69 (1989).
Li et al., "Establishment of a highly efficient transformation system for pepper (*Capsicum annuum* L.)," Plant Cell Reports, 21: 785-788 (2003).
Liu et al., "Carbon Nanotubes as Molecular Transporters for Walled Plant Cells," Nano Letters, 9(3):1007-1010 (2009).
Liu et al., "DNAzyme-mediated recovery of small recombinant RNAs from a 5S rRNA-derived chimera expressed in *Escherichia coli*," BMC Biotechnology, 10:85 (2010).
Llave et al., "Endogenous and Silencing-Associated Small RNAs in Plants," The Plant Cell, 14:1605-1619 (2002).
Lu et al., "OligoWalk: an online siRNA design tool utilizing hybridization thermodynamics," Nucleic Acids Research, 36: W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).
MacKenzie et al., "Transgenic Nicotiana Debneyii Expressing Viral Coat Protein Are Resistant to Potato Virus S Infection," Journal of General Virology, 71:2167-2170 (1990).
Maher III et al., "Inhibition of DNA binding proteins by oligonucleotide-directed triple helix formation," Science, 245(4919):725-730 (1989).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Masoud et al., "Constitutive expression of an inducible β-1,3-glucanase in alfalfa reduces disease severity caused by the oomycete pathogen *Phytophthora megasperma* f. sp medicaginis, but does not reduce disease severity of chitincontaining fungi," Transgenic Research, 5:313-323 (1996).
Matveeva et al., "Prediction of antisense oligonucleotide efficacy by in vitro methods," Nature Biotechnology, 16:1374-1375 (1998).
Meinke, et al., "Identifying essential genes in *Arabidopsis thaliana*," Trends Plant Sci., 13(9):483-491 (2008).
Misawa et al., "Expression of an Erwinia phytoene desaturase gene not only confers multiple resistance to herbicides interfering with carotenoid biosynthesis but also alters xanthophyll metabolism in transgenic plants," The Plant Journal, 6(4):481-489 (1994).
Misawa et al., "Functional expression of the Erwinia uredovora carotenoid biosynthesis gene crtl in transgenic plants showing an increase of ?-carotene biosynthesis activity and resistance to the bleaching herbicide norflurazon," The Plant Journal, 4(5):833-840 (1993).
Miura et al., "The Balance between Protein Synthesis and Degradation in Chloroplasts Determined Leaf Variegation in *Arabidopsis* yellow variegated Mutants," The Plant Cell, 19:1313-1328 (2007).
Molina et al., "Inhibition of Protoporphyrinogen Oxidase Expression in *Arabidopsis* Causes a Lesion-Mimic Phenotype That Induces Systemic Acquired Resistance," The Plant Journal, 1 7(6):667-678 (1999).
Molnar et al., "Plant Virus-Derived Small Interfering RNAs Originate Predominantly from Highly Structured Single-Stranded Viral RNAs," Journal of Virology, 79(12):7812-7818 (2005).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Moser et al., "Sequence-Specific Cleavage of Double Helical DNA by Triple Helix Formation," Science, 238:645-646 (1987).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated May 15, 2015, in U.S. Appl. No. 14/608,951.
Non-Final Office Action dated May 22, 2015, in U.S. Appl. No. 13/612,985.
Busch et al., "RNAi for Discovery of Novel Cropproection Products", Pflanzenchutz-Nachrichten Bayer, 2005, pp. 34-50, vol. 58 No. 1.
Roberts, "Fast-Track Applications: The Potential for Direct Delivery of Proteins and Nucleic Acids to Plant Cells for the Discovery of Gene Function", Plant Methods, Dec. 15, 2005, pp. 1-3, vol. 1 No. 12.
Basu et al., "Weed Genomics: New Tools to Understand Weed Biology", Trends in Plant Science, Jul. 17, 2004, pp. 391-398, vol. 9 No. 8.

(56) References Cited

OTHER PUBLICATIONS

Tenllado et al., "Double-Stranded RNA-Mediated Interference with Plant Virus Infection", Journal of Virology, Dec. 2001, pp. 12288-12297, vol. 75 No. 24.
Bart, "A Novel System for Gene Silencing Using siRNAs in Rice Leaf and Stem-Derived Protoplasts", Plant Methods, Jun. 29, 2006, pp. 13, No. 2.
Fraley et al., "Liposome-Mediated Delivery of Tobacco Mosaic Virus RNA into Tobacco Protoplasts: A Sensitive Assay for Monitoring Liposome-Protoplast Interactions", Proceedings of the National Academy of Sciences of the United States of America, Mar. 1982, pp. 1859-1863, vol. 79.
Tang et al., "Efficient Delivery of Small Interfering Rna to Plant Cells by a Nanosecond Pulsed Laser-Induced Stress Wave for Posttranscriptional Gene Silencing", Plant Science, May 15, 2006, pp. 375-381, vol. 171.
Waterhouse et al., "Exploring Plant Genomes by RNA-Induced Gene Silencing" Nature Reviews—Genetics, Jan. 2003, pp. 29-38, vol. 4.
Office Action for NZ Application 601784 dated Apr. 23, 2013.
YouTube video by General Electric Company "Silwet Surfactants," screen shot taken on Jan. 11, 2012 of video of www.youtube.com/watch?v=WBw7nXMqHk8 (uploaded Jul. 13, 2009).
Silwet L-77 Spray Adjuvant for agricultural applications, product description from Momentive Performance Materials, Inc.
European Cooperation in the field of Scientific and Technical Research—Memorandum of Understanding for COST Action FA0806 (2008).
Devgen "The mini-Monsanto" KBC Securities (2006).
Wardell, "Floral Activity in Solutions of Deoxyribonucleic Acid Extracted from Tobacco Sterns", Plant Physiology, 1976, pp. 855-861, vol. 57.
Yu et al., "Gene-for-gene Disease Resistance Without the Hypersensitive Response in *Arabidopsis* dnd1 Mutant", Proceedings of the National Academy of Sciences of the United States of America, Jun. 23, 1998, pp. 7819-7824, vol. 95 No. 13.
Yan et al., "Sprout Vacuum-Infiltration: A Simple and Efficient Agroinoculation Method for Viru-Induced Gene Silencingin Diverse Solanaceous Species", Plant Cell Reports, Sep. 2012, pp. 1713-1722, vol. 31 Issue 9.
Clough et al., "The *Arabidopsis* dnd1 "Defense, No Death" Gene Encodes a Mutated Cyclic Nucleotide-gated Ion Channel", Proceedings of the National Academy of Sciences of the United States of America, Aug. 2000, pp. 9323-9328, vol. 97 No. 16.
Thomas et al., "Size Constraints for Targeting Post-Transcriptional Gene Silencing and for RNA-Directed Methylation in Nicotiana Benthamiana using a Potato Virus X Vector", The Plant Journal, 2001, pp. 417-425, vol. 25 No. 4.
Liu et al., "Insecticidal Activity of Surfactants and Oils Against Silverleaf Whitefly (*Bemisia argentifolii*) Nymphs (Homoptera: Aleyrodidae) on Collards and Tomato", Pest Management Science, 2000, pp. 861-866, vol. 56.
Chen et al., "Transfection and Expression of Plasmid DNA in Plant Cells by Arginine-Rich Intracellular Delivery Peptide Without Protoplast Preparation", Federation of European Biochemical Societies Letters, 2007, pp. 1891-1897, vol. 581.
Kim et al., "Optimization of Conditions for Transient Agrobacterium-Mediated Gene Expression Assays in *Arabidopsis*", Plant Cell Reproduction, 2009, pp. 1159-1167, vol. 28.
Showalter, "Structure and Function of Plant Cell Wall Proteins", The Plant Cell, Jan. 1993, pp. 9-23, vol. 5.
"Agricultural Chemical Usage 2006 Vegetables Summart", Agricultural Statistics Board, Jul. 2007, pp. 1-372.
Kusaba, "RNA Interference in Crop Plants", Current Opinion in Biotechnology, 2004, pp. 139-143, vol. 15.
Stevens et al., "New Formulation Technology—SilWet® Organosilicone Surfactants Have Physical and Physiological Properties Which Enhance the Performance of Sprays", Proceedings of the 9th Australian Weeds Conference, Aug. 6-10, 1990, pp. 327-331.
Stevens, "Organosilicone Surfactants as Adjuvants for Agrochemicals", Pesticide Science, 1993, pp. 103-122, vol. 38, Issue 2-3.
Orbovic et al., "Foliar-Applied Surfactants and Urea Temporarily Reduce Carbon Assimilation of Grapefruit Leaves", Journal of the American Society for Horticultural Science, 2001, pp. 486-490, vol. 126, Issue 4.
Stock et al., "Possible Mechanisms for Surfactant-Induced Foliar Uptake of Agrochemicals", Pesticide Science, 1993, pp. 165-177, vol. 38, Issue 2-3.
Zhang et al., "Cationic Lipids and Polymers Mediated Vectors for Delivery of siRNA", Journal of Controlled Release, Oct. 18, 2007, pp. 1-10, vol. 123, Issue 1.
Office Action for U.S. Appl. No. 13/619,980 dated Apr. 7, 2016.
Schweizer et al., "Double-Stranded RNA Interferes with Gene Function at the Single-Cell Level in Cereals", The Plant Journal, Dec. 2000, pp. 895-903, vol. 24, Issue 6.
Chan et al., "A Cyclic Nucleotide-Gated Ion Channel, CNGC2, Is Crucial for Plant Development and Adaption to Calcium Stress1" , 2003 Scientific Correspondence, p. 728-731, vol. 132.
Kaplan et al., "Cyclic Nucleotide-Gated Channels in Plants", Federation of European Biochemical Societies (FEBS Letters, 2007, pp. 2237-2246, vol. 581.
Sun et al., "Down-Regulation of *Arabidopsis* DND1 Orthologs in Potato and Tomato Leads to Broad-Spectrum Resistance to Late Blight and Powdery Mildew", Transgenic Research, 2016, pp. 123-138, vol. 25.
Dalakouras et al., "Induction of Silencing in Plants by High-Pressure Spraying of In vitro-Synthesized Small RNAs", Frontiers in Plant Science, Aug. 2016, pp. 1-5, vol. 7, No. 1327.
Hu et al., "High Efficiency Transport of Quantum Dots into Plant Roots with the Aid of Silwet L-77", Plant Physiology and Biochemistry, Aug. 2010, pp. 703-709, vol. 48, Issue 8.
Jones-Rhoades et al., "MicroRNAs and Their Regulatory Roles in Plants", Annual Review of Plant Biology, 2006, pp. 19-53, vol. 57.
Brodersen et al., "The Diversity of RNA Silencing Pathways in Plants", Trends in Genetics, May 2006, pp. 268-280, vol. 22 No. 5.
Du et al., "A Systematic Analysis of the Silencing Effects of an Active siRNA at All Single-nucleotide Mismatched Target Sites", Nucleic Acids Research, 2005, pp. 1671-1677, vol. 33 No. 5.
Concise Descriptions of Relevance filed by a third party on Nov. 29, 2012 in U.S. Appl. No. 13/042,856.
Sun et al., "Antisense Oligodeoxynucleotide Inhibition as a Potent Strategy in Plant Biology: Identification of SUSIBA2 as a Transcriptional Activator in Plant Sugar Signalling", The Plant Journal, 2005, pp. 128-138, vol. 44.
Nowak et al., "A new and efficient method for inhibition of RNA viruses by DNA interference", The FEBS Journal, 2009, pp. 4372-4380, vol. 276.
Liu et al., "Comparative study on the interaction of DNA with three different kinds of surfactants and the formation of multilayer films", Bioelectrochemistry, 2007, pp. 301-307, vol. 70.
Melnyk et al., "Intercellular and systemic movement of RNA silencing signals", The EMBO Journal, 2011, pp. 3553-3563, vol. 30.
Reddy et al., "Organosilicone Adjuvants Increased the Efficacy of Glyphosate for Control of Weeds in Citrus (*Citrus* spp.)", HortScience, 1992, pp. 1003-1005, vol. 27 No. 9.
Maas et al., "Mechanism and optimized conditions for PEG mediated DNA transfection into plant protoplasts", Plant Cell Reports, 1989, pp. 148-151, vol. 8.
Hewezi et al., "Local infiltration of high- and low-molecular-weight RNA from silenced sunflower (*Helianthus annuus* L.) plants triggers post-transcriptional gene silencing in non-silenced plants", Plant Biotechnology Journal, 2005, pp. 81-89, vol. 3.
Dunoyer et al., "Small RNA Duplexes Function as Mobile Silencing Signals Between Plant Cells", Science, 2010, pp. 912-916, vol. 328.
Li et al., "The FAST technique: a simplified Agrobacterium-based transformation method for transient gene expression analysis in seedlings of *Arabidopsis* and other plant species", Plant Methods, 2009, vol. 5 No. 6.
Reynolds et al., "Rational siRNA Design for RNA Interference", Nature Biotechnology, Mar. 2004, pp. 326-330, vol. 22 No. 3.

(56) References Cited

OTHER PUBLICATIONS

Pei et al., "On the Art of Identifying Effective and Specific siRNAs", Nature Methods, 2006, pp. 670-676, vol. 3 No. 9.
Zhang et al., "Agrobacterium-Mediated Transformation of *Arabidopsis thaliana* Using the Floral Dip Method", Nature Protocols, 2006, pp. 641-646, vol. 1 No. 2.
Tomari et al., "Perspective: Machines for RNAi", Genes and Development, 2005, pp. 517-529, vol. 19.
Vaucheret, "Post-Transcriptional Small RNA Pathways in Plants: Mechanisms and Regulations", Genes and Development, 2006, pp. 759-771, vol. 20.
Meins et al., "RNA Silencing Systems and their Relevance to Plant Development", Annual Reviews—Cell and Developmental Biology, Nov. 2005, pp. 297-318, vol. 21.
Hamilton et al., "Two Classes of Short Interfering RNA in RNA Silencing" The EMBO Journal, Sep. 2, 2002, pp. 4671-4679, vol. 21 No. 17.
Hunter et al., "RNA Interference Strategy to Suppress Psyllids and Leafhoppers" International Plant and Animal Genome XIX, Jan. 15-19, 2011.
International Search Report and Written Opinion for PCT/US2011/027528 dated May 10, 2011.
Gan et al., "Bacterially Expressed dsRNA Protects Maize Against SCMV Infection", Plant Cell Reports, 2010, pp. 1261-1268, vol. 11.
Tenllado et al., "Crude Extracts of Bacterially Expressed dsRNA Can be Used to Protect Plants Against Virus Infection", BMC Biotechnology, 2003, pp. 1-11, vol. 3 No. 3.
Balcombe et al., "RNA Silencing and Heritable Epigenetic Effects in Tomato and *Arabidopsis*", Abstract 13th Annual Fall Symposium, Plant Genomes to Phenomes, Donal Danforth Plant Science, Sep. 28-30, 2011.
Himber et al., "Transitivity-Dependent and -Independent Cell-to-Cell Movement of RNA Silencing", The EMBO Journal, 2003, pp. 4523-4533, vol. 22 No. 17.
Ryabov et al., "Cell-to-Cell, but Not Long-Distance, Spread of RNA Silencing That is Induced in Individual Epidermal Cells", Journal of Virology, 2004, pp. 3149-3154, vol. 78 No. 6.
Cost Action FA0806 Progress Report "Plant Virus Control Employing RNA-Based Vaccines: A Novel Non-Transgenic Strategy", 2010.
Cough, "Floral Dip: A Simplified Method for Agrobacterium-Mediated Transformation of *Arabidopsis thaliana*", The Plant Journal, 1998, pp. 735-743, vol. 16 No. 6.
Klahre et al., "High Molecular Weight RNAs and Small Interfering RNAs Induce Systemic Posttranscriptional Gene Silencing in Plants", Proceedings of the National Academy of Sciences, 2002, pp. 11981-11986, vol. 99 No. 18.
Zhu et al., "Ingested RNA Interference for Managing the Populations of the Colorado Potato Beetle, *Liptinotarsa decemlineata*", Pest Management Science, 2010, pp. 175-182, vol. 67.
Wardell, "Floral Induction of Vegetative Plants Supplied a Purified Fraction of Deoxyribonucleic Acid from Stems of Flowering Plants", Plant Physiology, 1977, pp. 885/891, vol. 60.
Zhao et al., "Phyllotreta Striolata (*Coleoptera: chrysomelidae*): Arginine Kinase Cloning and RNAi-Based Pest Control", European Journal of Entomology, 2008, pp. 815-822, vol. 105 No. 5.
Hannon, "RNA Interference", Nature Publishing Group, 2002, pp. 244-251, vol. 481.
Tenllado et al., "RNA Interference as a New Biotechnological Tool for the Control of Virus Diseases in Plants", Virus Research, 2004, pp. 85-96, vol. 102.
Gong et al., "Silencing of Rieske Iron-Sulfur Protein Using Chemically Synthesised siRNA as a Potential Biopesticide Against Plutella Xylostella" Pest Management Science, 2011, pp. 514-520, vol. 67.
Molnar et al., "Small Silencing RNAs in Plants are Mobile and Direct Epigenetic Modification in Recipient Cells", Science, 2010, pp. 872-875, vol. 328.
Sun et al., "Sweet Delivery—Sugar Translocators as Ports of Entry for Antisense Oligodeoxynucleotides in Plant Cells", The Plant Journal, 2007, pp. 1192-1198, vol. 52.
Vionnet et al., "Systemic Spread of Sequence-Specific Transgene RNA Degradation in Plants is Initiated by Localized Introduction of Ectopic Promoterless DNA", Cell, 1998, pp. 177-187, vol. 95.
An et al., "Transient RNAi Induction Against Endogenous Genes in *Arabidopsis* Protoplasts Using in Vitro-Prepared Double-Stranded RNA", Bioscience, Biotechnology and Biochemistry, 2005, pp. 415/418, vol. 69 No. 2.
Artymovich, "Using RNA Interference to Increase Crop Yield and Decrease Pest Damage", MMG 445 Basic Biotechnology, 2009, pp. 7-12, vol. 5 No. 1.
Paungfoot-Lonhienne et al., "The DNA is Taken Up by Root Hairs and Pollen, and Stimulates Root and Pollen Tube Growth", Plant Physiology, 2010, pp. 799-805, vol. 153.
Paungfoot-Lonhienne et al., "DNA Uptake by *Arabidopsis* Induces Changes in the Expression of CLE Peptides Which Control Root Morphology", Plant Signaling and Behavior, 2010, pp. 1112-1114, vol. 5 No. 9.
International Preliminary Report on Patentability for PCT/US2011/027528 dated Sep. 9, 2011.
Gaines et al., "Gene Amplification Confers Glyphosate Resistance in Amaranthus Palmeri", PNAS, 2010, pp. 1029-1034, vol. 107 No. 3.
Kirkwood, "Use and Mode of Action of Adjuvants for Herbicides: A Review of Some Current Work", Pest Management Science, 1993, pp. 93-102, vol. 3.
Kusaba et al., "Low Glutelin Content1: A Dominant Mutation that Suppresses the Glutelin Multigene Family via RNA Silencing in Rice", The Plant Cell, Jun. 2003, pp. 1455-1467, vol. 15 No. 6.
Unnamalai, "Cationic Oligopeptide-Mediated Delivery of dsRNA for Post-Transcriptional Gene Silencing in Plant Cells", FEBS Letters, May 21, 2004, pp. 307-310, vol. 566 No. 1.
Al-Kaff et al., "Plants Rendered Herbicide-Susceptible by Cauliflower Mosaicviurs-Elicited Suppression of a 355 Promoter-Regulated Transgene", Nature Biotechnology, Sep. 2000, pp. 995-999, vol. 18 No. 9.
Gao et al., "Nonviral Methods for siRNA Delivery", Molecular Pharmaceutics, Dec. 30, 2008, pp. 651-658, vol. 6 No. 3.
AccuStandard, Inc., "Pesticide Standards Reference Guide", 2010, 116 pages.
Austrailian Government, Grains Research & Development Corporation, "Adjuvants: Oils, Surfactants and other Additives for Farm Chemicals", 2012, 52 pages.
Consonni et al., "Conserved Requirement for a Plant Host Cell Protein in Powdery Mildew Pathogenesis", Nature Genetics, 2006, pp. 716-720, vol. 38, No. 6.
Eichmann et al., "BAX Inhibitor-1 Is Required for Full Susceptibility of Barley to Powdery Mildew", Molecular Plant-Microbe Interactions, 2010, pp. 1217-1227, vol. 23 No. 9.
Eichmann et al., "The Barley Apoptosis Suppressor Homologue BAX Inhibitor-1 Compromises Nonhost Penetration Resistance of Barley to the Inappropriate Pathogen *Blumeria graminis* F. Sp. *Tritici*", Molecular Plant-Microbe Interactions, 2004, pp. 484-490, vol. 17, No. 5.
First Examination Report issued for New Zealand Application No. 601784 dated Apr. 23, 2013.
Gelvin, "Agrobacterium-Mediated Plant Transformation: The Biology Behind the "Gene-Jockeying" Tool", Microbiology and Molecular Biology Reviews, Mar. 2003, p. 16-37, vol. 67 No. 1.
Huckelhoven et al., "Overexpression of Barley BAX Inhibitor 1 Induces Breakdown of mlo-Mediated Penetration Resistance to Blumeria Graminis", Proceedings of the National Academy of Sciences, Apr. 29, 2003, pp. 5555-5560, vol. 100 No. 9.
Humphry et al., "Durable Broad-Spectrum Powdery Mildew Resistance in Pea ER1 Plants is Conferred by Natrual Loss-of-Function Mutations in PsMLO1", Molecular Plant Pathology, 2011, pp. 866-878, vol. 12, No. 9.
International Preliminary Report on Patentability for PCT/US2011/027528 dated Sep. 11, 2012.
International Search Report and Written Opinion issued in PCT/US13/61475, dated Apr. 8, 2014.
Kozomara et al., "miRBase: Annotating High Confidence MicroRNAs Using Deep Sequencing Data", Nucleic Acids Research, 2014, p. D68-D73, vol. 42.

(56) References Cited

OTHER PUBLICATIONS

Lu et al., "Novel and Mechanical Stress-Responsive MicroRNAs in Populus Trichocarpa That Are Absent from *Arabidopsis*", The Plant Cell, Aug. 2005, pp. 2186-2203, vol. 17.
Mallory et al., "MicroRNA Control of Phabulosa in Leaf Development: Importance of Pairing to the MicroRNA 5' Region", The EMBO Journal, 2004, pp. 3356-3364, vol. 23 No. 16.
Mansoor et al., "Engineering Novel Traits in Plants Through RNA Interference", Trends in Plant Science, 2006, pp. 559-565, vol. 11, No. 11.
Momentive Performance Materials Inc. Marketing Bulleting for Silwet L-77* Ag spray adjuvant DA Performance Additives, 2011, pp. 1-4.
Piffanelli et al., "A Barely Cultivation-Associated Polymorphism Conveys Resistance to Powdery Mildew", Nature, 2004, pp. 887-891, vol. 430.
Piffanelli et al., "The Barely MLO Modulator of Defense and Cell Death is Responsive to Biotic and Abiotic Stress Stimuli", Plant Physiology, Jul. 1, 2002, pp. 1076-1085, vol. 129.
Sato et al., "Development of 5006 Full-Length CDNAs in Barley: A Tool for Accessing Cereal Genomics Resources", DNA Research, Jan. 15, 2009, pp. 81-98, vol. 16.
Senthil-Kumar et al., "RNAi in Plants: Recent Developments and Applications in Agriculture", Gene Silencing: Theory, Techniques and Applications, Oct. 1, 2010, p. 185, Retrieved from the Internet: URL: https://www.researchgate.net/profile/Senthil-Kumar_Muthappa/publication/216017213_RNAi_in_Plants_Recent_Developments_and_Applicationsin_Agriculture/links/097fe5ffe6c103ae5cc028f6.pdf, Retrieved on Feb. 14, 2017.
Solano et al., "Isolation and Characterization of Strain MMB-1 (CECT 4803), a Novel Melanogenic Marine Bacterium," Appl. Environ. Microbiol., 1997, pp. 3499, vol. 63 No. 9.
Somerville et al., "Plant Functional Genomics" Science, 285:380-383 (1999).
Varallyay et al., "Virus-Induced Gene Silencing of Mlo Genes Induces Powdery Mildew Resistence in Triticum aestivum", Archives of Virology: Official Journal of the Virology Division of the International Union of Micobiological Societies, 2012, pp. 1345-1350, vol. 157, No. 7.
Wang et al., "A Web-Based Design Center for Vector-Based siRNA and siRNA Cassette", Biolnformatic Applications Note, 2004, pp. 1818-1820, vol. 20 No. 11.
Warnasooriya et al., "Using transgenic modulation of protein synthesis and accumulation to probe protein signaling networks in *Arabidopsis thaliana*" Plant Signaling & Behavior, 6(9):1312-1321 (2011).
Watanabe et al., "Bax Inhibitor-1, a Conserved Cell Death Suppressor, Is a Key Molecular Switch Downstream from a Variety of Biotic and Abiotic Stress Signals in Plants", International Journal of Molecular Sciences, Jul. 10, 2009, pp. 3149-3167, vol. 10.
Yuan et al., "A High Throughput Barley Strip Mosaic Virus Vector for Virus Induced Gene Silencing in Monocots and Dicots", PLOS One, Oct. 21, 2011, pp. 1-16, vol. 6 Issue 10 e26468.
Zhai et al., "Establishing RNA Interference as a Reverse-Genetic Approach for Gene Functional Analysis in Protoplasts" Plant Physiology, 149:642-652 (2009).
European Supplemental Search Report dated Oct. 8, 2013 in Application No. 11753916.3.
Extended European Search Report dated Jun. 29, 2015, in European Patent Application No. 12831494.5.
Farooq et al., "Rice seed priming," IPRN, 30(2):45-48 (2005).
Final Office Action dated Nov. 7, 2013, in U.S. Appl. No. 13/042,856.
Fire et al., "Potent and specific genetic interference by double-stranded RNA in Caenorhabditis elegans," Nature, 391:806-811 (1998).
First Examination Report dated Jul. 28, 2014, in New Zealand Patent Application No. 627060.
First Office Action dated May 27, 2015, in Chinese Patent Application No. 201280054179.8.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," The Journal of Biological Chemistry, 270(30):18147-18149 (1995).
Fukuhara et al., "The wide distribution of endornaviruses, large double-stranded RNA replicons with plasmid-like properties," Archives of Virology, 151:995-1002 (2006).
Further Examination Report issued in New Zealand Patent Application No. 601784 dated May 16, 2014.
Ge et al., "Rapid vacuolar sequestration: the horseweed glyphosate resistance mechanism," Pest Management Sci., 56:345-348 (2010).
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005: Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. GI:186478573, published Jan. 22, 2014.
GenEmbl FJ861243, published Feb. 3, 2010.
Gressel et al., "A Strategy to Provide Long-Term Control of Weedy Rice While Mitigating Herbicide Resistance Transgene Flow, and Its Potential Use for Other Crops with Related Weeds", Pest Management Science, 2009, pp. 723-731, vol. 65.
Gutensohn et al., "Functional analysis of the two *Arabidopsis* homologues of Toc34, a component of the chloroplast protein import apparatus," The Plant Journal, 23(6):771-783 (2000).
Haigh, "The Priming of Seeds: Investigation into a method of priming large quantities of seeds using salt solutions," Thesis submitted to Macquarie University (1983).
Han et al., "Molecular Basis for the Recognition of Primary microRNAs by the Drosha-DGCR8 Complex," Cell, 125(5):887-901 (2006).
Hardegree, "Drying and storage effects on germination of primed grass seeds," Journal of Range Management, 47(3):196-199 (1994).
Herman et al., "A three-component dicamba O-demethylase from Pseudomonas maltophilia, strain DI-6: gene isolation, characterization, and heterologous expression," J. Biol. Chem., 280: 24759-24767 (2005).
Hidayat et al., "Enhanced Metabolism of Fluazifop Acid in a Biotype of Digitaria sanguinalis Resistant to the Herbicide Fuazifop-P-Butyl," Pesticide Biochem. Physiol., 57:137-146 (1997).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium rumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," Plant Physiol., 107(2):469-477 (1995).
Hsieh et al., "A library of siRNA duplexes targeting the phosphoinositide 3-kinase pathway: determinants of gene silencing for usein cell-based screens," Nucleic Acids Res., 32(3):893-901 (2004).
Huesken et al., "Design of a genome-wide siRNA library using an artificial neural network," Nature Biotechnology, 23(8): 995-1001 (2005).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2014, in International Application No. PCT/IL13/50447.

(56) References Cited

OTHER PUBLICATIONS

International Search Report and the Written Opinion dated Feb. 25, 2013, in International Application No. PCT/US12/54883.
International Search Report and the Written Opinion dated Feb. 27, 2013, in International Application No. PCT/US12/54814.
International Search Report and the Written Opinion dated Feb. 27, 2013, in International Application No. PCT/US12/54842.
International Search Report and the Written Opinion dated Feb. 27, 2013, in International Application No. PCT/US12/54862.
International Search Report and the Written Opinion dated Feb. 27, 2013, in International Application No. PCT/US12/54894.
International Search Report and the Written Opinion dated Feb. 27, 2013, in International Application No. PCT/US12/54974.
International Search Report and the Written Opinion dated Feb. 27, 2013, in International Application No. PCT/US12/54980.
International Search Report and the Written Opinion dated Jul. 15 2014, in International Application No. PCT/US2014/025305.
Inetnational Search Report and the Written Opinion dated Jul. 22 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Jul. 8 2015 in International Application No. PCT/US2015/011408.
International Search Report and Written Opinion dated Mar. 26, 2015, in International Application No. PCT/US2014/069353.
International Search Report dated Mar. 12, 2013 in International Application No. PCT/US 12/54789.
Agrios, Plant Pathology (Second Edition), 2:466-470 (1978).
Alarcón-Reverte et al., "Resistance to ACCase-inhibiting herbicides in the weed Lolium multiflorum," Comm. Appl. Biol. Sci., 73(4):899-902 (2008).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
Anonymous, "A handbook for high-level expression and purification of 6xHis-tagged proteins," The QIAexpressionist, (2003).
Anonymous, "Do Monsanto Have the Next Big Thing?" Australian Herbicide Resistance Initiative (AHRI), retreived on Jan. 19, 2015, XP007922963.
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (*Solanum melongena* L) resistant to Colorado Potato Beetle (*Leptinotarsa decemlineata* Say)," (1997) Theor. Appl. Genet., 95:329-334 (1997).
Australian Patent Examination report No. 1 dated Nov. 11, 2013, in Australian Application No. 2011224570.
Axtell et al., "A Two-Hit Trigger for siRNA Biogenesis in Plants," Cell, 127:565?577 (2006).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al., "Naturally Occurring Broad-Spectrum Powdery Mildew Resistance in a Central American Tomato Accession Is Caused by Loss of Mb Function," MPMI, 2I(1):30-39 (2008).
Banerjee et al., "Efficient production of transgenic potato (*S. tuberosum* L ssp. *andigena*) plants via Agrobacterium tumefaciens-mediated transformation," Plant Sci., 170:732 738 (2006).
Bayer et al., "Programmable ligand-controlled riboregulators of eukaryotic gene expression," Nature Biotechnol., 23(3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5(2):299-307 (1994).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," FEBS Letters, 580:789-794 (2006).
Bourgeois et al., "Field and Producer Survey of Accase Resistant Wild Oat in Manitoba," Canadian Journal of Plant Science, 709-7 15 (1997).
Breaker et al., "A DNA enzyme with Mg2+-dependent RNA phosphoesterase activity," Chemistry and Biology, 2:655-660 (1995).
Brugière et al., "Glutamine Synthetase in the Phloem Plays a Major Role in Controlling Proline Production," The Plant Cell, 11:1995-2011(1999).
Busi et al., "Gene Flow Increases the Initial Frequency of Herbicide Resistance Alleles in Unselected Lolium Rigidum Populations", Agriculture, Ecosystems and Environments, 2011, pp. 403-409, vol. 142.
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Chabbouh et al., "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Cellular Internalization of Fluorescent Proteins via Arginine-Rich Intracellular Delivery Peptide in Plant Cells", Plant Cell Physiology, 2005, pp. 482-488, vol. 46.
Chee et al., "Transformation of Soybean (*Glycine max*) by Infecting Germinating Seeds with Agrobacterium tumefaciens," Plant Physiol., 91:1212-1218 (1989).
Chen et al., "In Vivo Analysis of the Role of atTic20 in Protein Import into Chloroplasts," The Plant Cell, 14:641-654 (2002).
Cheng et al., "Production of fertile transgenic peanut (*Arachis hypogaea* L.) plants using Agrobacterium tumefaciens," Plant Cell Reports, 15:653-657 (1996).
Chi et al., "The Function of RH22, a DEAD RNA Flelicase, in the Biogenesis of the 50S Ribosomal Subunits of *Arabidopsis* Chloroplasts," Plant Physiology, 158:693-707 (2012).
Chinese Office Action dated Aug. 28, 2013 in Chinese Application No. 201180012795.2.
Chupp et al., "Chapter 8: White Rust," Vegetable Diseases and Their Control, The Ronald Press Company, New York, pp. 267-269 (1960).
Colboume et al., "The Ecoresponsive Genome of Daphnia pulex," Science, 331(6017):555-561 (2011).
Colombian Office Action dated Aug. 2, 2013 in Application No. 12 152898.
Colombian Office Action dated Feb. 21, 2014 in Application No. 12 152898.
Communication pursuant to Article 94(3) EPC dated Jun. 26, 2015, as received in European Patent Application No. 11 753 9163.
Dalakouras et al., "Induction of Silencing in Plants by High-Pressure Spraying of In vitro-Sythesized Small RNAs", Frontiers in Plant Science, Aug. 2016, pp. 1-5, vol. 7, No. 1327.

(56) References Cited

OTHER PUBLICATIONS

Dalmay et al., "An RNA-Depenedent RNA Polymerase Gene in Arabidopsis Is Required for Posttranscriptional Gene Silencing Mediated by a Transgene but Not by a Virus," Cell, 101:543-553 (2000).
Datebase EMBL CBIB Daphnia—XP-002732239 (2011).
Davidson et al., "Engineering regulatory RNAs," Trends in Biotechnology, 23(3):109-112 (2005).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
Della-Cioppa et al., "Import of a precursor protein into chloroplasts is inhibited by the herbicide glyphosate," The EMBO Journal, 7(5):1299-1305 (1988).
Diallo et al., "Long Endogenous dsRNAs Can Induce Complete Gene Silencing in Mammalian Cells and Primary Cultures," Oligonucleotides, 13:381-392 (2003).
Ellington et al., "In vitro selection of RNA molecules that bind specific ligands," Nature, 346:818-822 (1990).
Emery et al., "Radial Patterning of Arabidopsis Shoots by Class III HD-ZIP and KANADI Genes," Current Biology, 13:1768-1774 (2003).
Eurasian Office Action dated Feb. 24, 2014, in Application No. 201201264.
Thompson, et al., "CLUSTAL W: improving the sensitivity of progressive multiple sequence alignment through sequence weighting, position-specific gap penalties and weight matrix choice," Nucl. Acids Res., 22(22):4673-4680 (1994).
Timmons et al., "Specific interference by ingested dsRNA," Nature, 395:854 (1998).
Toriyama et al., "Transgenic Rice Plants After Direct Gene Transfer Into Protoplasts", Biotechnology, 1988, pp. 1072-1074, vol. 6.
Tran et al., "Control of specific gene expression in mammalian cells by co-expression of long complementary RNAs," FEBS Lett.;573(1-3):127-134 (2004).
Tranel et al., "Resistance of Weeds to ALS-Inhibiting Herbicides: What Have We Learned?," Weed Science, 50:700-712 (2002).
Tuschl, "Expanding small RNA interference," Nature Biotechnol., 20: 446-448 (2002).
Tuschl, "RNA Interference and Small Interfering RNAs," ChemBiochem. 2(4):239-245 (2001).
Töpfer et al., "Uptake and Transient Expression of Chimeric Genes in Seed-Derived Embryos," Plant Cell, 1:133-139 (1989).
Ui-Tei et al., "Guidelines for the selection of highly effective siRNA sequences for mammalian and chick RNA Interference," Nucleic Acids Res., 32(3): 936-948 (2004).
Urayama et al., "Knock-down of OsDCL2 in Rice Negatively Affects Maintenance of the Endogenous dsRNA Virus, *Oryza sativa* Endomavirus," Plant and Cell Physiology, 51(1):58-67 (2010).
Van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bioilechnology,10:667-674 (1992).
Vencill et al., "Resistance of Weeds to Herbicides," Herbicides and Environment, 29:585-594 (2011).
Verma et al., "Modified oligonucleotides: synthesis and strategy for users," Annu. Rev. Biochem., 67:99-134 (1998).
Vermeulen et al., "The Contributions of dsRNA Structure to Dicer Specificity and Efficiency," RNA, 11(5):674-682 (2005).
Vert et al., "An accurate and interpretable model for siRNA efficacy prediction," BMC Bioinformatics, 7:520 (2006).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).
Wan et al., "Generation of Large Numbers of Independently Transformed Fertile Barley Plants," Plant Physiol., 104:37-48 (1994).
Waterhouse et al., "Virus resistance and gene silencing in plants can be induced by simultaneous expression of sense and antisense RNA," Proc Natl Acad Sci USA, 95:13959-13964 (1998).
Welch et al., "Expression of ribozymes in gene transfer systems to modulate target RNA levels," Curr Opin Biotechnol. 9(5):486-496 (1998).
Written Opinion dated May 8, 2014, in International Application No. PCT/IL2013/050447.
Written Opinion dated Sep. 4, 2014, in Singapore Patent Application No. 201206152-9.
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "A novel rice gene, NRR responds to macronutrient deficiency and regulates root growth," Mol Plant, 5(1):63-72 (2012).
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Ge et al., "Rapid vacuolar sequestration: the horseweed glyphosate resistance mechanism," Pest Management Sci., 66:345-348 (2010).
SenBank Accession No. AY545657.1, published 2004.
Hidayat et al., "Enhanced Metabolism of Fluazifop Acid in a Biotype of Digitaria sanguinalis Resistant to the Herbicide-Fluazifop-P-Butyl," Pesticide Biochem. Physiol., 57:137-146 (1997).
Hoekema et al., "A binary plant vector strategy based on separation of vir- and T-region of the Agrobacterium tumefaciens Ti-plasmid," Nature, 303:179-180 (1983).
International Search Report and the Written Opinion dated Jul. 22, 2014, in International Application No. PCT/IL2013/051083.
Office Action dated Nov. 19, 2014, in Eurasian Patent Application No. 201201264128.
Preston et al., "Multiple effects of a naturally occurring proline to threonine substitution within acetolactate synthase in wo herbicide-resistant populations of Lactuca serriola," Pesticide Biochem. Physiol., 84(3):227-235 (2006).

* cited by examiner

DND1 topical to soybean cyst counts cyst number 400
350
300
250
200
150
100
50
0

T5336,T5348,T5343,T5337 as ssDNA coding
T5339,T5344,T5349,T5338 as ssDNA coding
T5345,T5347,T5340, T5341as ssDNA coding
T5350,T5346 T,5342 as ssDNA coding
T5358,T5363,T5352,T5364 as ssDNA promoter
T5353,T5360,T5359,T5357 as ssDNA promoter
T5354,T5351,T5366 as ssDNA promoter
T5355,T5365,T5356 as ssDNA promoter
T5367,T5362,T5361 as ssDNA promoter
T4782-85 pool control ssDNA
blank Trigger pools @ 80 nmol/plant

METHODS AND COMPOSITIONS FOR PLANT PEST CONTROL

PRIORITY CLAIMS AND REFERENCE TO RELATED APPLICATIONS

This application is a Continuation of U.S. patent application Ser. No. 14/209,108, filed on Mar. 13, 2014, which claims the benefit of U.S. Provisional Patent Application No. 61/783,260, filed on Mar. 14, 2013, which is incorporated herein by reference in its entirety.

INCORPORATION OF SEQUENCE LISTING

A sequence listing is provided herewith as a part of this U.S. patent application via the USPTO's EFS system in the file named "40_70_59232_Seq_listing.txt" which is 101,482 bytes in size (measured in MS-Windows®), was created on Mar. 12, 2014, and is incorporated herein by reference in its entirety.

BACKGROUND OF THE INVENTION

Powdery mildews are fungal diseases that affect a wide range of plants including cereals, grasses, vegetables, ornamentals, weeds, shrubs, fruit trees, broad-leaved shade and forest trees, that is caused by different species of fungi in the order Erysiphales. The disease is characterized by spots or patches of white to grayish, talcum-powder-like growth that produce tiny, pinhead-sized, spherical fruiting structures (the cleistothecia or overwintering bodies of the fungus), that are first white, later yellow-brown and finally black. The fungi that cause powdery mildews are host specific and cannot survive without the proper host plant. They produce mycelium (fungal threads) that grow only on the surface of the plant and feed by sending haustoria, or root-like structures, into the epidermal cells of the plant. The fungi overwinter on plant debris as cleistothecia or mycelia. In the spring, the cleistothecia produce spores that are moved to susceptible hosts by rain, wind or insects.

Powdery mildew disease is particularly prevalent in temperate and humid climates, where they frequently cause significant yield losses and quality reductions in various agricultural settings including greenhouse and field farming. This affects key cereals (e.g. barley and wheat), horticultural crops (e.g. grapevine, pea and tomato) and economically important ornamentals (e.g. roses). Limited access to natural sources of resistance to powdery mildews, rapid changes in pathogen virulence and the time consuming introgression of suitable resistance genes into elite varieties has led to the widespread use of fungicides to control the disease. This has not surprisingly led to the evolution and spread of fungicide resistance, which is especially dramatic amongst the most economically important powdery mildews.

Downy mildew diseases are caused by oomycete microbes from the family Peronosporaceae that are parasites of plants. Peronosporaceae are obligate biotrophic plant pathogens and parasitize their host plants as an intercellular mycelium using haustoria to penetrate the host cells. The downy mildews reproduce asexually by forming sporangia on distinctive white sporangiophores usually formed on the lower surface of infected leaves. These constitute the "downy mildew" and the initial symptoms appear on leaves as light green to yellow spots. The sporangia are wind-dispersed to the surface of other leaves. Depending on the genus, the sporangia may germinate by forming zoospores or by germ-tube. In the latter case, the sporangia behave like fungal conidia and are often referred to as such. Sexual reproduction is via oospores.

Most Peronosporaceae are pathogens of herbaceous dicots. Some downy mildew genera have relatively restricted host ranges, e.g. *Basidiophora, Paraperonospora, Protobremia* and *Bremia* on Asteraceae; *Perofascia* and *Hyaloperonospora* almost exclusively on Brassicaceae; *Viennotia, Graminivora, Poakatesthia, Sclerospora* and *Peronosclerospora* on Poaceae, *Plasmoverna* on Ranunculaceae. However, the largest genera, *Peronospora* and *Plasmopara*, have very wide host ranges.

In commercial agriculture, downy mildews are a particular problem for growers of crucifers, grapes and vegetables that grow on vines. Peronosporaceae of economic importance include *Plasmopara viticola* which infect grapevines, *Peronospora tabacina* which causes blue mold on tobacco, *Bremia lactucae*, a parasite on lettuce, and *Plasmopara halstedii* on sunflower.

Rusts (Pucciniales, formerly Uredinales) are obligate biotrophic parasites of vascular plants. Rusts affect a variety of plants; leaves, stems, fruits and seeds and is most commonly seen as coloured powder, composed of tiny aeciospores which land on vegetation producing pustules, or uredia, that form on the lower surfaces. During late spring or early summer, yellow orange or brown, hairlike or ligulate structures called telia grow on the leaves or emerge from bark of woody hosts. These telia produce teliospores which will germinate into aerial basidiospores, spreading and causing further infection.

The Death No Defense 1 (DND1) gene was identified from an *Arabidopsis* mutant unable to mount a Hypersensitive Response upon challenge by avirulent *Pseudomonas syringae* strains but nevertheless able to control pathogen infection (Yu I C, Parker J, Bent A F. Gene-for-gene disease resistance without the hypersensitive response in *Arabidopsis* dnd1 mutant. Proc Natl Acad Sci USA. 1998 95(13): 7819-24.). The DND1 mutant was subsequently shown to be a loss of function allele in the AtCNGC2, a cyclic nucleotide-gated ion channel which results in constitutively elevated salicylic acid levels and increased pathogenesis-related (PR) gene expression (Clough S J et al. The *Arabidopsis* dnd1 "defense, no death" gene encodes a mutated cyclic nucleotide-gated ion channel. Proc Natl Acad Sci USA. 2000 97(16):9323-8). In addition to elevated resistance to *Pseudomonas*, the DND1 *Arabidopsis* mutant demonstrated higher resistance to *Xanthomonas campestris* pv. *campestris* and X c. pv. *Raphani* (bacteria), *Peronospora parasitica* (oomycete) and Tobacco ringspot virus. However plants exhibit a dwarf phenotype and were conditional lesion mimics under certain conditions

SUMMARY OF THE INVENTION

The present embodiments provide for compositions comprising polynucleotide molecules and methods for treating a plant to alter or regulate gene or gene transcript expression in the plant, for example, by providing RNA or DNA for inhibition of expression. Various aspects provide compositions comprising polynucleotide molecules and related methods for topically applying such compositions to plants to regulate endogenous DND1 genes in a plant cell. The polynucleotides, compositions, and methods disclosed herein are useful in decreasing levels of DND1 transcript and improving fungal disease and/or nematode resistance of a plant.

In one embodiment, the polynucleotide molecules are provided in compositions that can permeate or be absorbed into living plant tissue to initiate localized, partially systemic, or systemic gene inhibition or regulation. In certain embodiments, the polynucleotide molecules ultimately provide to a plant, or allow the in planta production of, RNA that is capable of hybridizing under physiological conditions in a plant cell to RNA transcribed from a target endogenous gene or target transgene in the plant cell, thereby effecting regulation of the endogenous DND1 target gene. In certain embodiments, regulation of the DND1 target gene, such as by silencing or suppression of the target gene, leads to the upregulation of another gene that is itself affected or regulated by decreasing the DND1 target gene's expression.

In certain aspects or embodiments, the topical application of a composition comprising an exogenous polynucleotide and a transfer agent to a plant or plant part according to the methods described herein does not necessarily result in nor require the exogenous polynucleotide's integration into a chromosome of the plant. In certain aspects or embodiments, the topical application of a composition comprising an exogenous polynucleotide and a transfer agent to a plant or plant part according to the methods described herein does not necessarily result in nor require transcription of the exogenous polynucleotide from DNA integrated into a chromosome of the plant. In certain embodiments, topical application of a composition comprising an exogenous polynucleotide and a transfer agent to a plant according to the methods described herein also does not necessarily require that the exogenous polynucleotide be physically bound to a particle, such as in biolistic mediated introduction of polynucleotides associated with a gold or tungsten particles into internal portions of a plant, plant part, or plant cell. An exogenous polynucleotide used in certain methods and compositions provided herein can optionally be associated with an operably linked promoter sequence in certain embodiments of the methods provided herein. However, in other embodiments, an exogenous polynucleotide used in certain methods and compositions provided herein is not associated with an operably linked promoter sequence. Also, in certain embodiments, an exogenous polynucleotide used in certain methods and compositions provided herein is not operably linked to a viral vector.

In certain embodiments, methods for improving fungal disease resistance and/or nematode resistance in a plant comprising topically applying compositions comprising a polynucleotide and a transfer agent that suppress the target DND1 gene are provided. In certain embodiments, methods for selectively suppressing the target DND1 gene by topically applying the polynucleotide composition to a plant surface at one or more selected seed, vegetative, or reproductive stage(s) of plant growth are provided. Such methods can provide for gene suppression in a plant or plant part on an as needed or as desired basis. In certain embodiments, methods for selectively suppressing the target DND1 gene by topically applying the polynucleotide composition to a plant surface at one or more pre-determined seed, vegetative, or reproductive stage(s) of plant growth are provided. Such methods can provide for DND1 gene suppression in a plant or plant part that obviates any undesired or unnecessary effects of suppressing the genes expression at certain seed, vegetative, or reproductive stage(s) of plant development.

In certain embodiments, methods for selectively improving fungal disease resistance and/or nematode resistance in a plant by topically applying the polynucleotide composition to the plant surface at one or more selected seed, vegetative, or reproductive stage(s) are provided. Such methods can provide for improved fungal disease resistance and/or nematode disease resistance in a plant or plant part on an as needed or as desired basis. In certain embodiments, methods for selectively improving fungal disease and/or nematode resistance in a plant by topically applying the polynucleotide composition to the plant surface at one or more predetermined seed, vegetative, or reproductive stage(s) are provided. Such methods can provide for improving fungal disease and/or nematode resistance in a plant or plant part that obviates any undesired or unnecessary effects of suppressing DND1 gene expression at certain seed, vegetative, or reproductive stage(s) of plant development.

Polynucleotides that can be used to suppress a DND1 include, but are not limited to, any of: i) polynucleotides comprising at least 18 contiguous nucleotides that are essentially identical or essentially complementary to a gene or a transcript of the gene(s) of SEQ ID NO: 1-33; ii) polynucleotides comprising at least 18 contiguous nucleotides that are essentially identical or essentially complementary to a polynucleotides of SEQ ID NO: 34-59; iii) polynucleotides of SEQ ID NO: 34-59 (Table 2); or iv) SEQ ID NO: 64-67 (Table 4). Methods and compositions that provide for the topical application of certain polynucleotides in the presence of transfer agents can be used to suppress DND1 gene expression in an optimal manner. In certain embodiments, the compositions provided herein can be applied on an "as needed" basis upon scouting for the occurrence of fungal disease or nematodes. In certain embodiments, the compositions can be applied in a manner that obviates any deleterious effects on yield or other characteristics that can be associated with suppression of DND1 gene expression in a crop plant. The applied polynucleotides are complementary to the DND1 target host gene in plants and their topical application leads to suppression of the DND1 gene's activity.

Provided herein are compositions and methods for controlling plant fungal diseases. Plant fungal diseases that can be controlled with the methods and compositions provided herein include, but are not limited to, obligate biotrophic powdery mildew, downy mildew and rust fungal infestations in plants. In certain embodiments, methods and compositions for reducing expression of one or more host plant DND1 polynucleotide and/or protein molecules in one or more cells or tissues of the plant such that the plant is rendered less susceptible to fungal infections from the order Erysiphales, the family Peronosporaceae or the order Pucciniales, are provided. In certain embodiments, nucleotide and amino acid sequences of plant DND1 genes which can be downregulated by methods and compositions provided herein to increase plant resistance to powdery mildew, downy mildew or rust infection are disclosed.

Also provided herein are methods and compositions that provide for reductions in expression of DND1 target polynucleotide and protein molecules in at least the cells of a plant root and for improved resistance to nematodes. Nematodes that can be controlled by the methods and compositions provided herein include, but are not limited to, root knot nematodes (such as *Meloidogyne* sp.), cyst nematodes (such as *Globodera* sp. and *Heterodera* sp.), lesion nematodes (such as *Pratylenchus* sp.), and the like. In certain embodiments, DND1 expression is reduced in plant root cells from which nematodes feed by providing topically to plant leaves, shoots, roots and/or seeds compositions comprising polynucleotides that comprise at least 18 contiguous nucleotides that are essentially identical or essentially complementary to a DND1 gene or to a transcript of the DND1 gene; and a transfer agent.

Also provided are methods and compositions where topically induced reductions in DND1 transcript or protein levels are used to achieve powdery mildew, downy mildew or rust control while minimizing deleterious pleotropic effects in the host plant. Such methods and compositions provide for optimized levels of DND1 gene inhibition and/or optimized timing of DND1 gene inhibition.

Certain embodiments are directed to methods for producing a plant exhibiting an improvement in fungal disease resistance and/or nematode resistance comprising topically applying to a plant surface a composition that comprises:

a. at least one polynucleotide that comprises at least 18 contiguous nucleotides that are essentially identical or essentially complementary to a DND1 gene or to a transcript of the gene; and b. a transfer agent, wherein the plant exhibits an improvement in fungal disease resistance and/or nematode resistance that results from suppression of the DND1 gene. In certain embodiments, the polynucleotide molecule comprises sense ssDNA, sense ssRNA, dsRNA, dsDNA, a double stranded DNA/RNA hybrid, anti-sense ssDNA, or anti-sense ssRNA. In certain embodiments, the polynucleotide is selected from the group consisting of SEQ ID NO: 34-59, or wherein the polynucleotide comprises at least 18 contiguous nucleotides that are essentially identical or essentially complementary to SEQ ID NO: 1-33. In certain embodiments, the polynucleotide comprises at least 18 contiguous nucleotides that are essentially identical or essentially complementary to SEQ ID NO: 64-67. In certain embodiments: (a) the plant is a cucumber plant, the gene or the transcript is a cucumber DND1 gene or transcript, and the polynucleotide comprises at least 18 contiguous nucleotides that are essentially identical or essentially complementary to SEQ ID NO: 1, 3, 7, 11, or 19; (b) the plant is a soybean plant, the gene or the transcript is a soybean DND1 gene or transcript, and the polynucleotide molecule is selected from the group consisting of SEQ ID NO: 34-59, or the polynucleotide comprises at least 18 contiguous nucleotides that are essentially identical or essentially complementary to SEQ ID NO: 2, 4, 21, or 31; (c) the plant is a lettuce plant, the gene or the transcript is a lettuce DND1 gene or transcript, and the polynucleotide comprises at least 18 contiguous nucleotides that are essentially identical or essentially complementary to SEQ ID NO: 5 or 9; (d) the plant is a tomato plant, the gene or the transcript is a tomato DND1 gene or transcript, and the polynucleotide comprises at least 18 contiguous nucleotides that are essentially identical or essentially complementary to SEQ ID NO: 6, 10, 64, 65, 66 or 67; (e) the plant is a barley plant, the gene or the transcript is a barley DND1 gene or transcript, and the polynucleotide comprises at least 18 contiguous nucleotides that are essentially identical or essentially complementary to SEQ ID NO: 8 or 12; (f) the plant is a cotton plant, the gene or the transcript is a cotton DND1 gene or transcript, and the polynucleotide comprises at least 18 contiguous nucleotides that are essentially identical or essentially complementary to SEQ ID NO: 13, 14, 18, 25 or 26; (g) the plant is a melon plant, the gene or the transcript is a melon DND1 gene or transcript, and the polynucleotide comprises at least 18 contiguous nucleotides that are essentially identical or essentially complementary to SEQ ID NO: 15, 27, or 28; (h) the plant is a maize plant, the gene or the transcript is a maize DND1 gene or transcript, and the polynucleotide comprises at least 18 contiguous nucleotides that are essentially identical or essentially complementary to SEQ ID NO: 16, 20, 29, or 30; (i) the plant is a rice plant, the gene or the transcript is a rice DND1 gene or transcript, and the polynucleotide comprises at least 18 contiguous nucleotides that are essentially identical or essentially complementary to SEQ ID NO: 17, 22, 32, or 33; or, (j) the plant is a wheat plant, the gene or the transcript is a wheat DND1 gene or transcript, and the polynucleotide comprises at least 18 contiguous nucleotides that are essentially identical or essentially complementary to SEQ ID NO: 23 or 24. In certain embodiments, the composition comprises any combination of two or more polynucleotide molecules. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the composition further comprises a non-polynucleotide herbicidal molecule and the plant is resistant to the herbicidal molecule. In certain embodiments, the transfer agent comprises an organosilicone preparation. In certain embodiments, the polynucleotide is not operably linked to a viral vector. In certain embodiments, the polynucleotide is not integrated into the plant chromosome. Further embodiments are directed to: a plant made according to any of the above-described methods; progeny of plants that exhibit the improvements in fungal disease resistance and/or nematode resistance; seed of the plants, wherein seed from the plants exhibits the improvement in fungal disease resistance and/or nematode resistance; and a processed product of the plants, the progeny plants, or the seeds, wherein the processed products exhibit the improvement in fungal disease resistance and/or nematode resistance. In certain embodiments, the processed product of the plant or plant part exhibits an improved attribute relative to a processed product of an untreated control plant and the improved attribute results from the improved fungal disease resistance and/or nematode resistance. An improved attribute of a processed product can include, but is not limited to, decreased mycotoxin content, improved nutritional content, improved storage characteristics, improved flavor, improved consistency, and the like when compared to a processed product obtained from an untreated plant or plant part.

An additional embodiment is directed to a composition comprising a polynucleotide molecule that comprises at least 18 contiguous nucleotides that are essentially identical or essentially complementary to a DND1 gene or transcript of the gene, wherein the polynucleotide is not operably linked to a promoter; and, b) a transfer agent. In certain embodiments, the polynucleotide is selected from the group consisting of SEQ ID NO: 34-59, or the polynucleotide comprises at least 18 contiguous nucleotides that are essentially identical or essentially complementary to SEQ ID NO: 1-33. In certain embodiments, the polynucleotide comprises at least 18 contiguous nucleotides that are essentially identical or essentially complementary to SEQ ID NO: 64-67. In certain embodiments: (a) the plant is a cucumber plant, the gene or the transcript is a cucumber DND1 gene or transcript, and the polynucleotide comprises at least 18 contiguous nucleotides that are essentially identical or essentially complementary to SEQ ID NO: 1, 3, 7, 11, or 19; (b) the plant is a soybean plant, the gene or the transcript is a soybean DND1 gene or transcript, and the polynucleotide molecule is selected from the group consisting of SEQ ID NO: 34-59, or the polynucleotide comprises at least 18 contiguous nucleotides that are essentially identical or essentially complementary to SEQ ID NO: 2, 4, 21, or 31; (c) the plant is a lettuce plant, the gene or the transcript is a lettuce DND1 gene or transcript, and the polynucleotide comprises at least 18 contiguous nucleotides that are essentially identical or essentially complementary to SEQ ID NO: 5 or 9; (d) the plant is a tomato plant, the gene or the transcript is a tomato DND1 gene or transcript, and the polynucleotide comprises at least 18 contiguous nucleotides that are essentially identical or essentially complementary to SEQ ID NO: 6, 10, 64, 65, 66 or 67; (e) the plant is a barley plant, the gene or the transcript is a barley DND1 gene or transcript, and the polynucleotide comprises at least 18 contiguous nucleotides that are essentially identical or essentially complementary to SEQ ID NO: 8 or 12; (f) the plant is a cotton plant, the gene or the transcript is a cotton DND1 gene or transcript, and the polynucleotide comprises at least 18 contiguous nucleotides that are essentially identical or essentially complementary to SEQ ID NO: 13, 14, 18, 25 or 26; (g) the plant is a melon plant, the gene or the transcript is a melon DND1 gene or transcript, and the polynucleotide comprises at least 18 contiguous nucleotides that are essentially identical or essentially complementary to SEQ ID NO: 15, 27, or 28; (h) the plant is a maize plant, the gene or the transcript is a maize DND1 gene or transcript, and the polynucleotide comprises at least 18 contiguous nucleotides that are essentially identical or essentially complementary to SEQ ID NO: 16, 20, 29, or 30; (i) the plant is a rice plant, the gene or the transcript is a rice DND1 gene or transcript, and the polynucleotide comprises at least 18 contiguous nucleotides that are essentially identical or essentially complementary to SEQ ID NO: 17, 22, 32, or 33; or, (j) the plant is a wheat plant, the gene or the transcript is a wheat DND1 gene or transcript, and the polynucleotide comprises at least 18 contiguous nucleotides that are essentially identical or essentially complementary to SEQ ID NO: 23 or 24. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the transfer agent is an organosilicone preparation. In certain embodiments, the polynucleotide is not physically bound to a biolistic particle.

Another embodiment is directed to a method of making a composition comprising the step of combining at least: (a) a polynucleotide molecule comprising at least 18 contiguous nucleotides that are essentially identical or essentially complementary to a DND1 gene or transcript of a plant, wherein the polynucleotide is not operably linked to a promoter or a viral vector; and, (b) a transfer agent. In certain embodiments, the polynucleotide is obtained by in vivo biosynthesis, in vitro enzymatic synthesis, or chemical synthesis. In certain embodiments, the method further comprises combining with the polynucleotide and the transfer agent at least one of a non-polynucleotide herbicidal molecule, a polynucleotide herbicidal molecule, an insecticide, a fungicide, and/or a nematocide. In certain embodiments, the transfer agent is an organosilicone preparation.

Yet another embodiment is directed to a method of identifying a polynucleotide for improving fungal disease resistance and/or nematode resistance in a plant comprising; (a) selecting a population of polynucleotides that are essentially identical or essentially complementary to a DND1 gene or transcript of a plant; (b) topically applying to a surface of at least one of the plants a composition comprising at least one polynucleotide from the population and an transfer agent to obtain a treated plant; and, (c) identifying a treated plant that exhibits suppression of the DND1 gene or exhibits an improvement in fungal disease resistance or exhibits an improvement in nematode resistance, thereby identifying a polynucleotide that improves fungal disease resistance and/or nematode resistance in the plant. In certain embodiments, the polynucleotide is selected from the group consisting of SEQ ID NO: 34-59, or the polynucleotide comprises at least 18 contiguous nucleotides that are essentially identical or essentially complementary to SEQ ID NO: 1-33. In certain embodiments, the polynucleotide comprises at least 18 contiguous nucleotides that are essentially identical or essentially complementary to SEQ ID NO: 64-67. In certain embodiments: (a) the plant is a cucumber plant, the gene or the transcript is a cucumber DND1 gene or transcript, and the polynucleotide comprises at least 18 contiguous nucleotides that are essentially identical or essentially complementary to SEQ ID NO: 1, 3, 7, 11, or 19; (b) the plant is a soybean plant, the gene or the transcript is a soybean DND1 gene or transcript, and the polynucleotide molecule is selected from the group consisting of SEQ ID NO: 34-59, or the polynucleotide comprises at least 18 contiguous nucleotides that are essentially identical or essentially complementary to SEQ ID NO: 2, 4, 21, or 31; (c) the plant is a lettuce plant, the gene or the transcript is a lettuce DND1 gene or transcript, and the polynucleotide comprises at least 18 contiguous nucleotides that are essentially identical or essentially complementary to SEQ ID NO: 5 or 9; (d) the plant is a tomato plant, the gene or the transcript is a tomato DND1 gene or transcript, and the polynucleotide comprises at least 18 contiguous nucleotides that are essentially identical or essentially complementary to SEQ ID NO: 6, 10, 64, 65, 66 or 67; (e) the plant is a barley plant, the gene or the transcript is a barley DND1 gene or transcript, and the polynucleotide comprises at least 18 contiguous nucleotides that are essentially identical or essentially complementary to SEQ ID NO: 8 or 12; (f) the plant is a cotton plant, the gene or the transcript is a cotton DND1 gene or transcript, and the polynucleotide comprises at least 18 contiguous nucleotides that are essentially identical or essentially complementary to SEQ ID NO: 13, 14, 18, 25 or 26; (g) the plant is a melon plant, the gene or the transcript is a melon DND1 gene or transcript, and the polynucleotide comprises at least 18 contiguous nucleotides that are essentially identical or essentially complementary to SEQ ID NO: 15, 27, or 28; (h) the plant is a maize plant, the gene or the transcript is a maize DND1 gene or transcript, and the polynucleotide comprises at least 18 contiguous nucleotides that are essentially identical or essentially complementary to SEQ ID NO: 16, 20, 29, or 30; (i) the plant is a rice plant, the gene or the transcript is a rice DND1 gene or transcript, and the polynucleotide comprises at least 18 contiguous nucleotides that are essentially identical or essentially complementary to SEQ ID NO: 17, 22, 32, or 33; or, (j) the plant is a wheat plant, the gene or the transcript is a wheat DND1 gene or transcript, and the polynucleotide comprises at least 18 contiguous nucleotides that are essentially identical or essentially complementary to SEQ ID NO: 23 or 24.

A further embodiment is directed to a plant comprising an exogenous polynucleotide that comprises at least 18 contiguous nucleotides that are essentially identical or essentially complementary to a DND1 gene or transcript of the gene, wherein the exogenous polynucleotide is not operably linked to a promoter or to a viral vector, is not integrated into the chromosomal DNA of the plant, and is not found in a non-transgenic plant; and, wherein the plant exhibits an improvement in fungal disease resistance and/or nematode resistance that results from suppression of the DND1 gene. In certain embodiments, plant further comprises an organosilicone compound or a component thereof. In certain embodiments, the polynucleotide is selected from the group consisting of SEQ ID NO: 34-59, or comprises at least 18 contiguous nucleotides that are essentially identical or essentially complementary to SEQ ID NO: 1-33. In certain embodiments, the polynucleotide comprises at least 18 contiguous nucleotides that are essentially identical or essentially complementary to SEQ ID NO: 64-67. In certain embodiments: (a) the plant is a cucumber plant, the gene or the transcript is a cucumber DND1 gene or transcript, and the polynucleotide comprises at least 18 contiguous nucleotides that are essentially identical or essentially complementary to SEQ ID NO: 1, 3, 7, 11, or 19; (b) the plant is a soybean plant, the gene or the transcript is a soybean DND1 gene or transcript, and the polynucleotide molecule is selected from the group consisting of SEQ ID NO: 34-59, or the polynucleotide comprises at least 18 contiguous nucleotides that are essentially identical or essentially complementary to SEQ ID NO: 2, 4, 21, or 31; (c) the plant is a lettuce plant, the gene or the transcript is a lettuce DND1 gene or transcript, and the polynucleotide comprises at least 18 contiguous nucleotides that are essentially identical or essentially complementary to SEQ ID NO: 5 or 9; (d) the plant is a tomato plant, the gene or the transcript is a tomato DND1 gene or transcript, and the polynucleotide comprises at least 18 contiguous nucleotides that are essentially identical or essentially complementary to SEQ ID NO: 6, 10, 64, 65, 66 or 67; (e) the plant is a barley plant, the gene or the transcript is a barley DND1 gene or transcript, and the polynucleotide comprises at least 18 contiguous nucleotides that are essentially identical or essentially complementary to SEQ ID NO: 8 or 12; (f) the plant is a cotton plant, the gene or the transcript is a cotton DND1 gene or transcript, and the polynucleotide comprises at least 18 contiguous nucleotides that are essentially identical or essentially complementary to SEQ ID NO: 13, 14, 18, 25 or 26; (g) the plant is a melon plant, the gene or the transcript is a melon DND1 gene or transcript, and the polynucleotide comprises at least 18 contiguous nucleotides that are essentially identical or essentially complementary to SEQ ID NO: 15, 27, or 28; (h) the plant is a maize plant, the gene or the transcript is a maize DND1 gene or transcript, and the polynucleotide comprises at least 18 contiguous nucleotides that are essentially identical or essentially complementary to SEQ ID NO: 16, 20, 29, or 30; (i) the plant is a rice plant, the gene or the transcript is a rice DND1 gene or transcript, and the polynucleotide comprises at least 18 contiguous nucleotides that are essentially identical or essentially complementary to SEQ ID NO: 17, 22, 32, or 33; or, (j) the plant is a wheat plant, the gene or the transcript is a wheat DND1 gene or transcript, and the polynucleotide comprises at least 18 contiguous nucleotides that are essentially identical or essentially complementary to SEQ ID NO: 23 or 24.

An additional embodiment is directed to a plant part comprising an exogenous polynucleotide that comprises at least 18 contiguous nucleotides that are essentially identical or essentially complementary to a DND1 gene or transcript of the gene, wherein the exogenous polynucleotide is not operably linked to a promoter or to a viral vector and is not found in a non-transgenic plant; and, wherein the plant part exhibits an improvement in fungal disease resistance and/or nematode resistance that results from suppression of the DND1 gene. In certain embodiments, the polynucleotide is selected from the group consisting of SEQ ID NO: 34-59, or wherein the polynucleotide comprises at least 18 contiguous nucleotides that are essentially identical or essentially complementary to SEQ ID NO: 1-33. In certain embodiments, the polynucleotide comprises at least 18 contiguous nucleotides that are essentially identical or essentially complementary to SEQ ID NO: 64-67. In certain embodiments: (a) the plant is a cucumber plant, the gene or the transcript is a cucumber DND1 gene or transcript, and the polynucleotide comprises at least 18 contiguous nucleotides that are essentially identical or essentially complementary to SEQ ID NO: 1, 3, 11, or 19; (b) the plant is a soybean plant, the gene or the transcript is a soybean DND1 gene or transcript, and the polynucleotide molecule is selected from the group consisting of SEQ ID NO: 34-59, or the polynucleotide comprises at least 18 contiguous nucleotides that are essentially identical or essentially complementary to SEQ ID NO: 2, 4, 21, or 31; (c) the plant is a lettuce plant, the gene or the transcript is a lettuce DND1 gene or transcript, and the polynucleotide comprises at least 18 contiguous nucleotides that are essentially identical or essentially complementary to SEQ ID NO: 5 or 9; (d) the plant is a tomato plant, the gene or the transcript is a tomato DND1 gene or transcript, and the polynucleotide comprises at least 18 contiguous nucleotides that are essentially identical or essentially complementary to SEQ ID NO: 6, 10, 64, 65, 66 or 67; (e) the plant is a barley plant, the gene or the transcript is a barley DND1 gene or transcript, and the polynucleotide comprises at least 18 contiguous nucleotides that are essentially identical or essentially complementary to SEQ ID NO: 8 or 12; (f) the plant is a cotton plant, the gene or the transcript is a cotton DND1 gene or transcript, and the polynucleotide comprises at least 18 contiguous nucleotides that are essentially identical or essentially complementary to SEQ ID NO: 13, 14, 18, 25 or 26; (g) the plant is a melon plant, the gene or the transcript is a melon DND1 gene or transcript, and the polynucleotide comprises at least 18 contiguous nucleotides that are essentially identical or essentially complementary to SEQ ID NO: 15, 27, or 28; (h) the plant is a maize plant, the gene or the transcript is a maize DND1 gene or transcript, and the polynucleotide comprises at least 18 contiguous nucleotides that are essentially identical or essentially complementary to SEQ ID NO: 16, 20, 29, or 30; (i) the plant is a rice plant, the gene or the transcript is a rice DND1 gene or transcript, and the polynucleotide comprises at least 18 contiguous nucleotides that are essentially identical or essentially complementary to SEQ ID NO: 17, 22, 32, or 33; or, (j) the plant is a wheat plant, the gene or the transcript is a wheat DND1 gene or transcript, and the polynucleotide comprises at least 18 contiguous nucleotides that are essentially identical or essentially complementary to SEQ ID NO: 23 or 24. In certain embodiments, the plant part is a flower, meristem, ovule, stem, tuber, fruit, anther, pollen, leaf, root, or seed. In certain embodiments, the plant part is a seed. Also provided are processed plant products obtained from any of the aforementioned plant parts, wherein the processed plant products exhibit an improved attribute relative to a processed plant product of an untreated control plant and wherein the improved attribute results from the improved fungal disease resistance and/or nematode resistance. In certain embodiments, the processed product is a meal, a pulp, a feed, or a food product. Another embodiment is directed to a plant that exhibits an improvement in fungal disease resistance and/or nematode resistance, wherein the plant was topically treated with a composition that comprises: (a) at least one polynucleotide that comprises at least 18 contiguous nucleotides that are essentially identical or essentially complementary to a DND1 gene or to a transcript of the gene; and (b) a transfer agent; and, wherein the plant exhibits an improvement in fungal disease resistance and/or nematode resistance that results from suppression of the DND1 gene.

DETAILED DESCRIPTION

I. Definitions

Figure 1:
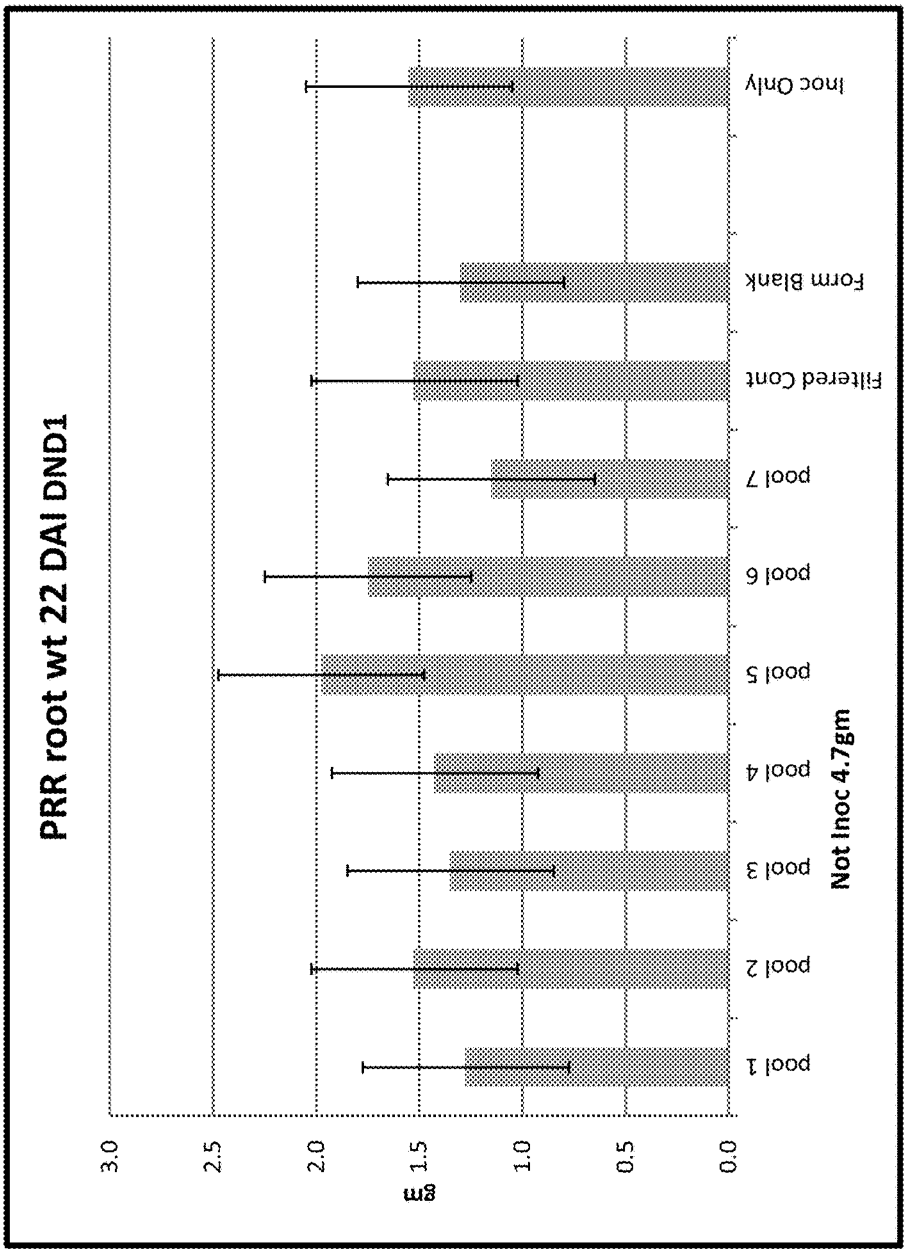
FIG. 1 shows the efficacy of certain DND1 ssDNA trigger sequences to *Phytophthora sojae* root rot (PRR).

The following definitions and methods are provided to better define the present invention and to guide those of ordinary skill in the art in the practice of the present invention. Unless otherwise noted, terms are to be understood according to conventional usage by those of ordinary skill in the relevant art.

Where a term is provided in the singular, the inventors also contemplate embodiments described by the plural of that term.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "DNA nucleotide sequence," and "DNA polynucleotide sequence" refer to the nucleotide sequence of a DNA molecule.

As used herein, the term "gene" refers to any portion of a nucleic acid that provides for expression of a transcript or encodes a transcript. A "gene" thus includes, but is not limited to, a promoter region, 5' untranslated regions, transcript encoding regions that can include intronic regions, and 3' untranslated regions.

As used herein, the terms "RNA," "RNA molecule," and "RNA polynucleotide molecule" refer to a single-stranded RNA or double-stranded RNA molecule of genomic or synthetic origin, such as, a polymer of ribonucleotide bases that comprise single or double stranded regions.

Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, a "plant surface" refers to any exterior portion of a plant. Plant surfaces thus include, but are not limited to, the surfaces of flowers, stems, tubers, fruit, anthers, pollen, leaves, roots, or seeds. A plant surface can be on a portion of a plant that is attached to other portions of a plant or on a portion of a plant that is detached from the plant.

As used herein, the phrase "polynucleotide is not operably linked to a promoter" refers to a polynucleotide that is not covalently linked to a polynucleotide promoter sequence that is specifically recognized by either a DNA dependent RNA polymerase II protein or by a viral RNA dependent RNA polymerase in such a manner that the polynucleotide will be transcribed by the DNA dependent RNA polymerase II protein or viral RNA dependent RNA polymerase. A polynucleotide that is not operably linked to a promoter can be transcribed by a plant RNA dependent RNA polymerase.

As used herein, any polynucleotide sequences of SEQ ID NO: 1-33, 34-63 and 64-67, though displayed in the sequence listing in the form of ssDNA, encompass all other polynucleotide forms such as dsDNA equivalents, ssDNA equivalents, ssRNA equivalents, ssRNA complements, dsRNA, and ssDNA complements.

As used herein, a first nucleic-acid sequence is "operably" connected or "linked" with a second nucleic acid sequence when the first nucleic acid sequence is placed in a functional relationship with the second nucleic acid sequence. For instance, a promoter is operably linked to an RNA and/or protein-coding sequence if the promoter provides for transcription or expression of the RNA or coding sequence. Generally, operably linked DNA sequences are contiguous and, where necessary to join two protein-coding regions, are in the same reading frame.

As used herein, the phrase "organosilicone preparation" refers to a liquid comprising one or more organosilicone compounds, wherein the liquid or components contained therein, when combined with a polynucleotide in a composition that is topically applied to a target plant surface, enable the polynucleotide to enter a plant cell. Exemplary organosilicone preparations include, but are not limited to, preparations marketed under the trade names "Silwet®" or "BREAK-THRU®" and preparations provided in Table 1. In certain embodiments, an organosilicone preparation can enable a polynucleotide to enter a plant cell in a manner permitting a polynucleotide suppression of target gene expression in the plant cell.

As used herein, the phrase "provides for an improvement in fungal disease resistance and/or nematode resistance" refers to any measurable increase in a plants resistance to fungal- and/or nematode-induced damage. In certain embodiments, an improvement in fungal disease resistance and/or nematode resistance in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants.

As used herein, the phrase "provides for a reduction", when used in the context of a transcript or a protein in a plant or plant part, refers to any measurable decrease in the level of transcript or protein in a plant or plant part. In certain embodiments, a reduction of the level of a transcript or protein in a plant or plant part can be determined in a comparison to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the phrase "wherein said plant does not comprise a transgene" refers to a plant that lacks either a DNA molecule comprising a promoter that is operably linked to a polynucleotide or a recombinant viral vector.

As used herein, the phrase "suppressing expression" or "suppression", when used in the context of a gene, refers any measurable decrease in the amount and/or activity of a product encoded by the gene. Thus, expression of a gene can be suppressed when there is a reduction in levels of a transcript from the gene, a reduction in levels of a protein encoded by the gene, a reduction in the activity of the transcript from the gene, a reduction in the activity of a protein encoded by the gene, any one of the preceding conditions, or any combination of the preceding conditions. In this context, the activity of a transcript includes, but is not limited to, its ability to be translated into a protein and/or to exert any RNA-mediated biologic or biochemical effect. In this context, the activity of a protein includes, but is not limited to, its ability to exert any protein-mediated biologic or biochemical effect. In certain embodiments, a suppression of gene expression in a plant or plant part can be determined in a comparison of gene product levels or activities in a treated plant to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, the term "liquid" refers to both homogeneous mixtures such as solutions and non-homogeneous mixtures such as suspensions, colloids, micelles, and emulsions.

II. Overview

Provided herein are certain methods and polynucleotide compositions that can be applied to living plant cells/tissues to suppress expression of target genes and that provide improved fungal disease resistance and/or nematode resistance to a crop plant. Also provided herein are plants and plant parts exhibiting fungal disease resistance and/or nematode resistance as well as processed products of such plants or plant parts. The compositions may be topically applied to the surface of a plant, such as to the surface of a leaf, and include a transfer agent. Aspects of the method can be applied to various crops, for example, including but not limited to: i) row crop plants including, but are not limited to, corn, barley, sorghum, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) that include fruit trees and plants. Fruit trees produced by such processes include, but are not limited to, citrus and apple trees. Plants produced by such processes include, but are not limited to, avocados, tomatoes, eggplant, cucumber, melons, watermelons, and grapes as well as various ornamental plants.

Without being bound by theory, the compositions and methods as described herein are believed to operate through one or more of the several natural cellular pathways involved in RNA-mediated gene suppression as generally described in Brodersen and Voinnet (2006), *Trends Genetics,* 22:268-280; Tomari and Zamore (2005) *Genes & Dev.,* 19:517-529; Vaucheret (2006) *Genes Dev.,* 20:759-771; Meins et al. (2005) *Annu. Rev. Cell Dev. Biol.,* 21:297-318; and Jones-Rhoades et al. (2006) *Annu. Rev. Plant Biol.,* 57:19-53. RNA-mediated gene suppression generally involves a double-stranded RNA (dsRNA) intermediate that is formed intra-molecularly within a single RNA molecule or inter-molecularly between two RNA molecules. This longer dsRNA intermediate is processed by a ribonuclease of the RNAase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 to 24 base pairs (See, Hamilton et al. (2002) *EMBO* 1, 21:4671-4679).

Polynucleotides

As used herein, "polynucleotide" refers to a DNA or RNA molecule containing multiple nucleotides and generally refers both to "oligonucleotides" (a polynucleotide molecule of 18-25 nucleotides in length) and longer polynucleotides of 26 or more nucleotides. Embodiments include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments include compositions including oligonucleotides, polynucleotides, or a mixture of both, including: RNA or DNA or RNA/DNA hybrids or chemically modified oligonucleotides or polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g., fluorescein or rhodamine) or other label (e. g., biotin).

Polynucleotides can be single- or double-stranded RNA, single- or double-stranded DNA, double-stranded DNA/RNA hybrids, and modified analogues thereof. In certain embodiments, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand will comprise at least 18 nucleotides that are essentially complementary to the target gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain embodiments, the polynucleotides can be operably linked to a promoter—generally a promoter functional in a plant, for example, a pol II promoter, a pol III promoter, a pol IV promoter, or a pol V promoter.

In some embodiments, the polynucleotide molecules are designed to modulate expression by inducing regulation or suppression of an endogenous gene in a plant and are designed to have a nucleotide sequence essentially identical or essentially complementary to the nucleotide sequence of an endogenous gene of a plant or to the sequence of RNA transcribed from an endogenous gene of a plant, which can be coding sequence or non-coding sequence. These effective polynucleotide molecules that modulate expression are referred to herein as "a trigger, or triggers". By "essentially identical" or "essentially complementary" it is meant that the trigger polynucleotides (or at least one strand of a double-stranded polynucleotide) have sufficient identity or complementarity to the endogenous gene or to the RNA transcribed from the endogenous gene (e.g. the transcript) to suppress expression of the endogenous gene (e.g. to effect a reduction in levels or activity of the gene transcript and/or encoded protein). Polynucleotides of the methods and compositions provided herein need not have 100 percent identity to a complementarity to the endogenous gene or to the RNA transcribed from the endogenous gene (i.e. the transcript) to suppress expression of the endogenous gene (i.e. to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g. the transcript). In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g. the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

In certain embodiments, polynucleotides used in the methods and compositions provided herein can be essentially identical or essentially complementary to any of: i) conserved regions of DND1 genes of both monocot and dicot plants; ii) conserved regions of DND1 genes of monocot plants; or iii) conserved regions of DND1 genes of dicot plants. Such polynucleotides that are essentially identical or essentially complementary to such conserved regions can be used to improve fungal disease resistance and/or nematode disease resistance by suppressing expression of DND1 genes in any of: i) both dicot and monocot plants, including, but not limited to, maize, barley, wheat, sorghum, rice, cucumber, pea, *Medicago* sp., soybean, pepper, tomato, lettuce, cotton, melon, and grape; ii) monocot plants, including, but not limited to, maize, barley, wheat, sorghum, and rice, and; or iii) dicot plants, including, but not limited to, cucumber, pea, *Medicago* sp., soybean, pepper, tomato, lettuce, cotton, melon, and grape.

Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to RNA transcribed from the target gene (e.g. the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to RNA transcribed from the target gene (e.g. the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. Nucleic Acids Research, 2005, Vol. 33, No. 5 1671-1677. In certain exemplary embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e. positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of DND1 expression or appearance of fungal disease resistance and/or nematode resistance.

In certain embodiments, polynucleotide molecules are designed to have 100 percent sequence identity with or complementarity to one allele or one family member of a given target gene coding or non-coding sequence of a DND1 target gene. In other embodiments, the polynucleotide molecules are designed to have 100 percent sequence identity with or complementarity to multiple alleles or family members of a given DND1 target gene. In certain embodiments, the polynucleotide can thus comprise at least 18 contiguous nucleotides that are identical or complementary to SEQ ID NO: 1-33. In certain embodiments, the polynucleotide comprises at least 18 contiguous nucleotides that are essentially identical or essentially complementary to SEQ ID NO: 1-33. In certain embodiments, the polynucleotide comprises at least 18 contiguous nucleotides that are identical or complementary to SEQ ID NO: 64-67. In certain embodiments, the polynucleotide comprises at least 18 contiguous nucleotides that are essentially identical or essentially complementary to SEQ ID NO: 64-67.

In certain embodiments, polynucleotide compositions and methods provided herein typically effect regulation or modulation (e. g., suppression) of gene expression during a period during the life of the treated plant of at least 1 week or longer and typically in systemic fashion. For instance, within days of treating a plant leaf with a polynucleotide composition as described herein, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or a transcript encoding a DND1 gene of the plant are provided, whereby expression of the gene in said plant or progeny thereof is systemically suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence (i. e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

Tiling

Polynucleotide trigger molecules can be identified by "tiling" gene targets in random length fragments, e.g. 200-300 polynucleotides in length, with partially overlapping regions, e.g. 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

Polynucleotides fragments are designed along the length of the full length coding and untranslated regions of a DND1 gene or family member as contiguous overlapping fragments of 200-300 polynucleotides in length or fragment lengths representing a percentage of the target gene. These fragments are applied topically (as sense or anti-sense ssDNA or ssRNA, dsRNA, or dsDNA) to determine the relative effectiveness in providing the yield/quality phenotype. Fragments providing the desired activity may be further subdivided into 50-60 polynucleotide fragments which are evaluated for providing the yield/quality phenotype. The 50-60 base fragments with the desired activity may then be further subdivided into 19-30 base fragments which are evaluated for providing the yield/quality phenotype. Once relative effectiveness is determined, the fragments are utilized singly, or in combination in one or more pools to determine effective trigger composition or mixture of trigger polynucleotides for providing the yield/quality phenotype.

Coding and/or non-coding sequences of gene families in the crop of interest are aligned and 200-300 polynucleotide fragments from the least homologous regions amongst the aligned sequences are evaluated using topically applied polynucleotides (as sense or anti-sense ssDNA or ssRNA, dsRNA, or dsDNA) to determine their relative effectiveness in providing the yield/quality phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the yield/quality phenotype. Once relative effectiveness is determined, the fragments are utilized singly, or again evaluated in combination with one or more other fragments to determine the trigger composition or mixture of trigger polynucleotides for providing the yield/quality phenotype.

Coding and/or non-coding sequences of gene families in the crop of interest are aligned and 200-300 polynucleotide fragments from the most homologous regions amongst the aligned sequences are evaluated using topically applied polynucleotides (as sense or anti-sense ssDNA or ssRNA, dsRNA, or dsDNA) to determine their relative effectiveness in inducing the yield/quality phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the yield/quality phenotype. Once relative effectiveness is determined, the fragments may be utilized singly, or in combination with one or more other fragments to determine the trigger composition or mixture of trigger polynucleotides for providing the yield/quality phenotype.

Also, provided herein are methods for identifying a preferred polynucleotide for improving fungal disease and/or nematode resistance in a plant. Populations of candidate polynucleotides that are essentially identical or essentially complementary to a DND1 gene or transcript of the gene can be generated by a variety of approaches, including but not limited to, any of the tiling, least homology, or most homology approaches provided herein. Such populations of polynucleotides can also be generated or obtained from any of the polynucleotides or genes provided herewith in SEQ ID NO: 1-59. Such populations of polynucleotides can also be generated or obtained from any of the polynucleotides provided herewith in SEQ ID NO: 64-67. Such populations of polynucleotides can also be generated or obtained from any genes that are orthologous to the genes provided herewith in SEQ ID NO: 1-33. Such populations of polynucleotides can also be generated or obtained from any genes that encode orthologous proteins. Such polynucleotides can be topically applied to a surface of plants in a composition comprising at least one polynucleotide from said population and a transfer agent to obtain treated plants. Treated plants that exhibit suppression of the DND1 gene and/or exhibit an improvement fungal disease and/or nematode resistance are identified, thus identifying a preferred polynucleotide that improves improving fungal disease and/or nematode resistance in a plant. Suppression of the gene can be determined by any assay for the levels and/or activity of a gene product (i.e. transcript or protein). Suitable assays for transcripts include, but are not limited to, semi-quantitative or quantitative reverse transcriptase PCR® (qRT-PCR) assays. Suitable assays for proteins include, but are not limited to, semi-quantitative or quantitative immunoassays, biochemical activity assays, or biological activity assays. In certain embodiments, the polynucleotides can be applied alone. In other embodiments, the polynucleotides can be applied in pools of multiple polynucleotides. When a pool of polynucleotides provides for suppression of the DND1 gene and/or an improvement in fungal disease resistance and/or nematode disease resistance are identified, the pool can be de-replicated and retested as necessary or desired to identify one or more preferred polynucleotide(s) that improves fungal disease resistance and/or nematode disease resistance in a plant.

Methods of making polynucleotides are well known in the art. Such methods of making polynucleotides can include in vivo biosynthesis, in vitro enzymatic synthesis, or chemical synthesis. In certain embodiments, RNA molecules can be made by either in vivo or in vitro synthesis from DNA templates where a suitable promoter is operably linked to the polynucleotide and a suitable DNA-dependent RNA polymerase is provided. DNA-dependent RNA polymerases include, but are not limited to, *E. coli* or other bacterial RNA polymerases as well as the bacteriophage RNA polymerases such as the T7, T3, and SP6 RNA polymerases. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end that encodes a bacteriophage T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score (Reynolds et al. *Nature Biotechnology* 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

While there is no upper limit on the concentrations and dosages of polynucleotide molecules that can be useful in the methods and compositions provided herein, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotide molecules is about 1 nanomole (nmol) of polynucleotide molecules per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide are applied. In certain embodiments, about 0.5 nmol to about 2 nmol of a dsRNA is applied. In certain embodiments, a composition containing about 0.5 to about 2.0 mg/mL, or about 0.14 mg/mL of dsRNA or ssDNA (21-mer) is applied. In certain embodiments, a composition of about 0.5 to about 1.5 mg/mL of a long dsRNA polynucleotide (i.e. about 50 to about 200 or more nucleotides) is applied. In certain embodiments, about 1 nmol to about 5 nmol of a dsRNA is applied to a plant. In certain embodiments, the polynucleotide composition as topically applied to the plant contains the at least one polynucleotide at a concentration of about 0.01 to about 10 milligrams per milliliter, or about 0.05 to about 2 milligrams per milliliter, or about 0.1 to about 2 milligrams per milliliter. In certain embodiments, a composition of about 0.5 to about 1.5 mg/mL of a long dsRNA polynucleotide (i.e. about 50 to about 200 or more nucleotides) is applied. Very large plants, trees, or vines may require correspondingly larger amounts of polynucleotides. When using long dsRNA molecules that can be processed into multiple oligonucleotides, lower concentrations can be used. To illustrate certain embodiments, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions as described herein are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e. g., seeds, leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the 9$^{th}$ Compendium of Herbicide Adjuvants, publicly available on the worldwide web (internet) at herbicide.adjuvants.com can be used, e. g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL. REG. NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided. In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1% by weight (wt percent) is used or provided.

In certain embodiments, any of the commercially available organosilicone preparations provided in the following Table 1 can be used as transfer agents in a polynucleotide composition. In certain embodiments where an organosilicone preparation of Table 1 is used as a pre-spray treatment of plant leaves or other surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation of Table 1 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

TABLE 1

Exemplary organosilicone preparations

| Name | CAS number | Manufacturer [1, 2] |
|---|---|---|
| BREAK-THRU ® S 321 | na | Evonik Industries AG |
| BREAK-THRU ® S 200 | 67674-67-3 | Evonik Industries AG |
| BREAK-THRU ® OE 441 | 68937-55-3 | Evonik Industries AG |
| BREAK-THRU ® S 278 | 27306-78-1 | Evonik Goldschmidt |
| BREAK-THRU ® S 243 | na | Evonik Industries AG |
| Silwet ® L-77 | 27306-78-1 | Momentive Performance Materials |
| Silwet ® HS 429 | na | Momentive Performance Materials |
| Silwet ® HS 312 | na | Momentive Performance Materials |
| BREAK-THRU ® S 233 | 134180-76-0 | Evonik Industries AG |
| Silwet ® HS 508 | | Momentive Performance Materials |
| Silwet ® HS 604 | | Momentive Performance Materials |

[1] Evonik Industries AG, Essen, Germany
[2] Momentive Performance Materials, Albany, New York Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

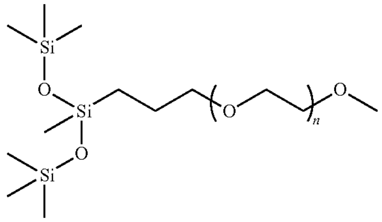

(Compound I: polyalkyleneoxide heptamethyltrisiloxane, average n = 7.5).

One organosilicone compound believed to be ineffective comprises the formula:

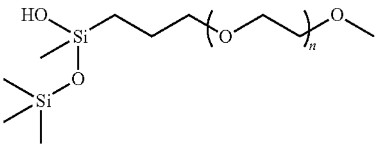

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, the polynucleotide compositions that comprise an organosilicone preparation can comprise a salt such as ammonium chloride, tetrabutylphosphonium bromide, and/or ammonium sulfate. Ammonium chloride, tetrabutylphosphonium bromide, and/or ammonium sulfate can be provided in the polynucleotide composition at a concentration of about 0.5% to about 5% (w/v). An ammonium chloride, tetrabutylphosphonium bromide, and/or ammonium sulfate concentration of about 1% to about 3%, or about 2% (w/v) can also be used in the polynucleotide compositions that comprise an organosilicone preparation. In certain embodiments, the polynucleotide compositions can comprise an ammonium salt at a concentration greater or equal to 300 millimolar. In certain embodiments, the polynucleotide compositions that comprise an organosilicone preparation can comprise ammonium sulfate at concentrations from about 80 to about 1200 mM or about 150 mM to about 600 mM.

In certain embodiments, the polynucleotide compositions can also comprise a phosphate salt. Phosphate salts used in the compositions include, but are not limited to, calcium, magnesium, potassium, or sodium phosphate salts. In certain embodiments, the polynucleotide compositions can comprise a phosphate salt at a concentration of at least about 5 millimolar, at least about 10 millimolar, or at least about 20 millimolar. In certain embodiments, the polynucleotide compositions will comprise a phosphate salt in a range of about 1 mM to about 25 mM or in a range of about 5 mM to about 25 mM. In certain embodiments, the polynucleotide compositions can comprise sodium phosphate at a concentration of at least about 5 millimolar, at least about 10 millimolar, or at least about 20 millimolar. In certain embodiments, the polynucleotide compositions can comprise sodium phosphate at a concentration of about 5 millimolar, about 10 millimolar, or about 20 millimolar. In certain embodiments, the polynucleotide compositions will comprise a sodium phosphate salt in a range of about 10 mM to about 160 mM or in a range of about 20 mM to about 40 mM. In certain embodiments, the polynucleotide compositions can comprise a sodium phosphate buffer at a pH of about 6.8.

In certain embodiments, other useful transfer agents or adjuvants to transfer agents that can be used in polynucleotide compositions provided herein include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the polynucleotide compositions that comprise a transfer agent are formulated with counter-ions or other molecules that are known to associate with nucleic acid molecules. Illustrative examples include, but are not limited to, tetraalkyl ammonium ions, trialkyl ammonium ions, sulfonium ions, lithium ions, and polyamines such as spermine, spermidine, or putrescine. In certain embodiments, the polynucleotide compositions are formulated with a non-polynucleotide herbicide. Non-polynucleotide herbicidal molecules include, but are not limited to, glyphosate, auxin-like benzoic acid herbicides including dicamba, chloramben and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrionogen oxidase inhibitors, and 4-hydroxyphenyl-pyruvate-dioxygenase inhibiting herbicides.

In certain embodiments, the polynucleotides used in the compositions that are essentially identical or essentially complementary to the DND1 target gene or transcript will comprise the predominant nucleic acid in the composition. Thus in certain embodiments, the polynucleotides that are essentially identical or essentially complementary to the target gene or transcript will comprise at least about 50%, 75%, 95%, 98%, or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

Polynucleotides comprising ssDNA, dsDNA, ssRNA, dsRNA, or RNA/DNA hybrids that are essentially identical or complementary to certain plant target genes or transcripts and that can be used in compositions containing transfer agents that include, but are not limited to, organosilicone preparations, to suppress those target genes when topically applied to plants are disclosed in co-assigned U.S. patent application Ser. No. 13/042,856. Various polynucleotide herbicidal molecules, compositions comprising those polynucleotide herbicidal molecules and transfer agents that include, but are not limited to, organosilicone preparations, and methods whereby herbicidal effects are obtained by the topical application of such compositions to plants are also disclosed in co-assigned U.S. patent application Ser. No. 13/042,856, and those polynucleotide herbicidal molecules, compositions, and methods are incorporated herein by reference in their entireties. Genes encoding proteins that can provide tolerance to an herbicide and/or that are targets of a herbicide are collectively referred to herein as "herbicide target genes". Herbicide target genes include, but are not limited to, a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase, a cellulose synthase, a beta tubulin, and a serine hydroxymethyltransferase gene. The effects of applying certain compositions comprising polynucleotides that are essentially identical or complementary to certain herbicide target genes and transfer agents on plants containing the herbicide target genes was shown to be potentiated or enhanced by subsequent application of an herbicide that targets the same gene as the polynucleotide in co-assigned U.S. patent application Ser. No. 13/042,856. For example, compositions comprising polynucleotides targeting the EPSPS herbicide target gene were potentiated by glyphosate in experiments disclosed in co-assigned U.S. patent application Ser. No. 13/042,856.

In certain embodiments of the compositions and methods disclosed herein, the composition comprising a polynucleotide and a transfer agent can thus further comprise a second polynucleotide comprising at least 19 contiguous nucleotides that are essentially identical or essentially complementary to a transcript to a protein that confers resistance to a herbicide. In certain embodiments, the second polynucleotide does not comprise a polynucleotide that is essentially identical or essentially complementary to a transcript encoding a protein of a target plant that confers resistance to said herbicidal molecule. Thus, in an exemplary and non-limiting embodiment, the second polynucleotide could be essentially identical or essentially complementary to a transcript encoding a protein that confers resistance to a herbicide in a weed (such as an EPSPS encoding transcript) but would not be essentially identical or essentially complementary to a transcript encoding a protein that confers resistance to that same herbicide in a crop plant.

In certain embodiments, the polynucleotide compositions that comprise a transfer agent can comprise glycerin. Glycerin can be provided in the composition at a concentration of about 0.1% to about 1% (w/v or v/v). A glycerin concentration of about 0.4% to about 0.6%, or about 0.5% (w/v or v/v) can also be used in the polynucleotide compositions that comprise a transfer agent.

In certain embodiments, the polynucleotide compositions that comprise a transfer agent can further comprise organic solvents. Such organic solvents include, but are not limited to, DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions).

In certain embodiments, the polynucleotide compositions that comprise a transfer agent can further comprise naturally derived or synthetic oils with or without surfactants or emulsifiers. Such oils include, but are not limited to, plant-sourced oils, crop oils (such as those listed in the 9th Compendium of Herbicide Adjuvants, publicly available on line at www.herbicide.adjuvants.com), paraffinic oils, polyol fatty acid esters, or oils with short-chain molecules modified with amides or polyamines such as polyethyleneimine or N-pyrrolidine.

In some embodiments, methods include one or more applications of the composition comprising a polynucleotide and a transfer agent or one or more effective components contained therein. In certain embodiments of the methods, one or more applications of a transfer agent or one or more effective components contained therein can precede one or more applications of the composition comprising a polynucleotide and a transfer agent. In embodiments where a transfer agent and/or one or more effective molecules contained therein is used either by itself as a pre-treatment or as part of a composition that includes a polynucleotide, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

Compositions and methods as described herein are useful for modulating or suppressing the expression of an endogenous DND1 target gene or transgenic DND1 target gene in a plant cell or plant. In certain embodiments of the methods and compositions provided herein, expression of DND1 target genes can be suppressed completely, partially and/or transiently to result in an improvement in fungal disease resistance and/or nematode resistance. In various embodiments, a DND1 target gene includes coding (protein-coding or translatable) sequence, non-coding (non-translatable) sequence, or both coding and non-coding sequence. Compositions as described herein can include polynucleotides and oligonucleotides designed to target multiple DND1 genes, or multiple segments of one or more DND1 genes. The target gene can include multiple consecutive segments of a target DND1 gene, multiple non-consecutive segments of a DND1 target gene, multiple alleles of a target gene, or multiple DND1 target genes from one or more species. DND1 target genes include, but are not limited to, the endogenous DND1 plant genes of SEQ ID NO: 1-33. DND1 target genes include, but are not limited to, DND1 plant genes that encode orthologous proteins or essentially homologous proteins having between about 1, 2, 3, 4, 5, 6, 7, 8, 9, or 10 amino acid substitutions, deletions, or insertions.

Target genes and plants containing those target genes can be obtained from: i) row crop plants including, but are not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants that include, but are not limited to, citrus, apples, avocados, tomatoes, eggplant, cucumber, melons, watermelons, and grapes as well as various ornamental plants. Such row crop, vegetable, culinary, fruit, tree, or ornamental plants exhibiting improvements in fungal disease resistance and/or nematode resistance that result from suppressing DND1 gene expression are provided herein. Such row crop, vegetable, culinary, fruit, tree, or ornamental plant parts or processed plant products exhibiting improvements in fungal disease resistance and/or nematode resistance that result from suppressing DND1 gene expression are also provided herein. Such plant parts can include, but are not limited to, flowers, stems, tubers, fruit, anthers, meristems, ovules, pollen, leaves, or seeds. Such processed plant products obtained from the plant parts can include, but are not limited to, a meal, a pulp, a feed, or a food product.

In some embodiments, a method for modulating or suppressing expression of an DND1 gene in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the DND1 target gene in either anti-sense or sense orientation, whereby the polynucleotide molecules permeate the interior of the plant and induce modulation of the target gene is provided. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the DND1 target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches. In certain embodiments where the polynucleotide used in the composition comprises a promoter sequence essentially identical to, or essentially complementary to, at least 18 contiguous nucleotides of the promoter of the endogenous target gene, the promoter sequence of the polynucleotide is not operably linked to another sequence that is transcribed from the promoter sequence.

Compositions comprising a polynucleotide and a transfer agent provided herein can be topically applied to a plant or plant part by any convenient method, e.g., spraying or coating with a powder, or with a liquid composition comprising any of an emulsion, suspension, or solution. Such topically applied sprays or coatings can be of either all or of any a portion of the surface of the plant or plant part. Similarly, compositions that comprise a transfer agent or other pre-treatment can in certain embodiments be applied to the plant or plant part by any convenient method, e. g., spraying or wiping a solution, emulsion, or suspension. Compositions comprising a polynucleotide and a transfer agent provided herein can be topically applied to plant parts that include, but are not limited to, flowers, stems, tubers, meristems, ovules, fruit, anthers, pollen, leaves, or seeds.

Application of compositions comprising a polynucleotide and a transfer agent to seeds is specifically provided herein. Seeds can be contacted with such compositions by spraying, misting, immersion, and the like.

In certain embodiments, application of compositions comprising a polynucleotide and a transfer agent to plants, plant parts, or seeds in particular can provide for an improvement in fungal disease resistance and/or nematode resistance in progeny plants, plant parts, or seeds derived from those treated plants, plant parts, or seeds. In certain embodiments, progeny plants, plant parts, or seeds derived from those treated plants, plant parts, or seeds will exhibit an improvement in fungal disease resistance and/or nematode resistance that result from suppressing expression of a DND1 gene. In certain embodiments, the methods and compositions provided herein can provide for an improvement in fungal disease resistance and/or nematode resistance in progeny plants or seeds as a result of epigenetically inherited suppression of DND1 expression. In certain embodiments, such progeny plants exhibit an improvement in fungal disease resistance and/or nematode resistance from epigenetically inherited suppression of DND1 gene expression that is not caused by a transgene where the polynucleotide is operably linked to a promoter, a viral vector, or a copy of the polynucleotide that is integrated into a non-native location in the chromosomal DNA of the plant. Without seeking to be limited by theory, progeny plants or seeds derived from those treated plants, plant parts, or seeds can exhibit an improvement in an improvement in fungal disease resistance and/or nematode resistance through an epigenetic mechanism that provides for propagation of an epigenetic condition where suppression of DND1 gene expression occurs in the progeny plants, plant parts, or plant seeds.

In certain embodiments, progeny plants or seeds exhibiting an improvement in fungal disease resistance and/or nematode resistance as a result of epigenetically inherited suppression of DND1 gene expression can also exhibit increased methylation, and in particular, increased methylation of cytosine residues, in the endogenous DND1 gene of the plant. Plant parts, including seeds, of the progeny plants that exhibit an improvement in an improvement in fungal disease resistance and/or nematode resistance as a result of epigenetically inherited suppression of DND1 gene expression, can also in certain embodiments exhibit increased methylation, and in particular, increased methylation of cytosine residues, in the endogenous DND1 gene. In certain embodiments, DNA methylation levels in DNA encoding the endogenous DND1 gene can be compared in plants that exhibit an improvement in fungal disease resistance and/or nematode resistance and control plants that do not exhibit an improvement in fungal disease resistance and/or nematode resistance to correlate the presence of the an improvement in fungal disease resistance and/or nematode resistance to epigenetically inherited suppression of DND1 gene expression and to identify plants that comprise the epigenetically inherited improvement in fungal disease resistance and/or nematode resistance.

Various methods of spraying compositions on plants or plant parts can be used to topically apply to a plant surface a composition comprising a polynucleotide that comprises a transfer agent. In the field, a composition can be applied with a boom that extends over the crops and delivers the composition to the surface of the plants or with a boomless sprayer that distributes a composition across a wide area. Agricultural sprayers adapted for directional, broadcast, or banded spraying can also be used in certain embodiments. Sprayers adapted for spraying particular parts of plants including, but not limited to, leaves, the undersides of leaves, flowers, stems, male reproductive organs such as tassels, meristems, pollen, ovules, and the like can also be used. Compositions can also be delivered aerially, such as by a crop dusting airplane. In certain embodiments, the spray can be delivered with a pressurized backpack sprayer calibrated to deliver the appropriate rate of the composition. In certain embodiments, such a backpack sprayer is a carbon dioxide pressurized sprayer with a 11015 flat fan or equivalent spray nozzle with a customized single nozzle assembly (to minimize waste) at a spray pressure of about 0.25 MPa and/or any single nozzle sprayer providing an effective spray swath of 60 cm above the canopy of 3 to 12 inch tall growing plants can be used. Plants in a greenhouse or growth chamber can be treated using a track sprayer or laboratory sprayer with a 11001XR or equivalent spray nozzle to deliver the sample solution at a determined rate. An exemplary and non-limiting rate is about 140 L/ha at about 0.25 MPa pressure.

In certain embodiments, it is also contemplated that a plant part can be sprayed with the composition comprising a polynucleotide that comprises a transfer agent. Such plant parts can be sprayed either pre- or post-harvest to provide for an improvement in fungal disease resistance and/or nematode resistance in the plant part that results from suppression of DND1 gene expression. Compositions can be topically applied to plant parts attached to a plant by a spray as previously described. Compositions can be topically applied to plant parts that are detached from a plant by a spray as previously described or by an alternative method. Alternative methods for applying compositions to detached parts include, but are not limited to, passing the plant parts through a spray by a conveyor belt or trough, or immersing the plant parts in the composition.

Compositions comprising polynucleotides and transfer agents can be applied to plants or plant parts at one or more developmental stages as desired and/or as needed. Application of compositions to pre-germination seeds and/or to post-germination seedlings is provided in certain embodiments. Seeds can be treated with polynucleotide compositions provided herein by methods including, but not limited to, spraying, immersion or any process that provides for coating, imbibition, and/or uptake of the polynucleotide composition by the seed. Seeds can be treated with polynucleotide compositions using seed batch treatment systems or continuous flow treatment systems. Seed coating systems are at least described in U.S. Pat. Nos. 6,582,516, 5,891,246, 4,079,696, and 4,023,525. Seed treatment can also be effected in laboratory or commercial scale treatment equipment such as a tumbler, a mixer, or a pan granulator. A polynucleotide composition used to treat seeds can contain one or more other desirable components including, but not limited to liquid diluents, binders to serve as a matrix for the polynucleotide, fillers for protecting the seeds during stress conditions, and plasticizers to improve flexibility, adhesion and/or spreadability of the coating. In addition, for oily polynucleotide compositions containing little or no filler, drying agents such as calcium carbonate, kaolin or bentonite clay, perlite, diatomaceous earth or any other adsorbent material can be added. Use of such components in seed treatments is described in U.S. Pat. No. 5,876,739. Additional ingredients can be incorporated into the polynucleotide compositions used in seed treatments. Such ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like that can be combined with compositions comprising a polynucleotide and a transfer agent. Further ingredients used in compositions that can be applied to seeds can be found in McCutcheon's, vol. 1, "Emulsifiers and Detergents," MC Publishing Company, Glen Rock, N.J., U.S.A., 1996 and in McCutcheon's, vol. 2, "Functional Materials," MC Publishing Company, Glen Rock, N.J., U.S.A., 1996. Methods of applying compositions to seeds and pesticidal compositions that can be used to treat seeds are described in U.S. Patent Application publication 20080092256, which is incorporated herein by reference in its entirety.

Application of the compositions in early, mid-, and late vegetative stages of plant development is provided in certain embodiments. Application of the compositions in early, mid- and late reproductive stages is also provided in certain embodiments. Application of the compositions to plant parts at different stages of maturation is also provided.

The following examples are included to demonstrate examples of certain embodiments. It should be appreciated by those of skill in the art that many changes can be made in the specific embodiments that are disclosed and still obtain a like or similar result without departing from the spirit and scope of the invention.

EXAMPLES

Example 1. DND1 DNA Polynucleotides Give an Effect on Soybean for Efficacy to *Phytophtora sojae* Root Rot (PRR)

DND1 ssDNA triggers (Table 2) were tested on soybean (cultivar Williams 82) for efficacy to *Phytophthora sojae* (PRR). Four reps were performed per treatment. Triggers were applied as pools of 20 nm of oligos in 0.2% Silwet, 5 mM NaPO4 and 1% AMS in Gibco Ultra Pure water. There were 3 to 4 20 nm triggers applied as a pool for a final concentration of 60 to 80 nm (Table 3). 50 μL it was applied to each plant; 25 μL per each unifoliate (VC-V1) 12 days after seeding. One day after trigger application the plants were inoculated with *Phytophtora sojae* as follows: two 8 mm plugs containing PRR inoculum harvested from V8+cef agar plates were ground in a Cuisinart blender and pushed through a syringe. Four agar plates total were used in the inoculation. Of the four plates, two were started 6 days before use and the other two plates were started 13 days before use. One plug each for the inoculation came from the 6 day old plate and the second plug was from the older (13 day) plate. Plants were harvested 22 days after inoculation; roots were weighed and rated for disease. Disease development was observed, as the non-inoculated roots were 3 times larger than the inoculated control. None of the oligo pool treatments were statistically different than the formulation blank or the filtered control treatment. However, pool 5 roots weighed 52% more than the formulation blank and 32% larger than the filtered control roots. (Error bars are large enough that these roots were not statistically different.) Roots were also rated for disease using a 0 to 4 scale; this is a subjective rating scale.

Rating scale: 0=no disease; 1=10% browning of roots; 2=25% browning or roots; 3=50% browning of roots; 4=80% browning of roots.

As shown in FIG. 1: pool 5 had less disease than all the other inoculated treatments; roots in pool 5 treated plants did not have as much browning and had more secondary roots. This is the first time that a direct correlation was observed between bigger roots and less disease in testing triggers to confer efficacy against PRR.

TABLE 2

DND1 ssDNA trigger sequences

| Sequences | Sequence listing | gene |
|---|---|---|
| GGAGAGAGGAGAAGGTGTTGTGCATcoding | SEQ ID NO: 34 | DND1 |
| CCAGCCCTCCGTCCATGTACAAGCAcoding | SEQ ID NO: 35 | DND1 |
| ATGTAGCCTGTGACTTTTTGCATTCcoding | SEQ ID NO: 36 | DND1 |
| AGCGACTCCCGCGATACGTACGCCAcoding | SEQ ID NO: 37 | DND1 |
| CACCCTGTCACAGATGTTGTCAAGAcoding | SEQ ID NO: 38 | DND1 |
| AAGGCACCATGAAAGCAGCTCGTCAcoding | SEQ ID NO: 39 | DND1 |
| ATTCAAGGTGGTCATGTGGCCTTATcoding | SEQ ID NO: 40 | DND1 |
| GAGTAGAAGAACAGCGGGTCTATCGcoding | SEQ ID NO: 41 | DND1 |
| ATCACGAATGCGTCGAACCAGAATCcoding | SEQ ID NO: 42 | DND1 |
| TGACAGGAAGTGCCCATTGGTAGATcoding | SEQ ID NO: 43 | DND1 |
| GCAGCATATTGCAAGAGCCTGCGTTcoding | SEQ ID NO: 44 | DND1 |
| TGCTGCCCATCTCTGACGTTCAAAAcoding | SEQ ID NO: 45 | DND1 |
| CTAAATGGATTGTCATCCACAACTGcoding | SEQ ID NO: 46 | DND1 |
| TTATTGTCATAATGATTTTAATTTTcoding | SEQ ID NO: 47 | DND1 |
| AAGGCACCATGAAAGCAGCTCGTCAcoding | SEQ ID NO: 48 | DND1 |
| CAAACCCCAAAAAATGGGATAAAGAcoding | SEQ ID NO: 49 | DND1 |
| AAAATAGAAGGTATCTAATTTTTAAUpstream | SEQ ID NO: 50 | DND1 |
| TAAAAAAATAGAAATAACTACATGTUpstream | SEQ ID NO: 51 | DND1 |

TABLE 2-continued

DND1 ssDNA trigger sequences

| Sequences | | Sequence listing | gene |
|---|---|---|---|
| CTATCTTGGTTTCTTGCTAACTCTG | Upstream | SEQ ID NO: 52 | DND1 |
| TAATTTTATCAACTATTATACCATC | Upstream | SEQ ID NO: 53 | DND1 |
| GAATTTTTAGACCATTCAACCGGGA | Upstream | SEQ ID NO: 54 | DND1 |
| ACATTCTTGTAAAATATTTTCTCTG | Upstream | SEQ ID NO: 55 | DND1 |
| AAGGATATTTACAAATTTGAGACAT | Upstream | SEQ ID NO: 56 | DND1 |
| TTTCATATTTTCTTCATCCCAGCAT | Upstream | SEQ ID NO: 57 | DND1 |
| ATGATGGTAGCATGAGATTACACCC | Upstream | SEQ ID NO: 58 | DND1 |
| ATGGCTCATTTTAGAATAAACTTTA | Upstream | SEQ ID NO: 59 | DND1 |
| ATGGGGGCTCCCGTTAATCCGAAGA | control | SEQ ID NO: 60 | |
| AGCGCCGGTAGCGAGCATACGTATG | control | SEQ ID NO: 61 | |
| ACGACTCTGCTTATTATACTCGGTC | control | SEQ ID NO: 62 | |
| GACATATTAGGGGCGACGTCTCCAA | control | SEQ ID NO: 63 | |

Control oligos were generated using bioinformatics processes such that they would not match to any sequences in soybean, tomato, cucumber, lettuce, cotton, and maize with identity over 94.7%.

TABLE 3

Triggers were applied in pools of 3-4 polynucleotides each with the oligo amount being 20 nmol in 50 μl total volume in the presence of 5 mM NaPO4, 1% AMS, and 0.2% Silwet L-77.

| Trt | | SEQ ID NOs: |
|---|---|---|
| 1 | pool 1 | 34, 35, 46, 41 |
| 2 | pool 2 | 37, 36, 42, 47 |
| 3 | pool 3 | 43, 45, 38, 39 |
| 4 | pool 4 | 48, 44, 40, |
| 5 | pool 5 | 54, 57, 58, 50 |
| 6 | pool 6 | 51, 56, 55, 53 |
| 7 | pool 7 | 49, 52, 59 |
| 8 | control pool | 60, 61, 62, 63 |
| 9 | Form Blank | |
| 10 | Inoc Only | |
| 11 | Not Inoc | |
| 12 | Inoc- plugs only | |
| 13 | Inoc-tray only | |

Example 2. Application of Topical Polynucleotides to Soybean Leaves for Control of Soy Cyst Nematode (SCN)

Growth Chamber Whole Plant Assay

Figure 2:
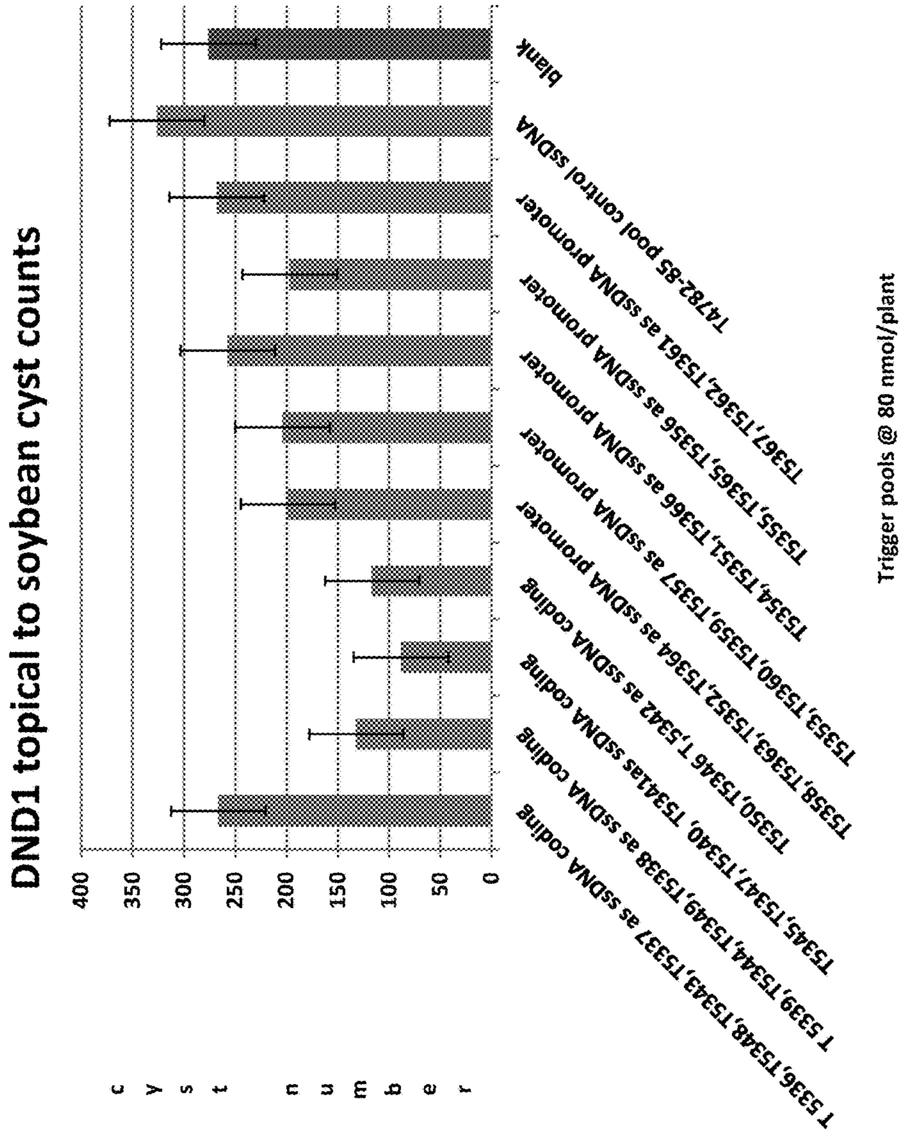
FIG. 2 shows the average total cysts removed from 4 replicas per treatment.
Figure 3:
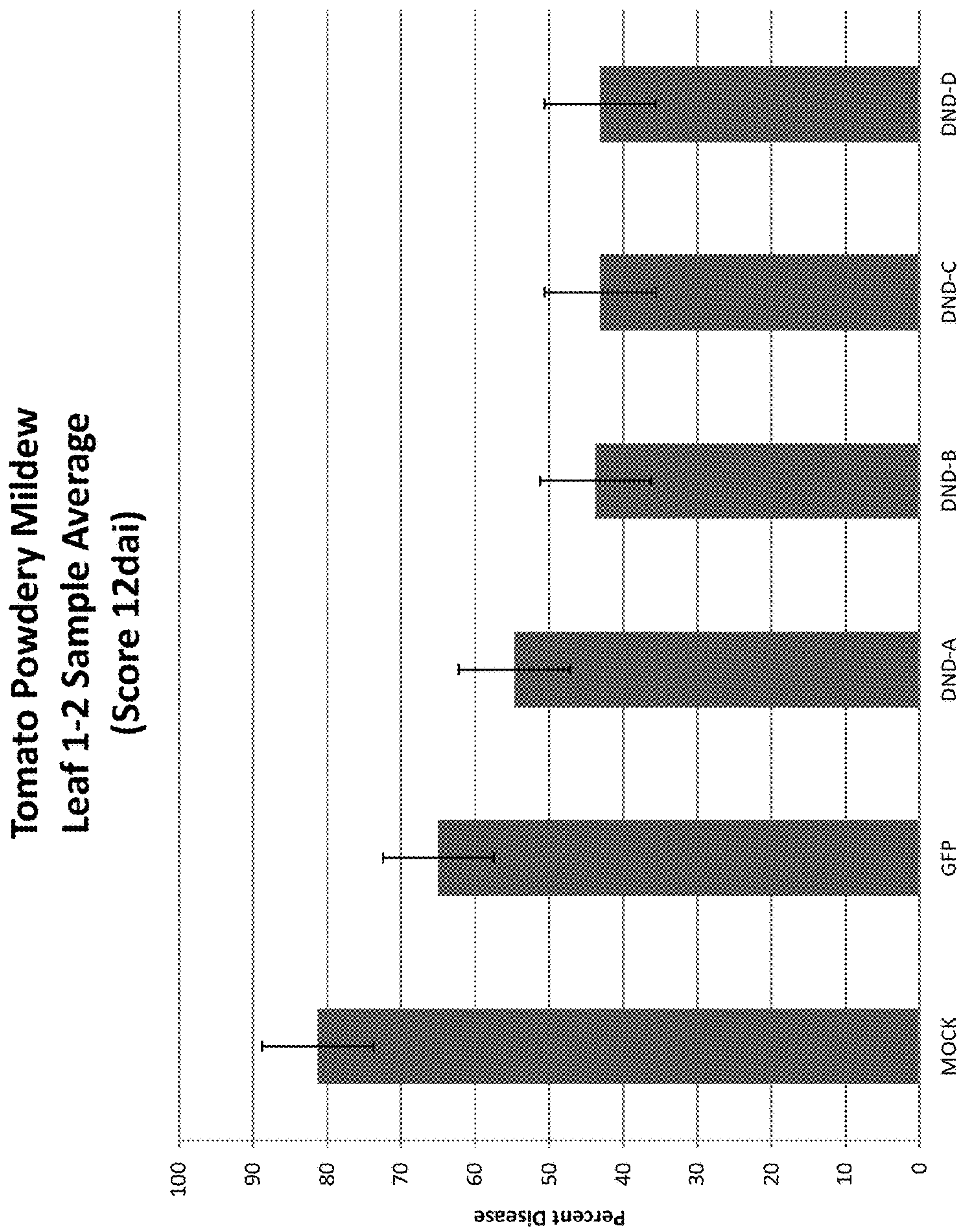
FIG. 3 is a graph showing the results of an evaluation of Tomato Powdery Mildew disease in treated plants.

Soybean seeds were planted in sand in 3 inch pots and allowed to grow for 8 to 11 days. Unifoliate leaves were topically treated with a pool of up to 4 ssDNA triggers targeting either the coding sequence or the promoter sequence of the DND1 gene. 20 nmol each total polynucleotide (80 nmols total) were mixed in a solution containing 0.2% Silwet L-77, 5 mM NaPO4 and 1% AMS in Gibco ultrapure water. The final volume of water was final 50 μL. Each unifoliate received 25 μL of the polynucleotide containing solution. One day after topical polynucleotide application, pots were inoculated with 1000 vermiform SCN eggs. Cysts were harvested and counted 28 days after inoculation. FIG. 2 shows the average total cysts removed from 4 replicas per treatment.

One pool in particular, Pool 3, containing oligos corresponding to SEQ ID NO:43, SEQ ID NO:45, SEQ ID NO:38, and SEQ ID NO:39, all in the antisense direction with respect to the DND1 coding sequence, gave particularly good efficacy in terms of decreased cyst number.

Example 3. Topical Oligonucleotide Application and Fungal Testing Methods

Application of Oligonucleotides to Leaves for Powdery Mildew Control.

Barley seeds are planted in 2 inch pots in the greenhouse. Five days later, barley seedlings are sprayed with nucleotides, either ssDNA and/or dsRNA oligos directed to the promoter and/or targeting the coding region of a target gene of interest such as SEQ ID NO: 1-33. The nucleotide solution applied consists of 6-20 nm of each ssDNA oligonucleotide or 0.5-4 nm dsRNA, 0.1 to 0.3% L77 Silwet, 50 mM $NaPO_4$ in a final volume of 40 μL water. Two to 4 days post spraying seedlings are infected with dry spores of barley powdery mildew (*Blumeria graminis* f. sp. *hordei*) and 7 days post infection, disease development is scored for the percentage of leaf area covered with powdery mildew.

Cucumber seeds are planted in a 3-inch square pot and thinned to one plant per pot after emergence. When the first true leaf is fully expanded and the second leaf is opening a nucleotide solution of either ssDNA and/or dsRNA oligos directed to the promoter and/or targeting the coding region of a target gene of interest such as SEQ ID NO: 1-33 is applied to the first true leaf or the cotyledons. The nucleotide solution applied consists of 6-20 nm of each ssDNA oligonucleotide or 0.5-4 nm dsRNA, 0.1 to 0.3% L77 Silwet, 50 mM NaPO4 in a final volume of 40 μL water. Two days later the entire cucumber plant is inoculated with a shower of dry spores of cucumber powdery mildew (*Podosphaera xanthii*) shaken off diseased plants. Disease severity will be evaluated on the treated leaf and succeeding leaves 10 days later and at subsequent intervals.

Tomato seeds are planted in a 3-inch square pot and thinned to one plant per pot after emergence. Two weeks old tomato seedlings are treated with 6-20 nm of each ssDNA oligonucleotide or 0.5-4 nm dsRNA, 0.2-0.5% L77 Silwet, 50 mM NaPO4, 1% ammonium sulfate in a final volume of 30 μL water. Two to 4 days post spraying plants are inoculated with dry spores of tomato powdery mildew (*Oidium neolycopersici*) and 13 days post infection, disease development is scored for the percentage of leaf area covered with powdery mildew.

Example 4. Use of VIGS to Suppress Expression of DND1 Gene for Control of Tomato Powdery Mildew (TPM, *Oidium neolycopersici*)

To identify polynucleotide sequences that can suppress DND1 expression and provide protection against Tomato Powdery Mildew infection, polynucleotides as summarized in Table 4, below, were introduced into tomato plants using a Tomato Golden Mosaic Virus (ToGMV) vector. Polynucleotide sequences that exhibit activity using VIGS-mediated suppression of DND1 are subsequently screened for their ability to suppress expression of DND1 and provide fungal and nematode resistance when provided to a plant through direct topical application with a transfer agent.

A modification of the sprout vacuum-infiltration-mediated agroinoculation method for virus-induced gene silencing protocol described in Yan et al. Plant Cell Rep (2012) 31:1713-1722 was used. Surface sterilized tomato seeds (Microtom variety) were first germinated on ¼ Murashige-Skoog media plus Cefotaxime. Approximately three days later, *Agrobacterium* component A containing ToGMoV: DND1 Suppression Sequence (Table 4) and the ToGMoV component B were each separately inoculated into 10 mL Luria Broth with appropriate concentrations of spectinomycin, gentamycin, and chloramphenicol and shaken at 24° C. for about 1-2 days to prepare an *Agrobacterium* inoculum containing the ToGMoV vector components. The A genome component is known to encode viral functions necessary for viral DNA replication, while the B genome component specifies functions necessary for spread of the virus through the infected plant (Revington, et al. Plant Cell. 1989 October; 1(10): 985-992). After about one to two days of growth, the *Agrobacterium* were pelleted by centrifugation and resuspended to a final OD600 of 0.05 in Infiltration Buffer (10 mM MES, 10 mM MgCl, 100 uM Acetosyringone). The *Agrobacterium* A component and B component were mixed for use at a 1:1 ratio and an Infiltration buffer only control (Mock) was also prepared along with GFP. The A and B component mixture, the mock Infiltration buffer control and the GFP controls were then allowed to incubate at room temperature (~25° C.) for 3-4 hours. About 3 mls of each sample containing a ToGMV vector with a given test DND1 suppression sequence or control was transferred into a small microtiter dish. Typically, 1 microtiter plate (6-24 wells) was used for each test ToGMV vector with a given test DND1 suppression sequence (typically >5 reps/polynucleotide sequence) and 1 microtiter plate was used for the controls (Mock, GFP). About 3-5 sprouts were added to each well; a vacuum was pulled for 10 seconds and then stopped. Pulling and stopping of the vacuum was then repeated 2 more times.

Vacuum-infiltrated sprouts were planted in soil, taking care not to cross contaminate samples. This was accomplished by changing gloves between samples and using new tweezers. Planted sprouts were covered with a humidity dome (70-80% humidity) and left at room temperature (~25° C.) overnight to recover. After one day, potted sprouts were transferred to a growth chamber (16 hr light cycle, 70% humidity, 200 μmol light, ~25° C.). Twelve days later plants were scored visually on the first two leaves to obtain an average disease rating/plant (ratings=0, 1, 10, 25, 50, 75 and 100%). Data was analyzed for all replicates using ANOVA Single Factor Analysis (α=0.1).

TABLE 4

Sequences of DND1 tested in the Tomato Powdery Mildew VIGS assay:

| SEQ ID NO | Species | Name |
|---|---|---|
| 64 | Tomato | DND1-A |
| 65 | Tomato | DND1-B |
| 66 | Tomato | DND1-C |
| 67 | Tomato | DND1-D |
| 68 | *Aqueoria victoria* | GFP |

TABLE 5

Average Disease Rating on Leaf 1-2

| VIGS vector used | Average % Disease | Percent (%) reduction to GFP |
|---|---|---|
| Mock | 81.25 | |
| GFP | 65 | |
| DND1-A | 54.69 | 8 |
| DND1-B | 43.75 | 26 |
| DND1-C | 43.13 | 27 |
| DND1-D | 43.13 | 27 |

ANOVA Single Factor:

| Groups | Repetitions | Sum | Average | Variance |
|---|---|---|---|---|
| Mock | 6 | 487.5 | 81.25 | 171.875 |
| GFP | 5 | 325 | 65 | 109.375 |
| DND1-A | 8 | 437.5 | 54.6875 | 398.9955 |
| DND1-B | 4 | 175 | 43.75 | 260.4167 |
| DND1-C | 8 | 345 | 43.125 | 347.7679 |
| DND1-D | 4 | 172.5 | 43.125 | 630.7292 |

ANOVA

| Source of Variation | SS | df | MS | F | P-value | F crit |
|---|---|---|---|---|---|---|
| Between Groups | 17396.75 | 6 | 2899.458 | 10.49402 | 1.19E−06 | 1.949626 |
| Within Groups | 9670.371 | 35 | 276.2963 | | | |

Potted tomato plants that were Agro inoculated with a recombinant ToGMV vector containing a sequence that provides for suppression of the endogenous DND1 gene showed decrease in Tomato Powdery Mildew (TPM) lesions on their leaves after TPM challenge. See Table 5. No decrease in TPM lesions was observed in control plants subjected to mock (Infiltration buffer only) treatment or a ToGMV vector containing a GFP sequence. Of the 4 fragments of DND1 gene tested, three (SEQ ID NO 65, 66, 67 corresponding to fragments DND1-B, DND1-C and DND1-D) gave comparable results, providing a 27% reduction of TPM lesions compared to the GFP control (FIG. 5).

What is claimed is:

1. A method for producing a soybean plant exhibiting an improvement in nematode disease resistance comprising topically applying to the soybean plant surface a composition that comprises:

a. at least one exogenous double stranded RNA (dsRNA) of 25 to about 95 nucleotides in length, wherein the dsRNA comprises a segment of 25 contiguous nucleotides that are identical or complementary to nucleic acid residues 1149 to 1806 of SEQ ID NO: 21, wherein said exogenous dsRNA is not operably linked to a promoter or to a viral vector and wherein the dsRNA is not transcribed from DNA integrated into a chromosome of the plant; and b. a transfer agent that conditions the plant surface to permeation by the dsRNA into cells of the plant, wherein said soybean plant exhibits an improvement in nematode disease resistance that results from suppression of an endogenous soybean DND1 gene.

2. The method of claim 1, wherein said transfer agent comprises a surfactant, lipid, or combination thereof.

3. The method of claim 1, wherein said dsRNA is selected from the group consisting of SEQ ID NO: 38, 39, 43, and 45.

4. The method of claim 1, wherein said composition comprises any combination of two or more of said dsRNA molecules.

5. The method of claim 1, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

6. The method of claim 1, wherein said transfer agent comprises an organosilicone preparation.

7. A soybean plant obtained by the method of claim 1, said soybean plant comprising an exogenous dsRNA of 25 to about 95 nucleotides in length, wherein the dsRNA comprises a segment of 25 contiguous nucleotides that are identical or complementary to nucleic acid residues 1149 to 1806 of SEQ ID NO: 21, wherein said exogenous dsRNA is not operably linked to a promoter or to a viral vector, is not transcribed from DNA integrated into a chromosome of the plant, and is not found in a non-transgenic plant; and wherein said soybean plant exhibits an improvement in nematode disease resistance that results from suppression of an endogenous soybean DND1 gene.

8. A composition comprising a dsRNA molecule of 25 to about 95 nucleotides in length, wherein the dsRNA comprises a segment of 25 contiguous nucleotides that are identical or complementary to nucleic acid residues 1149 to 1806 of SEQ ID NO: 21, wherein said polynucleotide is not operably linked to a promoter or to a viral vector; and a transfer agent that conditions a plant surface to permeation by the dsRNA into cells of the plant.

9. The composition of claim 8, wherein said dsRNA molecule is selected from the group consisting of SEQ ID NO: 38, 39, 43, and 45.

10. The composition of claim 8, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

11. The composition of claim 8, wherein said transfer agent is an organosilicone preparation.

12. A soybean plant comprising an exogenous dsRNA molecule of 25 to about 95 nucleotides in length, wherein the dsRNA comprises a segment of 25 contiguous nucleotides that are identical or complementary to nucleic acid residues 1149 to 1806 of SEQ ID NO: 21, wherein said exogenous dsRNA is not operably linked to a promoter or to a viral vector, is not transcribed from DNA integrated into a chromosome of the plant, is not found in a non-transgenic soybean plant; and wherein said soybean plant exhibits an improvement in nematode disease resistance that results from suppression of a endogenous DND1 gene.

13. The soybean plant of claim 12, wherein said soybean plant further comprises an organosilicone compound or a component thereof.

14. The soybean plant of claim 12, wherein said dsRNA is selected from the group consisting of SEQ ID NO: 38, 39, 43, and 45.

15. The method of claim 1, wherein said dsRNA of 25 to about 95 nucleotides in length comprises a sequence selected from the group consisting of SEQ ID NO: 38, 39, 43, and 45.

16. The composition of claim 8, wherein said dsRNA molecule of 25 to about 95 nucleotides in length comprises a sequence selected from the group consisting of SEQ ID NO: 38, 39, 43, and 45.

17. The soybean plant of claim 12, wherein said dsRNA molecule of 25 to about 95 nucleotides in length comprise a sequence selected from the group consisting of SEQ ID NO: 38, 39, 43, and 45.

* * * * *

SEQUENCE LISTING

<160> NUMBER OF SEQ ID NOS: 68

<210> SEQ ID NO 1
<211> LENGTH: 2001
<212> TYPE: DNA
<213> ORGANISM: Cucumis sativus

<400> SEQUENCE: 1
attcacaatc caaatatata gtttaattga tcattgattt acggtgtttc tttagattga 60
aagaaaaagg ttttttacaa attctatttt atttcaactc tttgtcctaa aaggtttcta 120
aaataaactt ttaaagtgtt gtaaaaaagt tattattaaa cctttcaaat tttcttctac 180
agaatttctc ttgtattaat taatgtgggg cattcttttt tgtactactc atccatttct 240
tgttcgtgta gtataaaata taattgtcct tgcacttggc ttgtgtctca ctcaaagttt 300
actgtttatc tcgtcaagta gataaaacgt ttagtggtca gaacgcaaag ctagaaaaac 360
aacaaatagt taataaatgg ttgaatcgcg gatcacactc tctttaagtc gttttgcggc 420
tctgcttctt tgtgcaaata aagttattgc atcgtcatcc ccaagataaa aaaacctttg 480
tttttcaatt gattttgcat ataaatcaat cggaatctca gcactcagat aaacgctcaa 540
aattgcttga taaactcaaa gaagaagttt gaaagaaatt ttttctagct tatgaaaatt 600
tgtcgcgtat atataatgaa agaatgaaaa aagtgtatat atagtgtgag agaattatca 660
atagacggtt ggaaattaat ttttggaaaa ttaattttgt aacaatttta tttatggaga 720
gattaggttg acttattaaa tacaaaacga taataaaacg tttgactctt ttaaatatgt 780
aataaagatc atgacatcaa tatatctcat catgctcgac catctctcct agaatgtcaa 840
tatatacgat gagacgatgt tctaaccttt cgcgtagctc atgttatcgc atagtcatga 900
tcaatattac atagttgaaa acttgctaaa acatgaaaga ctatcaagtt ttcattcgca 960
tcgaatttga aacatagctt agtcttctcg catcccataa agaattggcg tttaaaacat 1020
agttatatca cactgtttgg tcttattagg taaagaattt tccattcaac aattctccac 1080
ttaaattttt tttactatag gcaatttact cactttttat cttttattat tattattagt 1140
tccattatga aaatcaaatc attgacctta tttttagtat agattctaat taagtgttgt 1200
tttagtatag gtcattcatt gaacttcctt ttagtatcac aattgaggaa agggcatttc 1260
aacaatagag tgggtggtta ctaatacact tagatgctaa atggtcagtg attttaataa 1320
taaattaagt agggttggta ggggtgtgat ttaaagaatt tttctttaat tccatgctct 1380
ttcttggaag tttggagatt ttagagattt caataaagtt ggttgttgtg atgacagtaa 1440
agagtgattt taaaagctaa gatgaattca tttggaatca tatttttagt taaaaacttt 1500
gatagccata atgttggagt tggtttaggg cgctaataaa gggtaataaa gaaggacaat 1560
ttctccccac gttcagattt agagaaaaga aaagaagaat aaaatcagaa ttgaattaga 1620
ggaaaggtta aaagtgttat taacaaaaag gaaacgtatt gattggaatg ttagtagttg 1680
tagccaaata tattaagaaa actgaaccga cttgcacccg ttctataaat caaacaaaag 1740
atggggaagg tgtttttgga ggttgtgaaa tagagaagga taaatttgta aattaagaac 1800
taatattgtc gttattgatg aaatctctgt tggggttggg gttccccttt tgcatttata 1860
ttattcctca atcctccacc tctcttaata attccttttt tgtcacttct atctttaaca 1920
ctccaaaact cacattctca catccaacaa aacaacaata taacacctca ctaccctcct 1980
ccataactct cccttcatcc a 2001

-continued

<210> SEQ ID NO 2
<211> LENGTH: 2000
<212> TYPE: DNA
<213> ORGANISM: Glycine max

<400> SEQUENCE: 2
catgaaatat atatatatat atcttctttt tgaaattttc tcttaataca tattcatctt 60
tgcagctata gttatttttg tactataatc acattggggt taccttatgc gtgctataaa 120
ttaaaactta tgacctcatg cataatatct aaattttgat cttaacaaat ttttcactta 180
caactattaa ctattatata attctctata aaattaaaaa gagaaaaaga gcaaaacaag 240
aaagaaataa ttaaggaacg ataaagcaag ccaatccgga aaaaaacttg aaaggcaacg 300
catttctacg gcatgagatt ttcgtatcat tagtattatt taaactttga tatttattct 360
tgcttcatgg ttactctaaa gtctaaatcc tttctttgtt tatgtgataa gcacttttgg 420
aaacctagag agtacaactg aatggctaga agtagttttc aacatcattg tgctgaccag 480
tggccttctt cttgtcacta tgttgattgg aaacatcaag gtaaacacaa ttacccaggc 540
tatataaata agtgcgaatc caaaccaata attaatcaag cacattcatt ttagttcatt 600
cattaatttg gttgcgtaaa tatatttgtt atgaaattgt tttggcatat tatgggcacg 660
taccatatgt gtatgtatat acacggggca ggtatttttg cacgcaacaa cgtcaaagaa 720
gcaagcaatg caattgaaga tgaggaatat tgaatggtgg atgagaaaac gacgcttgcc 780
gctagggttt aggcagcgcg tgcgtaacta tgagaggcag cgttgggctg ccatgcgtgg 840
ggttgatgaa ttcgagatga ctaaaaatct ccctgaggga ttaagaagag acatcaagta 900
ccatctttgt ctagacttgg tgagacaggt aaggaaattt cctagaatac taaaaggatt 960
tttagtttcc attttaaaca ataaaaagaa attgagtaaa atatttggag gaaaaatcgt 1020
ctcagttttt cttgtttcta ggtattcctt tcactatttc tagctatcca catggaaaat 1080
aatattgttt attttccaaa aggaaaaaga aaatattttt cttttcttat cacacatatc 1140
tttttcggag attcatgtag ttaagaacgt atatatatag tctgactaat aaacatctaa 1200
tttagttcat gctcaaccta atttaatcac taaaaaatga agttactaaa tagtttctca 1260
agaatgcatc taatgtacca aactgctgaa tcagtatata tttgttgaac aatgagagga 1320
aaatggtttt gttttcacat cttagtaaca taataggttt tccattaaaa aaattaaact 1380
ggatcaaacc atactgcgct aaaagaactt gaatatatat aagtattacc tacatgttta 1440
gtttaattac accaaaaata atgaatagta cgctatgttt tgtttagctt cttgttagaa 1500
aaccaattac gtacgttttt ttttcttttt tctttataga gtaatggctt tatattttgt 1560
tcaggtgcct ctatttcaac acatggacga tctggttcta gagaacatct gtgaccgtgt 1620
gaagtctctg atattcacaa agggagaaac agtacgttct aatttccact atatagtatc 1680
acatgttgca taatgcattg ggacaaagtt aaataacatt aaataagaaa tatactgata 1740
ctaacacact ctatcatgaa ctaaaattta tagagaatta taagatttga caagtcccac 1800
tctttattta ataagtttta ttcatgattt tactgtttct aataaacttt aactattaat 1860
aaagaatgca atagaagagt gttaaaaagt agtatattgc tagctagtac tcgattgaaa 1920
taaatagatt tttatatact attttcaaat tgaaatgatt cagctttatt aaacctaaca 1980
tgattaacaa tatgatgcag 2000

<210> SEQ ID NO 3
<211> LENGTH: 1999
<212> TYPE: DNA

<213> ORGANISM: Cucumis sativus

<400> SEQUENCE: 3

```
taaaatttga tcatctgatt cgctctcgac tggatgccta cacacttgat ttggaggaag     60
cgaaacatgt gacgttcttg aagtttgttg aacgtctacg cttgatttgg agaagcgaag    120
cacataatgt tcttcaagtt ggttgaatgc ttacgcttga tttgaggaag tggaacatct    180
gatcttcttg aagttggaag aaagtttgta tcttcaaatg agtttcaatc ttcgagggtg    240
gtcgacttta ggagttggga agtcttgtag tttttgaaaa aattctctat agaccttatg    300
gagtaaaaaa aatttcaacc cttacaaatg aaagaatttc tctatttata gagttcttat    360
ttaattcgtg gattttaact taatctaatc gttaagatga aaacatgtga cattattaaa    420
atggtcaatt tatgtttttc aattctttaa tttggggcac atgtcaattt taattagtcc    480
taaattttaa tttatttgta cttttcatca acttaataaa tgatgtgaca atttatgatt    540
ggtctcaatt tcttattcaa cacatccgta ttgaatatct tttttctaat tctttataaa    600
tactcgtaga acattgctta tattatatgg taaaaaacaa tataaaacat tgaaagaaaa    660
tgtagttcga gcccggaagc atatatactt cgtgtaaggc aaagaattca aatcaaacac    720
atatggtggt atgtattgat ttgatgtatt tgtttttatt ttgacgtatg tgacacatat    780
cttacctacg attcaatgta tatatttttt tctaaaacaa aaaagatgaa caactcatta    840
tttaatatat ttcacaactc gaaactaaac aatctattta aaatgttcgt tctcttttct    900
aaagctaaaa gggcaaaaat aaataaaaga tcaaattttg gaataatttg attatcatct    960
tcacattttg aatcatcaca aagtctcgaa tagttttgtt ttcttattcg tcttttgtga   1020
tattattgaa aaagaaaaag aaatagttac aaaaatatta tattattgtt cacgctgaat   1080
ataagttaac tatctctcct atcaatttcg agatttaaaa tctgatctat ccaatgacat   1140
gtcgtgtatg aataaaattt tatgataaga attgagtgaa caatcattct ctataatgac   1200
taaaagggac catataaaga aaaagacatt gttttaataa ttttgaaata gtaatcaatc   1260
aaacattata ttatacacac tgtgctcaaa tgggtaggtc ctcatcactt tgctatagaa   1320
gttttggtgg ggcataaaaa tgtcttattc tctattttaa ttttcaaaat gacaattcta   1380
acctcttagt aaataataat aactcaaatg attgattgct ttataacttt gaaagttgat   1440
ttcctataac atcaaaaata gttacatgta ccactagcta tttgggtctt tatcatgcat   1500
atatacctta aagtctatac ctaatatttt cattgtctaa actttttta aaagtaaaat    1560
tacggaaaag ggtacgatgt ttttgtaata tatatatata tgtttagaaa attacatgat   1620
gtgtcatttt ccaaatttgt gatcatacaa aaacgtagtg aattttttg aaataatatt    1680
gataacgtat aattaatact tgatgcaaaa ttccactata aaaagaactt ttccctttct   1740
ctcaatgcac acatcaacca agattatttt caacgtatta ttcttttttt actttctctt   1800
tattagtttt taatctacca aaagaaagat gttctcaata ttaattaagt tgattatggt   1860
tgttatttgt aataatatct ccaacagaaa caacaaaggg gttgatgtgt gtatgttgag   1920
gttgacaaat tcaatttgta tacaaagaga atatggttaa aagggtgagt atggagattt   1980
ggtatgaagg tttcaattt                                                1999
```

<210> SEQ ID NO 4
<211> LENGTH: 2000
<212> TYPE: DNA
<213> ORGANISM: Glycine max

<400> SEQUENCE: 4

```
gggaaatgaa cacttaaaaa caactctaaa attatgaagt atttattata ctattatttt      60
cttaaactat ataaactaaa ctataaaact gcaagtattt tatggttgat tacttataca     120
acaaagccaa tataattgtt aagatataat aaaaaataaa cttttaatag agtgttttaa     180
cagtgtgttt ggtttatcgt tacacaatcc ttaatcctta gtgtatgttc attttaaagt     240
ttcctctcat atacttcccg gttgaatggt ctaaaaattc atgttaccaa caaaccaaac     300
agatactaac aaatatgctg ggatgaagaa aatatgaaat gacgaatatt aattactaat     360
atccttctac tgtaaaataa taaactgaat acacatgtga ttgcagaaat gtttcgattt     420
gaatattatg tgtcgcttga gaaatagtat ttaatgtact ttgtctttat ttgttcaaca     480
gaaaaaagat gccagctggt attcgaagat aagtagaatg ttttcctgtt tcaaatcatt     540
gtactcttgg ctattatacg tttcaaaata caaggcttat aaattatttt tcgagaattt     600
ttaaaaatta gataccttct attttaaaga aagataacaa attttttgga tattttaaaa     660
taatttttat tattggggtg taatctcatg ctaccatcat taatatcaca atttcattat     720
ttgcactttt aaacaggaaa aagttgtcac tgttatatgc gacatttatc acatgtagtt     780
atttctattt ttttatatct tttccagaaa catgcatatt aaaaatacac ttttagttta     840
aaggaacaat atttctatgt ctcaaatttg taaatatcct tattataaag tgaattcaag     900
ttatttaatg ttgttagctt aatattaatt ttactttaaa gggtttaaag aaagatatta     960
acagagaaaa tattttacaa gaatgtcatt atcatttttc tttagataag tataatagat    1020
ggtataatag ttgataaaat tatacttatg taatttaatc tctccttata tatatttaac    1080
taaattatga tcatcttttt attaatatat attttttcat ttcaattaac agagttagca    1140
agaaaccaag atagaattta aaaattgtat tttaaaacaa aacaaaaatt acagagtgaa    1200
taaacatgta aagtttattc taaaatgagc catacaaatt ttcgaataaa atcaaagtat    1260
ataactactg attacaacgt ttaaactata acaacttaga gtctatttta aagttgagta    1320
aaattaattt taataaaaat aataaccatc aaattttgta ttgaaatgtg taaatggtat    1380
tagaaatata aagccagaag tatataattg tgtctccaat agtttttctt tatctacaaa    1440
ggtagatact gattattatc tagtaaggtt ttttacattg gtagaaaaat acttgtattg    1500
tgtatggaat agtttgttat actaatacaa gcacattaag ttttacaata gttttaatct    1560
ttagcttaat acatatatat taaattctca tagaggatga gtaatgacat ttggatgcaa    1620
agttgaagga taagaagaag aagaagaaaa aaaagaaaga aaagagtagt gtgaggagga    1680
ggaggcaaac aaaagaaggt ggtcccaagt tatacagaaa acggcaaaga gcaaacagca    1740
gggttgagta gagagtagca accccaccac ccttccctca acgttgcgta accgtaagct    1800
ccaatcccca ccctcttcca tttcacatgc aaattcatcc ctctttattc tcatctcatt    1860
tccatgctct cttcttatat agtacccttc ttccactcca tgtgccttcc tctgacacac    1920
tctaatccca ctcctcccaa tccctccatg taactcacct tcttccccat gctaatggtt    1980
tctctccgat atctccaacc                                                2000
```

<210> SEQ ID NO 5
<211> LENGTH: 2091
<212> TYPE: DNA
<213> ORGANISM: Lactuca sativa

<400> SEQUENCE: 5

```
atgttagacc agagaagcaa gctgatcaac catggtgacg atctagacga cgaaagtcac      60
```

-continued

```
ccaatttcgt tcacaaccga atgttatgca tgcactcaag taggtgttcc ggtgttccac    120

tccactagct gcaaccaagc tcagcaaccg gaatgggaag cttccgccgg ctcatccctc    180

atccccatcc gcaacagacc cggttccaag atcatcaaga accgatattc cgccggaaaa    240

cggagaccac tgtcgtcttc agggttgtcg ttcaggcgag tgtatgatcc aaggagcaaa    300

agtgtacaaa ggtggaatag gtttgtgttg cttgctcgtg gtatggcgtt ggctgttgac    360

cctttgttct tctactcgct gtcaataggc cgtgggggta cgccgtgtct ttacatggac    420

ggcggtcttg cggcggttgt ggccgtgctg cggacaatga ttgactgctt ccatgtcgtc    480

cacatatggt tacagtttcg ggtggcttat gtgtcacgtg agtcgcttgt ggttggttgt    540

gggaagctgg tgtgggaccc gaagtctatc gcattgcatt atgtgcgatc acttaaaggc    600

ttctggtacg acatattcgt cgtactgccg gttcctcagg ttgtgttctt attggtactt    660

ccgaaactta tccaagaaga gcgaataaaa acgatcatga ccacccttct gctagttttc    720

atgttccagt tcctccccaa agtctaccac tccatctact taatgagacg gatggcaaag    780

gtcaccggct acatcttcgg caccatttgg tggggtttcg cccttaatct aatcacttat    840

tttattgcct ctcatgttgc cggtggctgt tggtacgttt tggcaataca acgagtggtt    900

ttgtgtctta gacaacaatg tgaaaacaaa aactcatgcg atcttaccct ttcgtgcgcc    960

gaggagattt gctaccagtt ttcaggaacc tcaggaaatc catgcaatag aaacttcacc   1020

atgcatgctg ttagaatgcc attgtgttta gatacgaatg gaccatacca ttatggtatc   1080

tatcagtggg cgcttcctgt gatctctagc aactcactaa ggataaaaat tctttatcct   1140

atcttttggg gtttaatgag tctcagcact ttcgggaatg atcttgagcc cactagtcac   1200

tgggtcgaag tgatcttcag tatttgcatc gtgctgagtg gcttgatgct attcacctta   1260

ttgattggta atattcaggt gtttctgcat gctgttatgg cgaggaagaa gaaaatgcaa   1320

ctgagatgcc gagatatgga gtggtggatg aaaaggagac aactgccatc gcgtcttaga   1380

catagagttc gccattatga acgccaaaat tgggttttga tgggtggaga agatgagatg   1440

gaattgatta aagagttccc agaaggcctc agacgagata tcaaacggtt tttatgtatt   1500

gatctaatcc gaatggtacc attgttccat aacttggaag atcttattct tgataacatc   1560

tgtgatcgtg ttaagccgct tgtgttttca aaagacgaaa agatcatcag ggaaggggat   1620

ctagtgcaac gaatggtgtt cattgttcaa gggcgtgtaa aaagctacca aaacctaagt   1680

aaaggagttg tagcgacaag catcctggac cctggaggct acttcggcga tgagcttctg   1740

tcatggtgcc ttcggagacc attgataaac aggcttccgt catcttcggc tacatttacg   1800

tgtttagaag ctacacatgc atttgggttg gatgcgaacc atcttcagta tgttacagac   1860

cattttcggt acaaatttgc aaacgagagg ctgaagcgta cagtgagata ttactcctcg   1920

aactggagga catgggcggc agtaaatatc cagcttgggt ggaggaggta tacggcgagg   1980

atgaggccgg tgatggctat tgtaagtgca gagaataatg gcagtgaccg tatgcttagg   2040

cagtatgctg ccattttcat gtcaattagg ccacatgatc atttggattg a            2091
```

```
<210> SEQ ID NO 6
<211> LENGTH: 2127
<212> TYPE: DNA
<213> ORGANISM: Solanum lycopersicum

<400> SEQUENCE: 6

atgtcttctc accaagacgt ccgcttcttc ctctcaaagt ggtttggcat attccgacga     60

agatcagttc aacctgataa cagcgacgac aacgatgacg acatcaatcc aatctcaaat    120
```

```
tccattgaat gttatgcatg tactcaagtt ggcgtccctg ttttccactc caccagttgc    180
gatggagcta accaaccgga gtgggaagct tcagccggtt cttctctagt tccaattcaa    240
aaccggacgg attcaaaaac cggaaaatcc cggtccagtc gcagccggca cacatcgggg    300
ccgttcgggc gtgtattaga ccctcgaagc aagcgcgtgc agagatggaa ccgaatgatt    360
ttattggcac gtggcatggc tttagccgtt gatcctctat tcttttacgc cttatccatc    420
ggccgcggtg gatcgccgtg tttgtacatg gacggcagcc tggcggctat cgtcaccgtg    480
attcggacta gcgtcgacgc cgtgcacctc ttccatttgt ggttgcagtt tcgtttggct    540
tacgtgtcga gagaatcgct ggtggttggt tgtgggaaac tcgtgtggga tgcgcgtgcg    600
attgcttctc actatgttag gtcccttaaa ggattttggt tcgatgcttt tgtcatcctt    660
cccgttccac aggctgtatt ctggctggtg gttccaaaac taataagaga agagcagata    720
aagcttataa tgacgatcct tttattaatg ttcttgttcc agttccttcc caaagtttat    780
cactgtataa gcttaatgag aaggatgcaa aaggttacag gatatatttt tggtaccatc    840
tggtggggat ttggacttaa tctcattgct tattttattg cttctcatgt tgctggggga    900
tgctggtatg ttcttgcaat acaaagagtg gcttcatgtc taaggcagca gtgtgagcgc    960
aacccttcgt gtaatctatc tttgtcttgc tcagaggagg tgtgttatca gtttctgttg   1020
ccaacaggaa ctgtgggaaa tccatgtgct gggaactcaa caacagtgac caggaagcca   1080
atgtgtttgg atgtcaatgg accatttcca tatgggatat accaatgggc acttcctgtt   1140
gtttctagca gatccgtcac tgttaagatt ctttacccca tcttttgggg attgatgacc   1200
cttagcacat ttggcaatga cttagaacca acaagtcact ggctggaagt tattttcagt   1260
atatgccttg tgcttagtgg attgatgctc ttcactttgc tgattggtaa cattcaggtg   1320
tttttacacg cggtcatggc aaagaagcga aaaatgcaat taagatgtag ggatatggaa   1380
tggtggatga ggaggagaca attaccatca caattaagac aaagagttcg ccactttgaa   1440
caccagagat gggctatgat gggtggcgaa gatgagatgg aacttgtaaa agacctgcca   1500
gaaggactac gaagggacat caaacgcttt ctttgccttg atcttattaa gaaggttcct   1560
ctgttcgaaa gtttggatga tctgattcta gataacattt gtgatcgcgt taagccactt   1620
gtgttctcta aagatgagaa gatcataaga gaaggagatc cagtgcacag ggttgtgttc   1680
attgttcgtg gacgtgtaaa aagtagccaa aacctcagta aaggagtgat tgccacaagc   1740
atacttgagc ctggaggctt ctttggagat gaacttcttt cctggtgctt acgccgtccc   1800
tttattgaca gacttccagc ttcttccgca accttcactt gcattgaatc tacagaagca   1860
tttggcttag atgcaaacca ccttcgattt atcacggatc acttcagata caaatttgca   1920
aacgagaggc tgaagagaac agcaaggtat tattcatcca attggagaac ctgggctgct   1980
gtgaatatac agttagcttg gcgacgttac atgatgagga ctagccgtcc cactatacat   2040
gtgatcgaaa atggggataa tgatcatcgt cttcgcaagt atgctgcaat gttcttgtca   2100
atcagaccac atgatcatct tgaatag                                       2127
```

<210> SEQ ID NO 7
<211> LENGTH: 2061
<212> TYPE: DNA
<213> ORGANISM: Cucumis sativus

<400> SEQUENCE: 7

```
atggttcggt ggagcgagct ttgtctgagg ccatcaccgc ctcctctcaa tgtcgccgcc     60
```

-continued

```
gacgcaaccc cagtcttgga atgctacgcc tgtacccaag tgggcgttcc agccttccac    120

tccaccagct gcgaccacgc ccaccaacaa cccgaatggg aagcctccgc gggctcttcc    180

ctggttccaa tccaacccac aaaatcctca ccagcgcccc gacattcttc ggcgggttgc    240

ttcgggacgg ttctggaccc aagaaagaaa ccggttcaga gatggaaccg ggttctgtta    300

ttggcccggg gaatgtctct tgcggttgat ccgctttact tctatgctct gtctattgga    360

agaggaggat ggccttgcct gtacatggat ggtgggttgg ctgccggagt tacggtggtt    420

cgaacgtgtc ttgatatagt gcacttgtgg cacgtgtggc ttcagttcag gcttgcttac    480

gtgtcgaaag agagtatggt gattgggtgt gggaaactgg tgtgggatgc acgtgatatt    540

gcttctcact atgttcgttc tttcaaaggc ttttggtttg atgcctttgt tatcctccct    600

gttcctcaga ttgtttattg gttggtttta ccaaaactga tcagagaaga aagaatcaaa    660

cttataatga cagtaatctt attaatgttc ttgttccaat tcctcccaaa agtttaccac    720

tccattattt taatgagaag aatgcagaag gttactggat acatctttgg caccatttgg    780

tggggttttg gcctcaatct cattgcctat tttattgcct ctcatgttgc tgggggttgt    840

tggtatgttc ttgcaataca gcgagttgct tcttgtatcc aacaacattg tgagagaaac    900

aagtgcaact tatctttgtc ttgctctgag gaggtgtgtt atcagtttct atcatcagat    960

acaacgattg gaagttcgtg tggtcggaat tcgactgcta cgtttaggaa gccactatgt   1020

ttggatgtta atggtccgtt cgcctatggc atctacaagt gggctcttcc tgtcatttct   1080

agcaattcag ttgctgtcaa aatcctttat cctatctttt ggggattaat gactctcagc   1140

acctttggaa atgatcttga gcctacgagt aattggctgg aagtgtgctt cagtatttgt   1200

acggtgctta gtggattgtt gcttttcact cttttgattg gtaatattca ggtacttttg   1260

cacgctgtca tggcaaggag gcgaaaaatg cagctgagat gtcgagattt ggagtggtgg   1320

atgaggagac gacaattgcc atctcgtttg aaacatcgag ttcgacacta tgagcaccag   1380

agatgggcag ctatgggagg agaagatgag atggaactaa tcaatgattt gccagaaggt   1440

cttagaagag atatcaaacg tcatctttgt gttgacctaa tcagaaaggt gcctctcttt   1500

caaaacctgg aggagctgat tctagacaac atatgtgaca aagtcaagcc acttgtattc   1560

tccaaagatg aaaagataat cagagaagga gatcctgttc caaggatgtt attcatagtg   1620

tgtggacgag taaaacgtag ccaaagcctg agcaagggca tgacagcgac aagttttatt   1680

gaaccgggag gatttcttgg tgacgaactg ctatcgtggt gtcttcgtcg cccatttctg   1740

gagagacttc cagcttcatc cgctacattt gtttgcattg aaccaacaga agcatttgcc   1800

ctgaaagcag accatctgaa gtacataacc gatcacttcc gctacaaatt cgcgaatgag   1860

agactgaaga gaacagcaag attttactct tccaactgga gaacatgggc tgctgttaac   1920

atacaacttg cttggcgtcg atacagaaaa cggatgaggc gtccagtgat agctgtggtg   1980

gaaaatggaa gcactgaacg tcggcttttg cagtatgctg caatgttcat gtcattcaga   2040

ccacatgatc atcttgaata g                                             2061


<210> SEQ ID NO 8
<211> LENGTH: 1424
<212> TYPE: DNA
<213> ORGANISM: Hordeum vulgare

<400> SEQUENCE: 8

tacgttcttg cgattcagcg tgtcgcctcc tgcctacaat ccgaatgcga gataaacaac     60

aattgcaatt tgatgtcact ggcttgctcc aaggagatgt gctttcactt cccttggtca    120
```

```
tcagatatga ctgcattggc atgcgatacg aacttaactt ctttcagcca acaaaatgtg    180

ccggcctgtc taagtggcaa tggcgccttt gcttacggaa tctacaaggg agcccttcct    240

gttatctcga gcaattcact tgctgtcaaa attctctatc ccatattctg ggcctcatg     300

accctcagca catttggaaa tgatcttgag ccgacgagca actggcttga ggtgatcttc    360

agcatcatta atgtactcag cgggctgatg ctcttcacgc tgctgatcgg caacatacag    420

gtattcttgc acgccgtgct ggcgaggaag cggaagatgc agctgcggtt ccgggacatg    480

gagtggtgga tgaggcggcg gcagctgccg tcgcggctgc ggcagcgggt ccggaagtac    540

gagcgggagc ggtgggcggc catcaccggc gacgaggaga tggagatgat caaggacctc    600

cccgagggcc tccggcggga catcaagcgg tacctctgcc tggagctggt gaagcaggtg    660

cccctgttcc acggcatgga cgagctgatc ctggacaaca tctgcgaccg gctgcggccg    720

ctggtgttct gcggcggcga gaaggtgatc cgggagggcg acccggtgca gcgcatggtg    780

ttcgtcctgc aggggaagct gcggagcacg cagccgctga ccaagggcgt ggtggcggag    840

tgcgtgctgg gcgcggggag cttcctcggc gacgagctgc tgtcgtggtg cctgcggcgg    900

ccgttcgtcg accggctgcc ggcgtcgtcg gccacgttcg agtgcgtcga ggcggcgcag    960

gccttctgcc tcgacgcgcc ggacctgcgc tacatcacgg agcacttccg gtacaagttc   1020

gccaacgaca agctcaagcg caccgcgcgc tactactcgt ccaactggcg gacgtgggcc   1080

gccgtcaacg tgcagctcgc gtggaggagg tacagggcca ggatgatggc gacggcggtg   1140

ctgccgccgc cgccggccgg cgcggcgggg cccgaggacg gggaccgccg gctgcggcat   1200

tatgcggcca tgttcatgtc gctcaggccg cacgaccacc tcgagtaggc tcgggaccgt   1260

tcgggtggct aggggatcgg aggggacgtg ggcatgtaga gggaccttgc tttggtataa   1320

cgtgtatctg tcacgttgta gctgacaagg ctcgccattt attaaggatg atcagtacaa   1380

taatggaggt ggaggtggta tttctaaaaa aaaaaaaaaa aaaa                    1424
```

```
<210> SEQ ID NO 9
<211> LENGTH: 1743
<212> TYPE: DNA
<213> ORGANISM: Lactuca sativa

<400> SEQUENCE: 9

atggcttgta ggaatgaaca ttcagatgct tacacagaaa ccactgacga agaagaagaa     60

gtagcagaaa aagagtacga ggagaacata tatagcgtgt gtagtccaag tgggagagca    120

agaattgacc cgagatctcc atgggtccaa gaatggaacc gggttttcct gttggtgtgt    180

gcgatgggtc tgttcgtgga cccgctcttc ttctacactc tgtcgattag cgagtcgtgc    240

atgtgtttgt tcgtcgacgg gtggttcgcc gtcactgtga cggtgctccg gtgcatgacg    300

gacgcgttgc acctgtggaa tatatggttg cggttcaaga tgaaaaggtc atctccactt    360

gacgaacgcc ggttcagcac cgatgaatcg attgtacgga acgtgctgac gaggttgatg    420

acggaggcca gaaaccgctt ctcacttgat atcttcgtcg tcttaccaat ctctcaggct    480

gtgggtgctt gttggtactt gctaggagcc cagaggactt ccagatgctt gaaggagaaa    540

tgcatggaaa caaatggatg catgccaaga gtattgacgt gtgaaaactt catgtattat    600

ggaacaaaca aactagtgat aagagacacg tggagactct tatggggtga gagtagaagc    660

acaaggacta cttgtctaca aggtagcgac agtttcagtt ttggtgcata taaatggaca    720

gttcaactcg ttaccaatga gagcagattg gagaagatac tcttccccat attttggggt    780
```

-continued

```
ttgatgacac taagtacatt tggtaacttg gagagcacaa cagattggtt ggaagtggtt    840
ttcattatca ttgttctcac gacgggcctc cttttagtca ccatgttgat tggaaacatt    900
aaggtgtttt tgcatgcaac gacatcaaag aaactagcaa tgcagttgaa aatgagagac    960
atagagtggt ggatgaggag gagacgcctc cctcaagaat ttagacaaag agtcagaaat   1020
tacgagagaa aaagttgggc agccatgcgt ggagttgatg agtgtgagat gattcgcaac   1080
ctgcctgagg gcctgcgaag agatataaag taccatctat gcttggattt ggttcgacag   1140
gtaccttat ttcaacatat ggacaacctg gtccttgaga acatatgtga ccgtgttaag   1200
ccccttattt acactaatgg agaaataatt actcgagagg gagatgcagt gcaaaggatg   1260
ttatttatag tacgagggca tcttcaaagt agccaatatt tacgagatgg tgtcaaaagt   1320
agttgtatgt taggcccagg aaacttcagt ggggacgagc tcttatcgtg gtgtctaaag   1380
agacctttca ttgaaagact accttcatca tcatcaacac tagtcactct cgagaccaca   1440
gaagcttttg gcctagatgc cgaagatgta aagtatgtta cacaacattt tagatatact   1500
tttgtgaacg aaaaagtgaa gatgagtgca agatattatt caccaggatg gaggacttgg   1560
gccgcagttg cgattcaatt ggcttggagg aggtacaagc atagacttac acttaactcg   1620
ttgtcgttta ttagaccaag gagacctttg tctaggtgtt cttcacttgg ggaagatagg   1680
ctaagacttt atacggctct attgacttcg ccaaagccta atcaagatga ttttgaattt   1740
tga                                                                 1743
```

<210> SEQ ID NO 10
<211> LENGTH: 2441
<212> TYPE: DNA
<213> ORGANISM: Solanum lycopersicum

<400> SEQUENCE: 10

```
agtgcatata ttctcttcat tttttttat ctccatatcc caaatccata aaagaaaaaa      60
actagcacaa aaaaaaaaaa ttaatggcta gtcatcatga acttgaacta tcaaataatt    120
atagtgatcg aagtgacgat gacatggacg aggacgagga tgagcaagat aacatagaag    180
aggaggaaaa agaagatgat aattcaaatg actacaacat ttgtagtagt cgtagtcgag    240
gaggaggatt gacagacttc ttttcgtgga aagtcataga ccctagagcg ccttgggttc    300
aagaatggaa tcgagtattt ttattagtat gtgccacggg gctatttgtg gatcctctct    360
ttttctactc tctctctatc agcgagactt gcatgtgcct ttttatcgat ggttggtttg    420
cggtaacggt caccgttctt cgatgcatga ccgatgcgat gcatttatgg aacatgtgga    480
tacgattcaa gatgcataaa ttacgtcctt acaatgaaaa aatggatgaa aatcaaatta    540
ctagtagtag tcgaggtcca cgactacatc aagaccagag ttttcgatgt tttgtggcct    600
tacgatactt gaaatccaag aagggtttct ttttggatct ctttgtcatc cttcctttac    660
ctcagatagt gatgtgggta gggattccag gtttactgga gaaaggatat acaacaacag    720
taatgacagt attattaata atgtttctgt ttcaatatct gcccaaaatt tatcactcag    780
tttgcctgct aagacgcatg cagaatctct ctggatacat ttttggtact gtttggtggg    840
gaattgctct taacttgatt gcttattttg ttgcctccca tgcagtggga gcatgttggt    900
acttgctagg aatccaaagg gcagcaaaat gtttgaaaca acagtgtaga gttacaaatg    960
gttgtagcct aagaatgttg gcatgtgaag agaaaatatt ttatggaaca agtagtttgg   1020
tgaagcatag aagtagagtc atatggggtg agtccaaaat tgcaagatca acatgtctag   1080
cctctgaaca caattttgat tatggagttt ataaatggac tgttcaactt gtcacaaatg   1140
```

agaatcgttt tgagaaaata ttatttccca tcttctgggg tctcatgact ctcagtacat 1200
ttggaaactt ggagagcaca acagattggc tggaagatgt attcataatc attgttctca 1260
ctactggtct tcttcttgtc actatgttga ttggtaatat caaggtattc ttgcatgcaa 1320
caacatcaaa gaaacaagca atgcaactaa aaatgagaaa tgtagaatgg tggatgagga 1380
gaagaaggtt gcctcaagga tacaagcaaa gggtcagaaa ttatgaaagg catagatttg 1440
cagcaacaag aggagttgat gaatatgaga tgataagcaa ccttcctgag ggacttagaa 1500
gagacatcaa atatcatctt tgtttggact tggttagaca ggttcctttg tttcaacata 1560
tggataattt ggtcctggag aacatatgtg accgcgtaaa atccttgatt ttcactaaag 1620
gagaaacaat aacaagagaa ggtgatccag ttcaaagaat gttgttcata gtgagaggtc 1680
atctccaaag cagtcaagaa cttagagatg gtgtcaaaag ttgttgcatg ttgggccctg 1740
gaaacttcag cggcgacgaa cttctctcat ggtgcctccg gaaacccttc gtggagcgtc 1800
taccgccttc ctcctcatcg ctagtgactc tcgagaccac agaagcgttt ggcctcgaag 1860
cagatgatgt caagtatgtc actcaacatt tccgctacac atttgtgaat gagaaagtga 1920
agagaagcgc cagatattat tctccaggat ggcgaacttg ggctgccgtt gctattcagt 1980
tggcctggag gagatataga caccggctga ctctcacgtc gttgtccttc attcgaccaa 2040
gacgaccgtt gtctcgatct tcttcattaa cagaagacag actcaggcta tatacagctt 2100
tgctcacttc accaaagcct aatcaggacg attttgattt ttaaaaagag caacaaacaa 2160
atggaatgtt accttctttc tgttatgaga taggagcaca tccccctccc tctatatgtc 2220
cttcaattat ccattcatgt gatatgtagt agtctcttcg tttcaattta tgtgaattcg 2280
tggacaccga gtttaagaaa gaaaagaaga ttttgatcta cagagtctgt agattttgag 2340
gtcatgtaga acatctcaga tcaagtgtgt ctgattttat cctccatgtg tgctacttgt 2400
atcttttcct gaatataatt atttctaatc taaaaaaaaa a 2441

<210> SEQ ID NO 11
<211> LENGTH: 1980
<212> TYPE: DNA
<213> ORGANISM: Cucumis sativus

<400> SEQUENCE: 11
atggccacca cctccctaac atccgatgac gaagagctag accaccaaga atcagaagaa 60
gaagaacact ccaacgctgc gttttgtcag agcttatacg gagttgcttc agttctcgac 120
ccaacatcca aatgggttcg agaatggaat tgggtcttcc tcctcgtctg tgcagcgggc 180
ctgttcgtcg accctttgtt tctctacacg ctatccataa gcgagtcgtg gatgtgcgtt 240
tttattgacg ggtggttggc catcaccgtg accgtcctcc gctgcatggg cgatgctttg 300
cacctttgga atatgtggct tcagctcaag actgctacaa agtcatcctt tgctggtagc 360
ggggagggtg atgggagggg tgaaaataga cggctttgcg atagtagccc acgcgccgtc 420
gctctccggt atttgaagtc caagaaaggc ttcttttttg atctctttgt cattcttcct 480
tttcctcagg ttgtattatg gatagtaatt cctagaataa tgaaagaagg attagtgaca 540
tcggtgatga cagtcttatt gatagttttt ttgtttcaat atttaccaaa attgtaccat 600
tctgtttgct tactacgacg tctccaaaac ctttctggtt acatctttgg cactgtttgg 660
tggggcattg ctctcaatct cattgcttac tttgttgctg cccatgctgc aggtgcatgt 720
tggtatctat taggggtaca aagagcagca aaatgtctaa aagagcaatg tagatcagca 780

-continued acaaccaaca gctgtgggct gaggttgtta tcatgcaaag acccaatctt ctatggacca 840
aacaatatga gaatgggaag agatggagga aggtttgatt gggcaaacaa taggctatca 900
aaattcatgt gtttagatac tgctgataac tttgattatg gagcttataa atggactgtt 960
caacttgttg tcaatcaaag tcggttggag aaaatccttt tccccatctt ttggggcctc 1020
atgactctta gtacctttgg gaatttggaa agcacaactg aatggctgga agtagtgttc 1080
aatatcattg ttctcaccag tggactctta ttggtcacca tgttgattgg aaatatcaag 1140
gtgtttctac atgcaacaac gtcaaaaaaa caaggaatgc agctgaagat gaggaaccta 1200
gagtggtgga tgaggaagcg aaggctgcca caagggtttc ggcagcgtgt tcggaactat 1260
gaacgccaac ggtgggcggc gatgcggggt gtggacgagt gcgagatgat aaaaaaccta 1320
ccggaagggc ttagacgaga cataaagtat cacctttgct tggatctagt caggcaggtg 1380
ccattgtttc aacatatgga tgatcttgtt cttgagaaca tttgtgatcg tgtcaagtcc 1440
ctcatcttca ctaagggcga aaccataaca agagaaggag atccagtaca aagaatgcta 1500
ttcgtagtgc gagggcatct ccaaagcagc caagtcctac gcgacggcgt aaaaagctgc 1560
tgcatgttgg gccccggcaa cttcagcggc gacgagcttc tatcctggtg cctccgccgc 1620
cctttcatag agcgccttcc accctcctcc tttactctcg tgacactgga gaccactgaa 1680
gccttcagct tggaggccga ggatgtcaag tatgtaaccc agcacttccg ctacaccttt 1740
gtcaatgaca aggtcaagcg cagtgcccgc tactactccc caggctggcg cacttgggct 1800
gctgttgcca tccagctagc ctggcgccga tatcgccatc gtctcacact cacgtccttg 1860
tcctttattc ggccccgccg cccactctca cggtgctctt ccttggggga ggatcgcctc 1920
cgcctctata cggcgttgct tacttctcca aagcccaacc acgaccactt tgatttttga 1980

<210> SEQ ID NO 12
<211> LENGTH: 1980
<212> TYPE: DNA
<213> ORGANISM: Hordeum vulgare

<400> SEQUENCE: 12
atggccacca cctccctaac atccgatgac gaagagctag accaccaaga atcagaagaa 60
gaagaacact ccaacgctgc gttttgtcag agcttatacg gagttgcttc agttctcgac 120
ccaacatcca aatgggttcg agaatggaat tgggtcttcc tcctcgtctg tgcagcgggc 180
ctgttcgtcg accctttgtt tctctacacg ctatccataa gcgagtcgtg gatgtgcgtt 240
tttattgacg ggtggttggc catcaccgtg accgtcctcc gctgcatggg cgatgctttg 300
cacctttgga atatgtggct tcagctcaag actgctacaa agtcatcctt tgctggtagc 360
ggggagggtg atgggagggg tgaaaataga cggctttgcg atagtagccc acgcgccgtc 420
gctctccggt atttgaagtc caagaaaggc ttcttttttg atctctttgt cattcttcct 480
tttcctcagg ttgtattatg gatagtaatt cctagaataa tgaaagaagg attagtgaca 540
tcggtgatga cagtcttatt gatagttttt ttgtttcaat atttaccaaa attgtaccat 600
tctgtttgct tactacgacg tctccaaaac ctttctggtt acatctttgg cactgtttgg 660
tggggcattg ctctcaatct cattgcttac tttgttgctg cccatgctgc aggtgcatgt 720
tggtatctat taggggtaca aagagcagca aaatgtctaa aagagcaatg tagatcagca 780
acaaccaaca gctgtgggct gaggttgtta tcatgcaaag acccaatctt ctatggacca 840
aacaatatga gaatgggaag agatggagga aggtttgatt gggcaaacaa taggctatca 900
aaattcatgt gtttagatac tgctgataac tttgattatg gagcttataa atggactgtt 960

-continued caacttgttg tcaatcaaag tcggttggag aaaatccttt tccccatctt ttggggcctc 1020
atgactctta gtacctttgg gaatttggaa agcacaactg aatggctgga agtagtgttc 1080
aatatcattg ttctcaccag tggactctta ttggtcacca tgttgattgg aaatatcaag 1140
gtgtttctac atgcaacaac gtcaaaaaaa caaggaatgc agctgaagat gaggaaccta 1200
gagtggtgga tgaggaagcg aaggctgcca caagggtttc ggcagcgtgt tcggaactat 1260
gaacgccaac ggtgggcggc gatgcggggt gtggacgagt gcgagatgat aaaaaaccta 1320
ccggaagggc ttagacgaga cataaagtat cacctttgct tggatctagt caggcaggtg 1380
ccattgtttc aacatatgga tgatcttgtt cttgagaaca tttgtgatcg tgtcaagtcc 1440
ctcatcttca ctaagggcga aaccataaca agagaaggag atccagtaca aagaatgcta 1500
ttcgtagtgc gagggcatct ccaaagcagc caagtcctac gcgacggcgt aaaaagctgc 1560
tgcatgttgg gccccggcaa cttcagcggc gacgagcttc tatcctggtg cctccgccgc 1620
cctttcatag agcgccttcc accctcctcc tttactctcg tgacactgga gaccactgaa 1680
gccttcagct tggaggccga ggatgtcaag tatgtaaccc agcacttccg ctacaccttt 1740
gtcaatgaca aggtcaagcg cagtgcccgc tactactccc caggctggcg cacttgggct 1800
gctgttgcca tccagctagc ctggcgccga tatcgccatc gtctcacact cacgtccttg 1860
tcctttattc ggccccgccg cccactctca cggtgctctt ccttggggga ggatcgcctc 1920
cgcctctata cggcgttgct tacttctcca aagcccaacc acgaccactt tgatttttga 1980

<210> SEQ ID NO 13
<211> LENGTH: 2389
<212> TYPE: DNA
<213> ORGANISM: Gossypium hirsutum

<400> SEQUENCE: 13
cctccttcct tccttttcct tccattcgcc caattcctgg ctcgcccatg gttccactct 60
ttctcaccat gccttctcag tccaacttct ccctatcaag gtggtttgga ctttttcaac 120
ttccaaactc aatgccagag agatctgata atggtagtgt tagcggcgaa ggcaatgaag 180
aaaacccaat ttcctacacc gtagaatgtt acgcttgtac tcaagtcggt gttccagttt 240
ttcactccac cagctgtgac caagctcacc caccggaatg ggaagcctcc gctggttctt 300
ccctcgttcc aattcaagct cgtacggcct ccaaacagaa gaagactcaa cagcctgccg 360
cgcctaatac tcggcgacct tctggtccgt tcggtcgggt gcttgatcct aggaccaagc 420
gagtgcaaaa ctggaaccgg gctttcttat tggctcgtgc aatggcttta gccattgatc 480
ctttgttttt ctatgcttta tctataggaa gaggtgggtc gccgtgtttg tacatggatg 540
ggggcctcgc tgccatcgta accgtcctcc gcacgtgtgt ggacgccgtg catttgttcc 600
atctttggct tcagttcaga ctggcgtacg tgtcaaggga gtcgctggtc gtcggttgtg 660
gtaaactcgt gtgggacgca cgtgccatcg cttctcatta cgttcgttcc ctcaaaggtt 720
tctggtttga tgtctttgtg attctgccgg ttcctcaggc agtattttgg ttagttgtac 780
caaaattaat aagggaagag cagatcaaga ttattatgac aatactgtta ttaatcttct 840
tgttccaatt cttgccaaag gtttaccaca tcatttgctt aatgagaagg ctgcaaaagg 900
tcaccggtta catctttggc accatttggt ggggttttgg ccttaatctc attgcctact 960
tcatagcctc tcacgttgct ggagggtgct ggtatgtcct tgcaatacaa cgggtagcct 1020
catgtctgcg gcaacaatgc gcgagaaaca agcagtgcaa gctttcattg tcgtgctcgg 1080

-continued

```
aggaagtgtg ctaccaattc ttatttccag ctgaggcagt aggaaatact tgtggtggta   1140
actcaaccaa cgttattgga aaacctttat gtttagaggt tcatggacca ttcaattatg   1200
ggatatatca gtgggctctc cctgttgttt ctagcaattc tgttgctgtt aggatccttt   1260
atcccatcta ttggggctta atgtctctca gcacctttgg gaatgatctt gaaccaacaa   1320
gtcactggtt agaagtgatg ttcagtattt gcattgtgct tgctggattg atgctcttta   1380
ctttattgat tggaaacatt caggtattct tgcatgctgt catggcgaag aagaggaaaa   1440
tgcagctgag atgtcgagac atggaatggt ggatgaaacg ccggcaacta ccatcttgtt   1500
tgagacaacg agtccgccat tacgaacgcc aaaaatgggc gaccttgggc ggagaagacg   1560
aaatggaact gatcaaagac ttacccgaag gcctccggag agacattaaa cgcttccttt   1620
gccttgacct catcaagaag gttcctttat tccataactt gaatgatctt attctggata   1680
acatctgtga tcgagttaag ccgctcgtat tctctaaaga tgaaaagata attagagaag   1740
gtgatccagt acaaagaatg gtgtttgtcg ttcgtggacg tataaaacgt atccaaagcc   1800
ttagcaaagg cgtggttgcc acaagtttaa tcgagtcagg aggcttccta ggtgacgaat   1860
tgttgtcatg gtgtcttcgc cgaccattta tcaaccgtct tccagcctcg tccgcaacat   1920
ttgtttgtgt agagccgatt gaagcattca gtctcgactc aaaccatctc aaatacatta   1980
cagatcactt caggtataaa tttgccaatg agagacttaa aagaacagca agatactatt   2040
catcgaattg gcgaacatgg gcagccgtga atatacaact tggctggcgg cgttacagaa   2100
cgaggactcg aggtccaatg atttctgctg ccgaaaacgg caacagcagc gaccgccggt   2160
tgctgcaata cgctgccatg tttatgtcaa taaggccaca agatcatcta gaataaagaa   2220
aagccaattg ccttctgcaa ttcatttggg tcattatgta atctgtactg tcatttaata   2280
aagtttttca ttcaccatgg aaaccatttt gaacatagtt gtttgctcat tctgtactca   2340
tctgcttcaa gtacaagtca aaaaaaaaaa agaagaaaag gggggggaa               2389
```

<210> SEQ ID NO 14
<211> LENGTH: 2067
<212> TYPE: DNA
<213> ORGANISM: Gossypium hirsutum

<400> SEQUENCE: 14

```
atgccttctt ccatgtggag cgagctttgc ctgagaccct caccgcctcc tttcaatgtc     60
gccgccgacg caacccctgt cgtggaatgc tacgcatgta cccaagtcgg cgtcccagcc    120
ttccactcca ccagctgcga ccacgcccac caacaacccg aatgggaagc ctccgcgggc    180
tcttccctgg ttccaatcca acccacaaaa tcctcaccac cgccccgaca ttcttccgcg    240
ggttgcttcg ggacggttct ggacccaaga aagaaaccgg ttcagagatg gaaccgggtt    300
ctgttactgg cccggggaat ggctcttgcg gttgatccac tttacttcta tgctctgtcg    360
attggaagag gagggtggcc ttgcctgtac atggatggag ggttggccgg cggggtgacg    420
gtggttcgaa cgtgtcttga tatagtgcac ctgtggcacg tgtggcttca gttcaggctt    480
gcttacgtgt cgaaagagag tatggtgatt gggtgtggga aactggtgtg gaatgcacgt    540
gatattgctt ctcactatgt tcgttctttt aaaggctttt ggtttgatgc ctttgttatc    600
ctccctattc ctcagattgt ttattggttg gttttaccaa aactgatcag agaagagaga    660
atcaaactta taatgacagt aatcttatta atgtttttgt tccaattcct cccaaaagtt    720
taccactcca ttattttaat gagaagaatg cagaaggtta ctggatacat ctttggcacc    780
atttggtggg gttttggcct caatctcatt gcctatttca ttgcctctca tgttgctgga    840
```

ggttgttggt atgttcttgc aatacagcga gttgcttctt gtatccaaca acattgtgag 900
agaaacaact gcaacttatc tttgtcttgc tctgaggagg tgtgttatcg gtttctctca 960
tcacctacaa caattggaag tttgtgtggt cggaattcaa ctgctacgtt taggaagcca 1020
ctatgtttgg atgttaaagg tccgttcgcc tatggcatct acaagtgggc tctccctgtc 1080
atttctagta attcagttgc tgtcaaaatc ctttatccta tcttttgggg attaatgact 1140
ctcagcacct ttggaaatga tcttgagcct acgagtaatt ggctggaagt gtgcttcagt 1200
atttgcacgg tgcttagtgg attgttgctt ttcacccttt tgattggtaa tattcaggta 1260
cttttgcatg ctgtcatggc aaggaggcga aaaatgcagc tgagatgtcg agatttggag 1320
tggtggatga ggagacggca attgccgtct cgtttgaaac atcgagttcg acactatgag 1380
caccagagat gggcagctat gggaggagaa gatgagatgg aactaatcaa tgatttgcct 1440
gaaggtctta gaagagatat caaacgtcat ctttgtgttg acctaatcag aaaggtgcct 1500
ctctttcaaa acctggagga gctgattcta gacaacatat gtgatcgagt caagccactt 1560
gtattctcca aagatgaaaa gattatcaga gaaggagatc ctgttccaag aatgttattc 1620
atagtgtgtg gacgagtaaa acgtagccaa agcctgagca agggcatgac agcgacaagt 1680
tttattgaac cgggaggctt tcttggtgat gaactgctat cgtggtgtct tcgtcgccca 1740
tttctggaga gacttccagc ttcatccgct acatttgttt gcattgaacc aacagaagca 1800
tttgccctga aagcagacca tctgaagtac ataaccgatc acttccgcta caaattcgcg 1860
aatgagagac tgaagagaac agcaagattt tactcttcca actggagaac atgggctgct 1920
gttaacatac aacttgcttg gcgtagatac agaaaacgga tgaggcgtcc agcgatagct 1980
gtggtggaaa acggaagcac tgaacgtcgg cttttgcagt atgctgcaat gttcatgtca 2040
ttcagaccac atgatcatct tgaatag 2067

<210> SEQ ID NO 15
<211> LENGTH: 2893
<212> TYPE: DNA
<213> ORGANISM: Cucumis melo

<400> SEQUENCE: 15
gacatcacgg gaaaatggca aatataaata tcggcgccgg gtacaaaatc ggatcatccc 60
aatcggacgc gaacccctag cgcgatcatc accattattg tgatgtgccc ggctcacctg 120
tgccaggaac ccggtggccc cactacgaac aattgctcga gtcaatccgg taggtgtagc 180
cgtgtctgcg tagccgttcc ggggagccaa gggctcggca ccaccgcggc atcggtgcac 240
aaggacggcg cacgtacgcg ccacgtcctt gggccccggc gcagttgtac cctccatctc 300
tgtcctcttt acttgcccca tccatcccac gccgatcgcc aggcgccagc agcaggctag 360
ctctgctccg ccgctcactg ctcgctagct actggaccgc gcttccctct ctccatcgcg 420
ccggcgcgca cggctagctc tagctcccgg agccgccctt tcatggtccc cgccgtggtc 480
gggacgagat gcctccgctc gcattcctcc gccgctacct ccccgcgagg cttctcgcgc 540
gagcgtgcga tggtggagtc cgggggagcc cgggcgtggc gcgggacgag gaggccggag 600
gcagcggcgg actgagcggc cggtcggcgg gggcgccgtc cggggagtgc tacgcgtgca 660
cgcagcccgg ggtgccggcg ttccactcca cggcctgcga ccaggtgcac tcgccggact 720
gggacgccga cgcggggtcc tcgctggtgc cggtccaggc gcagcagcag gcccagccgg 780
cggcggcggc ggcgcagcac gcggcgcggt ggctgttcgg gcccgtgctg gacccgcgca 840

-continued

```
gcaagcgcgt gcagcgctgg aaccgctgga tcctgctcgg ccgcgccgcc gcgctggcgc    900
tggacccgct cttcttctac gcgctctcca tcggccgcgc cggccggccc tgcctctact    960
tggacgccgg cctcgccgcc gcggtcaccg cgctccggac ctgcgccgac gtcgcgcacc   1020
tcgcgcacgt gctcctgcag ttccgcctcg cctacgtctc ccgcgagtcc ctcgtcgtcg   1080
ggtgcggcaa gctcgtctgg gacgcccgcg ccatcgccgc gcactacgcc cgctccgtca   1140
agggcctctg cttcgacctc ttcgtcatcc tccccatccc gcaggtcatc ttctggttgg   1200
ttataccaaa gttaattagg gaagaacgtg ttaggcttat catgacgata ctgctactca   1260
tgttcatatt tcaatttctc cccaaggtct accatagtat acacatcatg aggaaaatgc   1320
agaaggtgac gggttacatc tttggatcga tatggtgggg atttggttta aatctatttg   1380
cctatttcat tgcttctcat attgcaggtg ggtgctggta tgttcttgca atccagcgca   1440
ttgcttcctg cctccaggaa gaatgcaaga aaaacaatag ttgtgatcta atatcactag   1500
cttgttcgaa ggagatatgc tttcaccctc cttggtcttc gaatgttaat gggttcgcat   1560
gtgatacgaa catgacctcc tttagtcaac gaaatgtgtc tacttgttta agtggtaaag   1620
ggtcgtttgc ttatggaatc tatttggggg ctcttcctgt tatatcgagc aattcgcttg   1680
ctgtcaaaat tctctatcct atattttggg gactcatgac actcagtact tttggtaacg   1740
atcttgcccc aacaagcaat ggtattgagg tgatattcag cataatcaat gtcctcagtg   1800
gcctgatgct cttcacattg ctgatcggaa acatacaggt atttctgcac gcggtcctgg   1860
caaggaagcg gaagatgcag ctgcggttcc gagacatgga atggtggatg agacggaggc   1920
agctgccgtc tcggctgagg cagagggtgc gcaaatatga gcgcgaacgc tgggccgccg   1980
tcacgggaga cgaggagatg gagatgatca aggatctgcc tgaaggactg aggcgggaca   2040
tcaagcgcta cctctgcctc gagctggtta agcaggttcc gctgttccat ggcatggacg   2100
atctgatcct ggataacatc tgcgaccggc tgcggccact ggtgttctcc agcggggaga   2160
aggtgatccg agagggcgac cccgtgcagc gcatggtgtt catcctgcag ggcaagctcc   2220
ggagcacgca gccgctgacc aagggcgtgg tggcaacgtg catgctaggg gcgggcaact   2280
tcctaggcga cgagctgctg tcgtggtgcc tgcgccgccc cttcgtggac cggctccccg   2340
cgtcgtcggc cacgttcgag tgcgtggagg cggcgcaggc gttctgcctc gacgcgccgg   2400
acctgcggtt catcaccgag cacttccgct acaagttcgc caacgagaag ctcaggcgca   2460
cggcgcggta ctactcgtcc aactggcgga cgtgggccgc cgtcaacatc cagctcgcgt   2520
ggcgcaggta tagggcccgg gcatcgacgg acctggcggc gatggccgcg ccgccgttgg   2580
cgggcggacc cgacgacggg gaccggcggc tcagacacta cgcggccatg ttcatgtcgc   2640
tccggccgca tgaccaccta gagtgatcag gaggggggac gggaccatcc tagctgtgcc   2700
ggccgggtca tggtgtctgt acagtgtaca ctagtggtat gttgttgtca tcttctgcgt   2760
gagtgaactg gtggttcggg atttgtcatt taaagaaggt caataatgga gaaatagttt   2820
cttagcccga ttcaattgtc ttcctttcac caagaataaa aattacttct gccggactgc   2880
ctctccgcgt tgg                                                      2893
```

<210> SEQ ID NO 16
<211> LENGTH: 2446
<212> TYPE: DNA
<213> ORGANISM: Zea mays

<400> SEQUENCE: 16

```
atgccttccc tctccttcct ccgcttcctc tccgggaggt cgctcgcgga tgtgtgtgat     60
```

```
ggggtgaaga ggaggcttgg attgggggat gatgaaggcc gggacgagga ggctggtctg    120
gccggagggt cgagccgtcc ggcggcggcg gcggcggtgg cggggcctcc cggcgagtgc    180
tacgcgtgca cgcagcccgg ggtgccgtcg ttccactcca cgacgtgcga ccaggtgcac    240
tcgccggact gggacgcgga cgcgggctcg tcgctagtgc cggtccaggc gcagccgtcg    300
gcggcgcacc acgcggcggc ggcggcggcg cggtgggtgt tcggcccggt gctcgacccg    360
cggagcaagc gcgtgcagcg gtggaaccgg tggatcctgc tggcccgcgc cgccgcgctg    420
gcggtggacc cgctcttctt ctacgcgctc tccatcggcc gcgccgggca gccgtgcgtg    480
tacatggacg ccggcctcgc cgccgccgtc acggcgctcc gcaccgccgc cgacctggcg    540
cacctcgccc acgtcctcct ccagttccgc gtcgcctacg tctcccgcga gtccctcgtc    600
gtcggctgcg gcaagctcgt ctgggacccc cgcgccatcg ccgctcacta cgcccgctcc    660
ctcaagggcc tctggttcga tctcttcgtc atcctgccca tcccacaggt catcttctgg    720
ctagtcatac cgaagttaat cagagaagag caaatcaaac ttatcatgac aatgctgctg    780
ctcttattct tgctgcaatt tctccccaag gtgtaccaca gtatttatat catgaggaaa    840
atgcagaagg tgactggtta catctttgga acgatatggt ggggattcgg gcttaatctt    900
ttcgcctatt tcattgcttc tcacatcgca ggtggatgtt ggtatgtcct tgcgattcag    960
cgtgtcgcct cctgcctcca ggaggaatgc aagataaaga acacttgcaa cctaacatca   1020
cttgcttgct ccaaggagat gtgttttcac cttccttggt cagataagaa tggactggca   1080
tgcaacttga cttcttttgg ccaacaaaac attccagact gtctaagcgg caatgggccc   1140
tttgcttatg gaatctacaa aggggctctg cctgttattt ccagcaattc acttgctgtt   1200
aaaatactct accctatatt ttggggactc atgactctca gtacttttgg taatgatctt   1260
gagcctacaa gcaattggct tgaggtgatt ttcagcataa tcaatgtact tagcgggttg   1320
atgctcttca cattgctgat tggaaacata caggtcttct tgcatgctgt cttagcaaga   1380
aagcgaaaga tgcagctgcg gttccgggac atggaatggt ggatgcggcg gaggcagttg   1440
ccgtcccgcc tgaggcagag ggtccggaag tacgagcgtg aacgctgggc ggccatcacg   1500
ggagatgagg agatggagat gatcaaggac ctgcctgaag ggctcaggcg agacatcaaa   1560
cgctacctct gcctcgagct agttaaacag gttcctctgt tccatggcat ggacgatctc   1620
atcctggaca acatctgcga caggctgagg ccgctggtgt tctccagcgg cgagaaggtg   1680
atccgggagg gcgacccggt gcagcggatg gtgttcgtcc tccaggggaa gctccggagc   1740
acgcagccgc tggccaaggg cgtggtggcg acgtgtatgc tcggcgccgg caacttcctc   1800
ggcgacgagc tgctgtcgtg gtgcctccgg cggccgtccc tggaccggct gccggcgtcg   1860
tcggcgacgt tcgagtgcgt cgagacggcg caggcgttct gcctcgacgc ccccgacctt   1920
cgcttcatca cggagcagtt ccggtacaag ttcgccaacg agaagctcaa gcggacggcg   1980
cgctactact cctccaactg gcggacgtgg gcggccgtca acatccagct cgcgtggcgc   2040
cggtacaagg caaggacgac gaccgacctg gcgtcggcgg cgcagccgcc gtccgccggc   2100
gggcccgacg acggggaccg ccggctccgc cattacgcgg ccatgttcat gtcgctcagg   2160
ccacacgatc acctcgagtg agagcagccg tggattggga ccgagagtga cggggcatat   2220
gcaatgcaac cgtacgcgca tggagcggac caccctgcgc cggccatata tcattgattc   2280
cattgtagta cgatcgtatc ctgctgccgg tcttgacaat tgattagcat ttgtcattgt   2340
ataagatgac caataatggt tatgatgtag ttccaacaaa ataatgcaat gtgctccttg   2400
```

-continued gttggcgccg caaatcggat cattgagaag gacatcactg ggaata 2446

<210> SEQ ID NO 17
<211> LENGTH: 1190
<212> TYPE: DNA
<213> ORGANISM: Oryza sativa

<400> SEQUENCE: 17
cgaagcctgc cggcgtacgc caggtccagg agagggatgg cgctcgactt cttcgtcatc 60
ctccccgtga tgcagatggt ggtttgggtg gcggcgccgg cgatgatccg tgcggggtcg 120
acgacggcgg tgatgacggt gctgctggtg gcgttcctgc tggagtacct gcctaagatc 180
taccactccg tctccttcct ccggcggacg caggacaagt ccggccacat cttcggcacc 240
atctggtggg gcatcgtgct taacctcatg gcctacttcg tcgccgccca cgcggtgggc 300
gcgtgctggt acctgctcgg ggtgcagagg gccaccaagt gcctcaagga gcagtgctcc 360
atctccgggc cgccggggtg cgcgtcgggg ccgctggcgt gccccagccc tctctactac 420
ggcggcgccg gcgccgcggc gtccgtcgcc ggcgacaggc tcgcgtgggc cacagacccc 480
cccgccggga gcatgtgcct cgtgagcggt gacaagtacc agttcggggc gtacaagtgg 540
acggtgatgc tggtggccaa cacgagccgg ctggagaaga tgctgctccc catattctgg 600
ggcctcatga cgctgagcac gttcggcaac ctggagagca cgacggagtg gctggagatc 660
gtgttcaaca tcgtgaccat cacgggcggg ctcatcctgg tcaccatgct catcggcaac 720
atcaaggcgt tcctgaacgc gaccacgtcc aagaagcagg cgatgcacac gcggctgcgg 780
agcctcgagt ggtggatgaa gcgcaaggag ctgccgcaga gctaccggca ccgggtgcgg 840
cagttcgagc ggcagcggtg ggcggccacc cgcggcgtgg acgagtgcca gatcgtgcgc 900
gacctccccg aggccctccg ccgcgacatc aaagtaccac ctctgcctcg acctcgtccg 960
ccaggtgccg ctcttccagc acatggacga cctcgtcctc gagaacatgt gcgaccgcgt 1020
ccgctccctc atctacccca agggcgagac catccgtccg ggaggggccc ccggtgcagc 1080
ggatggtgtt catcgtgcgg gggcacctgg agtgcaggca ggagctgcgg aacggggcga 1140
cgagctgctg catgctgggg ccgggcaact tcacgggcga cgagctgctg 1190

<210> SEQ ID NO 18
<211> LENGTH: 2169
<212> TYPE: DNA
<213> ORGANISM: Gossypium hirsutum

<400> SEQUENCE: 18
atggttccac tctttctcac catgccttct cagtccaact tctccctatc aaggtggttt 60
ggactttttc aacttccaaa ctcaatgcca gagagatctg ataatggtag tgttagcggc 120
gaaggcaatg aagaaaaccc aatttcctac accgtagaat gttacgcttg tactcaagtc 180
ggtgttccag tttttcactc caccagctgt gaccaagctc acccaccgga atgggaagcc 240
tccgctggtt cttccctcgt tccaattcaa gctcgtacgg cctccaaaca gaagaagact 300
caacagcctg ccgcgcctaa tactcggcga ccttctggtc cgttcggtcg ggtgcttgat 360
cctaggacca agcgagtgca aaactggaac cgggctttct tattggctcg tgcaatggct 420
ttagccattg atcctttgtt tttctatgct ttatctatag gaagaggtgg gtcgccgtgt 480
ttgtacatgg atgggggcct cgctgccatc gtaaccgtcc tccgcacgtg tgtggacgcc 540
gtgcatttgt tccatctttg gcttcagttc agactggcgt acgtgtcaag ggagtcgctg 600
gtcgtcggtt gtggtaaact cgtgtgggac gcacgtgcca tcgcttctca ttacgttcgt 660

-continued

```
tccctcaaag gtttctggtt tgatgtcttt gtgattctgc cggttcctca ggcagtattt    720

tggttagttg taccaaaatt aataagggaa gagcagatca agattattat gacaatactg    780

ttattaatct tcttgttcca attcttgcca aaggtttacc acatcatttg cttaatgaga    840

aggctgcaaa aggtcaccgg ttacatcttt ggcaccattt ggtggggttt tggccttaat    900

ctcattgcct acttcatagc ctctcacgtt gctggagggt gctggtatgt ccttgcaata    960

caacgggtag cctcatgtct gcggcaacaa tgcgcgagaa acaagcagtg caagctttca   1020

ttgtcgtgct cggaggaagt gtgctaccaa ttcttatttc cagctgaggc agtaggaaat   1080

acttgtggtg gtaactcaac caacgttatt ggaaaacctt tatgtttaga ggttcatgga   1140

ccattcaatt atgggatata tcagtgggct ctccctgttg tttctagcaa ttctgttgct   1200

gttaggatcc tttatcccat ctattggggc ttaatgtctc tcagcacctt tgggaatgat   1260

cttgaaccaa caagtcactg gttagaagtg atgttcagta tttgcattgt gcttgctgga   1320

ttgatgctct ttactttatt gattggaaac attcaggtat tcttgcatgc tgtcatggcg   1380

aagaagagga aaatgcagct gagatgtcga gacatggaat ggtggatgaa acgccggcaa   1440

ctaccatctt gtttgagaca acgagtccgc cattacgaac gccaaaaatg ggcgaccttg   1500

ggcggagaag acgaaatgga actgatcaaa gacttacccg aaggcctccg gagagacatt   1560

aaacgcttcc tttgccttga cctcatcaag aaggttcctt tattccataa cttgaatgat   1620

cttattctgg ataacatctg tgatcgagtt aagccgctcg tattctctaa agatgaaaag   1680

ataattagag aaggtgatcc agtacaaaga atggtgtttg tcgttcgtgg acgtataaaa   1740

cgtatccaaa gccttagcaa aggcgtggtt gccacaagtt taatcgagtc aggaggcttc   1800

ctaggtgacg aattgttgtc atggtgtctt cgccgaccat ttatcaaccg tcttccagcc   1860

tcgtccgcaa catttgtttg tgtagagccg attgaagcat tcagtctcga ctcaaaccat   1920

ctcaaataca ttacagatca cttcaggtat aaatttgcca atgagagact taaaagaaca   1980

gcaagatact attcatcgaa ttggcgaaca tgggcagccg tgaatataca acttggctgg   2040

cggcgttaca gaacgaggac tcgaggtcca atgatttctg ctgccgaaaa cggcaacagc   2100

agcgaccgcc ggttgctgca atacgctgcc atgtttatgt caataaggcc acaagatcat   2160

ctagaataa                                                           2169
```

<210> SEQ ID NO 19
<211> LENGTH: 2067
<212> TYPE: DNA
<213> ORGANISM: Cucumis sativus

<400> SEQUENCE: 19

```
atgccttctt ccatgtggag cgagctttgc ctgagaccct caccgcctcc tttcaatgtc     60

gccgccgacg caacccctgt cgtggaatgc tacgcatgta cccaagtcgg cgtcccagcc    120

ttccactcca ccagctgcga ccacgcccac caacaacccg aatgggaagc ctccgcgggc    180

tcttccctgg ttccaatcca acccacaaaa tcctcaccac cgccccgaca ttcttccgcg    240

ggttgcttcg ggacggttct ggacccaaga aagaaaccgg ttcagagatg gaaccgggtt    300

ctgttactgg cccggggaat ggctcttgcg gttgatccac tttacttcta tgctctgtcg    360

attggaagag gagggtggcc ttgcctgtac atggatggag ggttggccgg cggggtgacg    420

gtggttcgaa cgtgtcttga tatagtgcac ctgtggcacg tgtggcttca gttcaggctt    480

gcttacgtgt cgaaagagag tatggtgatt gggtgtggga aactggtgtg gaatgcacgt    540
```

-continued

```
gatattgctt ctcactatgt tcgttctttt aaaggctttt ggtttgatgc ctttgttatc    600
ctccctattc ctcagattgt ttattggttg gttttaccaa aactgatcag agaagagaga    660
atcaaactta taatgacagt aatcttatta atgtttttgt tccaattcct cccaaaagtt    720
taccactcca ttattttaat gagaagaatg cagaaggtta ctggatacat ctttggcacc    780
atttggtggg gttttggcct caatctcatt gcctatttca ttgcctctca tgttgctgga    840
ggttgttggt atgttcttgc aatacagcga gttgcttctt gtatccaaca acattgtgag    900
agaaacaact gcaacttatc tttgtcttgc tctgaggagg tgtgttatcg gtttctctca    960
tcacctacaa caattggaag tttgtgtggt cggaattcaa ctgctacgtt taggaagcca   1020
ctatgtttgg atgttaaagg tccgttcgcc tatggcatct acaagtgggc tctccctgtc   1080
atttctagta attcagttgc tgtcaaaatc ctttatccta tcttttgggg attaatgact   1140
ctcagcacct ttggaaatga tcttgagcct acgagtaatt ggctggaagt gtgcttcagt   1200
atttgcacgg tgcttagtgg attgttgctt ttcacccttt tgattggtaa tattcaggta   1260
cttttgcatg ctgtcatggc aaggaggcga aaaatgcagc tgagatgtcg agatttggag   1320
tggtggatga ggagacggca attgccgtct cgtttgaaac atcgagttcg acactatgag   1380
caccagagat gggcagctat gggaggagaa gatgagatgg aactaatcaa tgatttgcct   1440
gaaggtctta gaagagatat caaacgtcat ctttgtgttg acctaatcag aaaggtgcct   1500
ctctttcaaa acctggagga gctgattcta gacaacatat gtgatcgagt caagccactt   1560
gtattctcca aagatgaaaa gattatcaga gaaggagatc ctgttccaag aatgttattc   1620
atagtgtgtg gacgagtaaa acgtagccaa agcctgagca agggcatgac agcgacaagt   1680
tttattgaac cgggaggctt tcttggtgat gaactgctat cgtggtgtct tcgtcgccca   1740
tttctggaga gacttccagc ttcatccgct acatttgttt gcattgaacc aacagaagca   1800
tttgccctga aagcagacca tctgaagtac ataaccgatc acttccgcta caaattcgcg   1860
aatgagagac tgaagagaac agcaagattt tactcttcca actggagaac atgggctgct   1920
gttaacatac aacttgcttg gcgtagatac agaaaacgga tgaggcgtcc agcgatagct   1980
gtggtggaaa acggaagcac tgaacgtcgg cttttgcagt atgctgcaat gttcatgtca   2040
ttcagaccac atgatcatct tgaatag                                       2067
```

```
<210> SEQ ID NO 20
<211> LENGTH: 2178
<212> TYPE: DNA
<213> ORGANISM: Zea mays

<400> SEQUENCE: 20

atgcctccgc tcgcattcct ccgccgctac ctccccgcga ggcttctcgc gcgagcgtgc     60
gatggtggag tccgggggag cccgggcgtg gcgcgggacg aggaggccgg aggcagcggc    120
ggactgagcg gccggtcggc gggggcgccg tccggggagt gctacgcgtg cacgcagccc    180
ggggtgccgg cgttccactc cacggcctgc gaccaggtgc actcgccgga ctgggacgcc    240
gacgcggggt cctcgctggt gccggtccag gcgcagcagc aggcccagcc ggcggcggcg    300
gcggcgcagc acgcggcgcg gtggctgttc gggcccgtgc tggacccgcg cagcaagcgc    360
gtgcagcgct ggaaccgctg gatcctgctc ggccgcgccg ccgcgctggc gctggacccg    420
ctcttcttct acgcgctctc catcggccgc gccggccggc cctgcctcta cttggacgcc    480
ggcctcgccg ccgcggtcac cgcgctccgg acctgcgccg acgtcgcgca cctcgcgcac    540
gtgctcctgc agttccgcct cgcctacgtc tcccgcgagt ccctcgtcgt cgggtgcggc    600
```

aagctcgtct gggacgcccg cgccatcgcc gcgcactacg cccgctccgt caagggcctc 660
tgcttcgacc tcttcgtcat cctccccatc ccgcaggtca tcttctggtt ggttatacca 720
aagttaatta gggaagaacg tgttaggctt atcatgacga tactgctact catgttcata 780
tttcaatttc tccccaaggt ctaccatagt atacacatca tgaggaaaat gcagaaggtg 840
acgggttaca tctttggatc gatatggtgg ggatttggtt taaatctatt tgcctatttc 900
attgcttctc atattgcagg tgggtgctgg tatgttcttg caatccagcg cattgcttcc 960
tgcctccagg aagaatgcaa gaaaaacaat agttgtgatc taatatcact agcttgttcg 1020
aaggagatat gctttcaccc tccttggtct tcgaatgtta atgggttcgc atgtgatacg 1080
aacatgacct cctttagtca acgaaatgtg tctacttgtt taagtggtaa agggtcgttt 1140
gcttatggaa tctatttggg ggctcttcct gttatatcga gcaattcgct tgctgtcaaa 1200
attctctatc ctatattttg gggactcatg acactcagta cttttggtaa cgatcttgcc 1260
ccaacaagca atggtattga ggtgatattc agcataatca atgtcctcag tggcctgatg 1320
ctcttcacat tgctgatcgg aaacatacag gtatttctgc acgcggtcct ggcaaggaag 1380
cggaagatgc agctgcggtt ccgagacatg gaatggtgga tgagacggag gcagctgccg 1440
tctcggctga ggcagagggt gcgcaaatat gagcgcgaac gctgggccgc cgtcacggga 1500
gacgaggaga tggagatgat caaggatctg cctgaaggac tgaggcggga catcaagcgc 1560
tacctctgcc tcgagctggt taagcaggtt ccgctgttcc atggcatgga cgatctgatc 1620
ctggataaca tctgcgaccg gctgcggcca ctggtgttct ccagcgggga gaaggtgatc 1680
cgagagggcg accccgtgca gcgcatggtg ttcatcctgc agggcaagct ccggagcacg 1740
cagccgctga ccaagggcgt ggtggcaacg tgcatgctag gggcgggcaa cttcctaggc 1800
gacgagctgc tgtcgtggtg cctgcgccgc cccttcgtgg accggctccc cgcgtcgtcg 1860
gccacgttcg agtgcgtgga ggcggcgcag gcgttctgcc tcgacgcgcc ggacctgcgg 1920
ttcatcaccg agcacttccg ctacaagttc gccaacgaga agctcaggcg cacggcgcgg 1980
tactactcgt ccaactggcg gacgtgggcc gccgtcaaca tccagctcgc gtggcgcagg 2040
tatagggccc gggcatcgac ggacctggcg gcgatggccg cgccgccgtt ggcgggcgga 2100
cccgacgacg gggaccggcg gctcagacac tacgcggcca tgttcatgtc gctccggccg 2160
catgaccacc tagagtga 2178

<210> SEQ ID NO 21
<211> LENGTH: 2145
<212> TYPE: DNA
<213> ORGANISM: Glycine max

<400> SEQUENCE: 21
atgcacaaca ccttctcctc tctccttcgt tggattagca aaaagttgcg acgaaggaat 60
tcaattagca atggtgacag tggcagcgac agcttccaga acggtgctgc cacagttgtg 120
gatgacaatc catttagcag cggggtggag tgttacgcct gcacgcaagt aggtgtgccg 180
gtgtttcact ccaccagctg cgacagtgcc ttccaccagt tgcagtggga ggcttcggct 240
gggtcgtctc tggttcccat ccagagccga cccaacaagg tcctcggctt tcggaccgtg 300
tccggatcaa gtcgggggcc gttcgggcgg gttctggatc cgagaagcaa gcgcgtgcag 360
aggtggaacc gcgcgctgct cctggcgcgt ggggtggcgc tggcgataga cccgctgttc 420
ttctactcgc tgtcgatagg aagggagggg tcgccgtgct tgtacatgga cggagggctg 480

```
gcggcgatgg tgacggtggc gcgcacgtgc gtggacgccg tgcacctctt gcacgtgtgg    540

ctgcagttca ggctggcgta cgtatcgcgg gagtcgctgg tggtggggtg cgggaaactc    600

gtgtgggacg cgcgtgagat cgcgtcgcat tacctgcgat cgttgaaggg attctggttc    660

gacgcattcg tgatcctccc agtcccccag gttgtgtttt ggttgttagt gccaaaattg    720

ctaagagaag agaaaattaa aatcattatg acaataatgc tattgatttt tttgttccaa    780

tttctcccta aggtttacca tagcatctgc atgatgagaa gaatgcaaaa agtcacaggc    840

tacatcttcg gcaccatttg gtggggtttt ggtctcaatc tcatagctta ttttattgct    900

tctcatgttg ctggagggtg ctggtatgtc cttgcaattc aacgtgttgc gtcgtgcctc    960

cggcagcagt gtgagagaac taatggatgc aatctctctg tgtcatgctc agaggagata   1020

tgctaccagt ctttgttacc agctagcgcg ataggagatt catgtggtgg aaactcaaca   1080

gtggtaagaa agcctctgtg cttagatgtt gaaggacctt tcaaatatgg gatctaccaa   1140

tgggcacttc ctgtcatatc cagcaactct ttggctgtaa agattcttta tcccattttt   1200

tggggtttga tgaccctcag cactttcgga aatgatcttg aacccacaag ccactggcta   1260

gaagtgattt tcagtatatg catagtactc agtggactat tgcttttcac attattgatt   1320

ggtaacattc aggtattctt acatgcagtc atggcaaaga agagaaagat gcagctgaga   1380

tgtcgtgaca tggaatggtg gatgaggagg aggcagttgc catcgcgatt aagacagaga   1440

gttcgccatt ttgaacgtca gagatgggca gcaatgggag gagaagatga gatggaaatg   1500

atcaaagact tgccagaggg gctgaggagg gacatcaagc gccatctttg cctcgatctc   1560

attagaaagg ttcctctatt ccacaacttg gatgatctta ttcttgacaa catctgtgac   1620

agggtgaaac ccctagtctt ctctaaagat gaaaagataa tcagagaagg tgatcctgta   1680

ccaaggatgg tgttcatcgt ccgagggcgc ataaaacgca accaaagcct tagcaaaggc   1740

atggtagcct caagcatcct tgagccagga gggtttttgg gtgacgagct gctttcatgg   1800

tgccttcgca ggccgtttat cgatagactt ccggcctcct cggctacatt tgtgtgtctt   1860

gaatcatcag aagcctttgg ccttgatgcc aatcacttga ggtacatcac tgatcacttc   1920

cggtacaaat ttgcgaacga gaggctgaag agaacagcaa gatattattc atccaattgg   1980

agaacctggg ctgctgtcaa cattcaattt gcttggagac gttacaggca gaggactaaa   2040

ggtccagtga cccctgtaag ggacactaat ggaggcactg aacgcaggct cttgcaatat   2100

gctgcaatgt tcatgtcaat aaggccacat gaccaccttg aatga                    2145
```

<210> SEQ ID NO 22
<211> LENGTH: 2181
<212> TYPE: DNA
<213> ORGANISM: Oryza sativa

<400> SEQUENCE: 22

```
atgccttccc tctccttcct ccgcttcctc tccgggaggt cgctcgcgga tgtgtgtgat     60

ggggtgaaga ggaggcttgg attgggggat gatgaaggcc gggacgagga ggctggtctg    120

gccggagggt cgagccgtcc ggcggcggcg gcggcggtgg cggggcctcc cggcgagtgc    180

tacgcgtgca cgcagcccgg ggtgccgtcg ttccactcca cgacgtgcga ccaggtgcac    240

tcgccggact gggacgcgga cgcgggctcg tcgctagtgc cggtccaggc gcagccgtcg    300

gcggcgcacc acgcggcggc ggcggcggcg cggtgggtgt tcggcccggt gctcgacccg    360

cggagcaagc gcgtgcagcg gtggaaccgg tggatcctgc tggcccgcgc cgccgcgctg    420

gcggtggacc cgctcttctt ctacgcgctc tccatcggcc gcgccgggca gccgtgcgtg    480
```

tacatggacg ccggcctcgc cgccgccgtc acggcgctcc gcaccgccgc cgacctggcg 540
cacctcgccc acgtcctcct ccagttccgc gtcgcctacg tctcccgcga gtccctcgtc 600
gtcggctgcg gcaagctcgt ctgggacccc cgcgccatcg ccgctcacta cgcccgctcc 660
ctcaagggcc tctggttcga tctcttcgtc atcctgccca tcccacaggt catcttctgg 720
ctagtcatac cgaagttaat cagagaagag caaatcaaac ttatcatgac aatgctgctg 780
ctcttattct tgctgcaatt tctccccaag gtgtaccaca gtatttatat catgaggaaa 840
atgcagaagg tgactggtta catctttgga acgatatggt ggggattcgg gcttaatctt 900
ttcgcctatt tcattgcttc tcacatcgca ggtggatgtt ggtatgtcct tgcgattcag 960
cgtgtcgcct cctgcctcca ggaggaatgc aagataaaga acacttgcaa cctaacatca 1020
cttgcttgct ccaaggagat gtgttttcac cttccttggt cagataagaa tggactggca 1080
tgcaacttga cttcttttgg ccaacaaaac attccagact gtctaagcgg caatgggccc 1140
tttgcttatg gaatctacaa aggggctctg cctgttattt ccagcaattc acttgctgtt 1200
aaaatactct accctatatt ttggggactc atgactctca gtacttttgg taatgatctt 1260
gagcctacaa gcaattggct tgaggtgatt ttcagcataa tcaatgtact tagcgggttg 1320
atgctcttca cattgctgat tggaaacata caggtcttct tgcatgctgt cttagcaaga 1380
aagcgaaaga tgcagctgcg gttccgggac atggaatggt ggatgcggcg gaggcagttg 1440
ccgtcccgcc tgaggcagag ggtccggaag tacgagcgtg aacgctgggc ggccatcacg 1500
ggagatgagg agatggagat gatcaaggac ctgcctgaag ggctcaggcg agacatcaaa 1560
cgctacctct gcctcgagct agttaaacag gttcctctgt tccatggcat ggacgatctc 1620
atcctggaca acatctgcga caggctgagg ccgctggtgt tctccagcgg cgagaaggtg 1680
atccgggagg gcgacccggt gcagcggatg gtgttcgtcc tccaggggaa gctccggagc 1740
acgcagccgc tggccaaggg cgtggtggcg acgtgtatgc tcggcgccgg caacttcctc 1800
ggcgacgagc tgctgtcgtg gtgcctccgg cggccgtccc tggaccggct gccggcgtcg 1860
tcggcgacgt tcgagtgcgt cgagacggcg caggcgttct gcctcgacgc ccccgacctt 1920
cgcttcatca cggagcagtt ccggtacaag ttcgccaacg agaagctcaa gcggacggcg 1980
cgctactact cctccaactg gcggacgtgg gcggccgtca acatccagct cgcgtggcgc 2040
cggtacaagg caaggacgac gaccgacctg gcgtcggcgg cgcagccgcc gtccgccggc 2100
gggcccgacg acggggaccg ccggctccgc cattacgcgg ccatgttcat gtcgctcagg 2160
ccacacgatc acctcgagtg a 2181

<210> SEQ ID NO 23
<211> LENGTH: 1193
<212> TYPE: DNA
<213> ORGANISM: Triticum aestivum

<400> SEQUENCE: 23
cgcgaagcct gccggcgtac gccaggtcca ggagagggat ggcgctcgac ttcttcgtca 60
tcctccccgt gatgcagatg gtggtttggg tggcggcgcc ggcgatgatc cgtgcggggt 120
cgacgacggc ggtgatgacg gtgctgctgg tggcgttcct gctggagtac ctgcctaaga 180
tctaccactc cgtctccttc ctccggcgga cgcaggacaa gtccggccac atcttcggca 240
ccatctggtg gggcatcgtg cttaacctca tggcctactt cgtcgccgcc cacgcggtgg 300
gcgcgtgctg gtacctgctc ggggtgcaga gggccaccaa gtgcctcaag gagcagtgct 360

-continued

```
ccatctccgg gccgccgggg tgcgcgtcgg ggccgctggc gtgccccagc cctctctact    420
acggcggcgc cggcgccgcg gcgtccgtcg ccggcgacag gctcgcgtgg gccacagacc    480
cccccgccgg gagcatgtgc ctcgtgagcg gtgacaagta ccagttcggg gcgtacaagt    540
ggacggtgat gctggtggcc aacacgagcc ggctggagaa gatgctgctc cccatattct    600
ggggcctcat gacgctgagc acgttcggca acctggagag cacgacggag tggctggaga    660
tcgtgttcaa catcgtgacc atcacgggcg ggctcatcct ggtcaccatg ctcatcggca    720
acatcaaggc gttcctgaac gcgaccacgt ccaagaagca ggcgatgcac acgcggctgc    780
ggagcctcga gtggtggatg aagcgcaagg agctgccgca gagctaccgg caccgggtgc    840
ggcagttcga gcggcagcgg tgggcggcca cccgcggcgt ggacgagtgc cagatcgtgc    900
gcgacctccc cgaggccctc cgccgcgaca tcaaagtacc acctctgcct cgacctcgtc    960
cgccaggtgc cgctcttcca gcacatggac gacctcgtcc tcgagaacat gtgcgaccgc   1020
gtccgctccc tcatctaccc caagggcgag accatccgtc cgggaggggc ccccggtgca   1080
gcggatggtg ttcatcgtgc gggggcacct ggagtgcagg caggagctgc ggaacggggc   1140
gacgagctgc tgcatgctgg ggccgggcaa cttcacgggc gacgagctgc tgt          1193
```

<210> SEQ ID NO 24
<211> LENGTH: 1190
<212> TYPE: DNA
<213> ORGANISM: Triticum aestivum

<400> SEQUENCE: 24

```
cgaagcctgc cggcgtacgc caggtccagg agagggatgg cgctcgactt cttcgtcatc     60
ctccccgtga tgcagatggt ggtttgggtg gcggcgccgg cgatgatccg tgcggggtcg    120
acgacggcgg tgatgacggt gctgctggtg gcgttcctgc tggagtacct gcctaagatc    180
taccactccg tctccttcct ccggcggacg caggacaagt ccggccacat cttcggcacc    240
atctggtggg gcatcgtgct taacctcatg gcctacttcg tcgccgccca cgcggtgggc    300
gcgtgctggt acctgctcgg ggtgcagagg gccaccaagt gcctcaagga gcagtgctcc    360
atctccgggc cgccggggtg cgcgtcgggg ccgctggcgt gccccagccc tctctactac    420
ggcggcgccg gcgccgcggc gtccgtcgcc ggcgacaggc tcgcgtgggc cacagacccc    480
cccgccggga gcatgtgcct cgtgagcggt gacaagtacc agttcggggc gtacaagtgg    540
acggtgatgc tggtggccaa cacgagccgg ctggagaaga tgctgctccc catattctgg    600
ggcctcatga cgctgagcac gttcggcaac ctggagagca cgacggagtg gctggagatc    660
gtgttcaaca tcgtgaccat cacgggcggg ctcatcctgg tcaccatgct catcggcaac    720
atcaaggcgt tcctgaacgc gaccacgtcc aagaagcagg cgatgcacac gcggctgcgg    780
agcctcgagt ggtggatgaa gcgcaaggag ctgccgcaga gctaccggca ccgggtgcgg    840
cagttcgagc ggcagcggtg ggcggccacc cgcggcgtgg acgagtgcca gatcgtgcgc    900
gacctccccg aggccctccg ccgcgacatc aaagtaccac ctctgcctcg acctcgtccg    960
ccaggtgccg ctcttccagc acatggacga cctcgtcctc gagaacatgt gcgaccgcgt   1020
ccgctccctc atctacccca agggcgagac catccgtccg ggaggggccc ccggtgcagc   1080
ggatggtgtt catcgtgcgg gggcacctgg agtgcaggca ggagctgcgg aacggggcga   1140
cgagctgctg catgctgggg ccgggcaact tcacgggcga cgagctgctg              1190
```

<210> SEQ ID NO 25
<211> LENGTH: 2629

<212> TYPE: DNA
<213> ORGANISM: Gossypium hirsutum

<400> SEQUENCE: 25

```
tccacgcgtc cgattatgtc ctttctacat atttcatcaa tctttgcctc ttaaacaatt     60

ctaacttata ttccccttct tcttcaaacc tttaatggcc atctctcctt agcccccaaa    120

aatatcaatc aaaatttttt tttcttttgc gatggcaagt gaacatgaat tttatccttc    180

acgtgcaacg cccatgcaat actttacgga tgaagacgaa ggagaagaag aaggaggaga    240

aatagaagaa gaatcgacgg acgacgaagt ttgcaaagaa gaagagaaag agaattcaag    300

tgactggagg agtttgtatt tgatgtgcgg cggtcgccgc ggcggtgggc gtcgccgtaa    360

aacttggtca ctggggcaag tttttttcga cccgagggcc aaatgggttc aagaatggaa    420

tagggttttc ctcctggtat gcgcgacggg actgttcgtg gacccattgt tcttttacgc    480

cctgtccatt agcgacacgt gcatgtgcct cttcgtcgac gggtggttcg ccatcaccgt    540

gacggcgctc cggtgcatga ctgacgcgtt gcacgtgtgg aacatgtgcc tccagctcaa    600

aatgatcaag agatcatcgt cgtcgtacag tcgcggcaat gacaagagga gtgggagtga    660

gagtgaaggc gaagggggtg acggcggaga aggaagcagc aaccgacccc gtgctgcgaa    720

tggccgccac ctggccttcc aatgcttgaa agccaaaaag ggactcttct ttgacctatt    780

ggtaattctc cctctgccac agattgtact atgggtggca attccatcat tattggaaaa    840

aggatcggta acgctagtaa tgacggtgtt cttgatcatc ttcctcttcc aatacctccc    900

caagatctac cactccgtct gccttttacg tcgaatgcag aacctttccg gctacatttt    960

cggcactgtt tggtggggga ttgctctcaa tttgattgct tatttcgtcg cctcacacgc   1020

ggcgggggcg tgttggtact tgttagggat tcaaagatcg gctaagtgct tgaaagagca   1080

atgtagaggg atagagaatt gtgacctgag attattggct tgcaaagacc caatttacta   1140

tggaacaaga agtatggtaa gggatagagc aaggttggtt tgggcagaaa ccaatcgagc   1200

aaggagtact tgcattgata accctgataa ctatgattat ggagcttata aatggaccgt   1260

tcagctagtt accaacgata gtcgtctcga gaaaatactt tttcctatct tttggggtct   1320

tatgactctc agcacatttg ggaacttgga gagcacaaca gaatggctgg aggttgtttt   1380

caacatcatt gttcttacca gtggacttct tcttgtcaca atgttgattg gtaacatcaa   1440

ggtgtttttg catgcaacaa cgtccaagaa acaagcaatg caattgaaga tgaggaacat   1500

agagtggtgg atgaggaaga ggcgcctgcc ttctggattc aagcaaaggg tccgcaatta   1560

tgagcggcaa cggtgggcgg ccatgcgcgg tgtcgatgaa tgccagatga tcagaaacct   1620

ccccgagggg ctccggagag atatcaagta ccatctttgc ctggatttag ttagacaggt   1680

accattgttt caacacatgg atgatttggt cctagagaac atttgtgatc gtgtcaaatc   1740

tctaattttt accaaaggag aaactataac aagggaaggc gacccagtac aaagaatgct   1800

atttgtagta aggggacatc tccaaagcag ccaagttctt agagatggtg tgaaaagttg   1860

ctgcatgtta gggcccggaa atttcagtgg cgatgagctc ttgtcatggt gtcttcgaag   1920

acccttcatt gagaggctcc caccatcgac ttccaccctc gtaacgcttg aaactaccga   1980

ggcatttggc ctcgatgctg aggatgtcaa atatgtcaca caacatttcc gttacacatt   2040

tgttaacgaa agggtcaaga ggagtgctcg gtattattct cccggatggc ggacttgggc   2100

tgcggtggcg attcaattgg cttggaggcg gtacaaacac cggttaaccc ttacgtcgtt   2160

gtcattcatt aggcctcgga ggccgttgtc gagaagtaat tcattggggg aggacagact   2220
```

-continued

```
caggctttat acagctatgt taacttcacc aaaaccaaat caagatgatt ttgatttttg   2280

aaaataaaaa aattaaaatg atgctacatg gaattcccat ggtccttaag tttgagtttt   2340

ctgaattaat gttcgctcta ataccatttg taagtacctc gtatttggta cgagagcatt   2400

attctttact tcgactcagc ctgtagtttt gtttttaaaa gaaaaaaaaa agtttgtatc   2460

tacagctaaa aaaaaaaaaa aaaaaactcg aaaagtcttt tagaccaggc gggggcccca   2520

cgatctcccc ccccggcggg ggtccaaaat aaatgtcccc ccctccccct ctactggagc   2580

tgcttccatt tcaccggccc gccgcttaca cacttcccgg tggggcaaa              2629
```

<210> SEQ ID NO 26
<211> LENGTH: 2130
<212> TYPE: DNA
<213> ORGANISM: Gossypium hirsutum

<400> SEQUENCE: 26

```
atggcaagtg aacatgaatt ttatccttca cgtgcaacgc ccatgcaata ctttacggat     60

gaagacgaag gagaagaaga aggaggagaa atagaagaag aatcgacgga cgacgaagtt    120

tgcaaagaag aagagaaaga gaattcaagt gactggagga gtttgtattt gatgtgcggc    180

ggtcgccgcg gcggtgggcg tcgccgtaaa acttggtcac tggggcaagt ttttttcgac    240

ccgagggcca aatgggttca agaatggaat agggttttcc tcctggtatg cgcgacggga    300

ctgttcgtgg acccattgtt cttttacgcc ctgtccatta gcgacacgtg catgtgcctc    360

ttcgtcgacg ggtggttcgc catcaccgtg acggcgctcc ggtgcatgac tgacgcgttg    420

cacgtgtgga acatgtgcct ccagctcaaa atgatcaaga gatcatcgtc gtcgtacagt    480

cgcggcaatg acaagaggag tgggagtgag agtgaaggcg aagggggtga cggcggagaa    540

ggaagcagca accgaccccg tgctgcgaat ggccgccacc tggccttcca atgcttgaaa    600

gccaaaaagg gactcttctt tgacctattg gtaattctcc ctctgccaca gattgtacta    660

tgggtggcaa ttccatcatt attggaaaaa ggatcggtaa cgctagtaat gacggtgttc    720

ttgatcatct tcctcttcca atacctcccc aagatctacc actccgtctg ccttttacgt    780

cgaatgcaga acctttccgg ctacattttc ggcactgttt ggtgggggat tgctctcaat    840

ttgattgctt atttcgtcgc ctcacacgcg gcgggggcgt gttggtactt gttagggatt    900

caaagatcgg ctaagtgctt gaaagagcaa tgtagaggga tagagaattg tgacctgaga    960

ttattggctt gcaaagaccc aatttactat ggaacaagaa gtatggtaag ggatagagca   1020

aggttggttt gggcagaaac caatcgagca aggagtactt gcattgataa ccctgataac   1080

tatgattatg gagcttataa atggaccgtt cagctagtta ccaacgatag tcgtctcgag   1140

aaaatacttt ttcctatctt ttggggtctt atgactctca gcacatttgg gaacttggag   1200

agcacaacag aatggctgga ggttgttttc aacatcattg ttcttaccag tggacttctt   1260

cttgtcacaa tgttgattgg taacatcaag gtgtttttgc atgcaacaac gtccaagaaa   1320

caagcaatgc aattgaagat gaggaacata gagtggtgga tgaggaagag gcgcctgcct   1380

tctggattca agcaaagggt ccgcaattat gagcggcaac ggtgggcggc catgcgcggt   1440

gtcgatgaat gccagatgat cagaaacctc cccgaggggc tccggagaga tatcaagtac   1500

catctttgcc tggatttagt tagacaggta ccattgtttc aacacatgga tgatttggtc   1560

ctagagaaca tttgtgatcg tgtcaaatct ctaattttta ccaaaggaga aactataaca   1620

agggaaggcg acccagtaca aagaatgcta tttgtagtaa ggggacatct ccaaagcagc   1680

caagttctta gagatggtgt gaaaagttgc tgcatgttag ggcccggaaa tttcagtggc   1740
```

```
gatgagctct tgtcatggtg tcttcgaaga cccttcattg agaggctccc accatcgact   1800
tccaccctcg taacgcttga aactaccgag gcatttggcc tcgatgctga ggatgtcaaa   1860
tatgtcacac aacatttccg ttacacattt gttaacgaaa gggtcaagag gagtgctcgg   1920
tattattctc ccggatggcg gacttgggct gcggtggcga ttcaattggc ttggaggcgg   1980
tacaaacacc ggttaaccct tacgtcgttg tcattcatta ggcctcggag gccgttgtcg   2040
agaagtaatt cattggggga ggacagactc aggctttata cagctatgtt aacttcacca   2100
aaaccaaatc aagatgattt tgatttttga                                    2130
```

<210> SEQ ID NO 27
<211> LENGTH: 1986
<212> TYPE: DNA
<213> ORGANISM: Cucumis melo

<400> SEQUENCE: 27

```
atggccacca cctcccaaac atccgatgac gaagaactag aacacgacga atcagaagat     60
gaagaagaac actccaacgc tgcgttttgt cagagcttat acggagttgg ttctgttctc    120
gacccaacaa ccaaatgggt tcgagaatgg aattgggtct tcctcctcgt ctgtgcagcg    180
gggctgttcg tcgacccttt gtttctctac acgctttcca taagcgagtc gtggatgtgc    240
gtttttattg acgggtggtt ggccatcacc gtcacggtcc tccgctgcat gggcgatgct    300
ttgcaccttt ggaatatctg ggttcagctg aagactgcta caaagtcatc ctttgcagct    360
ggtaggggcg agggtgatgc gagggatgaa aatagagggc ttagagatag tagcccacgc    420
gccgtcgctc tccggtattt gaagtccaag aaaggcttct tttttgacct ctttgttatt    480
cttccttttc ctcaggttgt attatgggta gtaattccca gaataatgaa agaaggatta    540
gtgacaatgg tgatgacagt attattaata gtatttttgt ttcaatattt accaaaattg    600
tatcattctg tttgcttatt acgacgtctc caaaaccttt ctggctacat ctttggcact    660
gtttggtggg gcattgctct caatctcatt gcttactttg ttgctgccca tgctgcaggt    720
gcatgttggt atctattagg ggtacagaga gcagcaaaat gtcttaaaga gcaatgtaga    780
tcagcaacaa gcaacagctg tgggctgaga ttgttatcat gcaaagaccc aatcttctat    840
ggaccaaaca atatgagaat gggaagagat agaggaagat ttgattgggc aaacaatagg    900
caatcgaagt tcatgtgttt agatactgct gataactttg attatggagc ttataaatgg    960
actgttcaac ttgttgtcaa tcaaagtcga ttggagaaaa tcctttttccc catcttttgg   1020
ggcctcatga ctcttagtac ctttgggaat ttggaaagca caactgaatg gctggaagtt   1080
gtgttcaata tcattgttct caccagtgga ctcttattgg tcaccatgtt gattggaaat   1140
atcaaggtgt ttctacatgc aacaacgtca aaaaaacaag gaatgcagct gaagatgagg   1200
aacctagagt ggtggatgag gaagcgacgg ctgccacaag ggtttcgtca gcgtgttcgg   1260
aactacgaac ggcaacggtg ggcggcgatg cggggcgtgg acgagtgcga gatgataaaa   1320
aacctaccgg aggggcttcg acgagacata aagtatcacc tttgcttgga tctagttagg   1380
caggtgccat tgtttcaaca tatggatgat cttgttcttg agaacatttg tgatcgtgtc   1440
aagtccctca tcttcactaa gggcgaaaca ataacaagag aaggagatcc agtacaaaga   1500
atgctattcg tagtgcgagg gcatctccaa agcagccaag tcttacgcga cggcgtaaaa   1560
agctgctgca tgttgggccc cggcaacttc agcggcgacg agcttctatc ctggtgcctc   1620
cgccgccctt tcatagagcg ccttccaccg tcctccttta ctcttgtgac actcgagacc   1680
```

-continued actgaagcct tcagcttgga ggccgaggat gtcaagtatg taacccagca ctttcgctac 1740
acctttgtca atgacaaggt caagcgcagt gcccgctact actccccagg ctggcgcact 1800
tgggctgctg ttgccatcca gctagcctgg cgccgatatc gccatcgtct cacactcacg 1860
tccttgtcgt ttattcggcc ccggcgccca ctctcacggt gctcttcctt gggggaggat 1920
cgcctccgcc tctatacggc gttgcttact tctcctaagc ccaaccacga ccactttgat 1980
ttttga 1986

<210> SEQ ID NO 28
<211> LENGTH: 1986
<212> TYPE: DNA
<213> ORGANISM: Cucumis melo

<400> SEQUENCE: 28
atggccacca cctcccaaac atccgatgac gaagaactag aacacgacga atcagaagat 60
gaagaagaac actccaacgc tgcgttttgt cagagcttat acggagttgg ttctgttctc 120
gacccaacaa ccaaatgggt tcgagaatgg aattgggtct tcctcctcgt ctgtgcagcg 180
gggctgttcg tcgacccttt gtttctctac acgctttcca taagcgagtc gtggatgtgc 240
gtttttattg acgggtggtt ggccatcacc gtcacggtcc tccgctgcat gggcgatgct 300
ttgcaccttt ggaatatctg ggttcagctg aagactgcta caaagtcatc ctttgcagct 360
ggtaggggcg agggtgatgc gagggatgaa aatagagggc ttagagatag tagcccacgc 420
gccgtcgctc tccggtattt gaagtccaag aaaggcttct tttttgacct ctttgttatt 480
cttccttttc ctcaggttgt attatgggta gtaattccca gaataatgaa agaaggatta 540
gtgacaatgg tgatgacagt attattaata gtatttttgt ttcaatattt accaaaattg 600
tatcattctg tttgcttatt acgacgtctc caaaaccttt ctggctacat ctttggcact 660
gtttggtggg gcattgctct caatctcatt gcttactttg ttgctgccca tgctgcaggt 720
gcatgttggt atctattagg ggtacagaga gcagcaaaat gtcttaaaga gcaatgtaga 780
tcagcaacaa gcaacagctg tgggctgaga ttgttatcat gcaaagaccc aatcttctat 840
ggaccaaaca atatgagaat gggaagagat agaggaagat ttgattgggc aaacaatagg 900
caatcgaagt tcatgtgttt agatactgct gataactttg attatggagc ttataaatgg 960
actgttcaac ttgttgtcaa tcaaagtcga ttggagaaaa tccttttccc catcttttgg 1020
ggcctcatga ctcttagtac ctttgggaat ttggaaagca caactgaatg gctggaagtt 1080
gtgttcaata tcattgttct caccagtgga ctcttattgg tcaccatgtt gattggaaat 1140
atcaaggtgt ttctacatgc aacaacgtca aaaaaacaag gaatgcagct gaagatgagg 1200
aacctagagt ggtggatgag gaagcgacgg ctgccacaag ggtttcgtca gcgtgttcgg 1260
aactacgaac ggcaacggtg ggcggcgatg cggggcgtgg acgagtgcga gatgataaaa 1320
aacctaccgg aggggcttcg acgagacata aagtatcacc tttgcttgga tctagttagg 1380
caggtgccat tgtttcaaca tatggatgat cttgttcttg agaacatttg tgatcgtgtc 1440
aagtccctca tcttcactaa gggcgaaaca ataacaagag aaggagatcc agtacaaaga 1500
atgctattcg tagtgcgagg gcatctccaa agcagccaag tcttacgcga cggcgtaaaa 1560
agctgctgca tgttgggccc cggcaacttc agcggcgacg agcttctatc ctggtgcctc 1620
cgccgccctt tcatagagcg ccttccaccg tcctccttta ctcttgtgac actcgagacc 1680
actgaagcct tcagcttgga ggccgaggat gtcaagtatg taacccagca ctttcgctac 1740
acctttgtca atgacaaggt caagcgcagt gcccgctact actccccagg ctggcgcact 1800
tgggctgctg ttgccatcca gctagcctgg cgccgatatc gccatcgtct cacactcacg 1860
tccttgtcgt ttattcggcc ccggcgccca ctctcacggt gctcttcctt gggggaggat 1920
cgcctccgcc tctatacggc gttgcttact tctcctaagc ccaaccacga ccactttgat 1980
ttttga 1986

<210> SEQ ID NO 29
<211> LENGTH: 3192
<212> TYPE: DNA
<213> ORGANISM: Zea mays

<400> SEQUENCE: 29
gtacatgtac tacgcgggca aagcaaagca tcggtgtcta cctcattatt ttcggagtcc 60
gagtggcgaa acccgccgca gcttccactg ggcagtgctc cacaggctca tatccgattc 120
cgatccctaa gacctcagcc gctgcggcat ccacggccaa ctcaagcgct ggcaactggc 180
aagggcagat gatctgtgta tagcactcgc taccttctct tgatttcccc ctcaggtcgc 240
tgaccaaggg tcctgtccgc catggatgcg gagcgaagct ctgcacgcag cgccacacct 300
tttggtccgc cgtccgatcg ccaccgctag acgccacgcc tgcgttgcct tcccggctga 360
atcgccgatt cccttggcgg tctagtgcct gcggtcggcg ccagacgccg gcgaggtagc 420
cgcgagacac aggtacgggt gccgaacggg aacggctgct gcccgccgag ccgtcgactg 480
cctgcctgga gccttgactg cgcaagcgca gctgccgtgt gttgagtgct gagtcgccga 540
ctccaccagg tggccagcga ttgctttgct gctccaggaa agaagccaaa aaaaaacacg 600
aagaattaaa catcgattga aagggaaaag acaatgccaa gcctgaactg agaggcgcac 660
actggatttc gcatcagttc atgtcgttcc ttacaccgtc aatttgacga atcacctcgc 720
cacgccgcct tgattttgtt ttgtcctccg cttctggccg ggctcagttc agctgtatgg 780
tattggtatc gccatgtcaa gcgacctctc cacacgctcc tcgccttcct cctccaccgc 840
gtcgccttcc gacgactcgc ggcggcagga gcaaggccag gcggcgggta acgccagcgg 900
gagccggcgg tggcggtggc gcctcgggct gggcgcggcg tgggcgctgg acccgcgggc 960
gaggtgggtc cgggactgga accgcgccta cctcctggcc tgcgcggccg ggctcatggt 1020
cgacccgctc ttcctctacg ccgtgtccct gagcggcccg ctcatgtgca tattcgtcga 1080
cggctggctc gccgccgccg tcaccgcgct gcgctgcggg gtggacgcca tgcacgtgtg 1140
gaacgtcgcc acgcagctcc gcaccgccaa ggcgccgccg ggtaagcgcg tggccggcga 1200
cgaggagcag cagcagaccg tcgccgaggc cgcgcgcaag ctccccgagg acgcggcgtc 1260
caggaggggg ctgttgctgg acttcttcgt catccttccc gtgatgcagg tggtggtgtg 1320
ggttgcggcg ccggcgatga tccgcgcggg gctgacgacg ccggtgatga cggtgctgct 1380
ggtgtcgttc ctgctggagt acctgcccaa gatctaccac gcggcgcgcc tgctccggcg 1440
gatgcagagg cagtctggct acatcttcgg caccatctgg tggggcatcg cgctcaacct 1500
catggcctac ttcgtcgccg cccatgctgt gggcgcgtgc tggtacctgc tcggcgtcca 1560
gcgggccagc aagtgcctga aagagcagtg cctccaggcg gccgggtgcg cgcgcggcag 1620
cgcggtggcc tgcgcggcgc cgctgtacta cggcggctcc ccgtctcccg gagtcggcgg 1680
cggcgacagg ctcgcctggg ccgggaacgc gcaggcccgg ggcacgtgcc tcgccagcgg 1740
cgacaactac cagtacggcg cgtacacgtg gacggtgatg ctggtggcga acccgagccg 1800
ggtggagcgg atgctgctcc ccatcttctg ggcctcatg acgctcagca cgttcggcaa 1860

-continued cctggagagc acgacggagt ggctggagat cgtgttcaac atcatcacca tcacgggcgg 1920
gctcgtcctc gtcaccatgc tcatcggcaa catcaaggtg ttcctgaacg cgaccacgtc 1980
caagaagcag gccatgcaca cgcggctgcg cggcgtggag tggtggatga agcgcaagaa 2040
actgccgcgg agcttccgcg gccgggtgcg ccagttcgag cgccagcggt gggccgccac 2100
gcgcggcgtc gacgagtgcc agatcgtgcg cgacctcccc gagggcctcc gccgggacat 2160
caagtaccac ctctgcctcg acctcgtccg ccaggtccca ttcttccagc acatggacga 2220
cctcgtgctc gagaacatct gcgacagggt gaaatccctc atctttccca agggagaaac 2280
catcgtgagg gagggcgacg tggtgcagcg gatgctgttc atcgtgcggg gccacctgca 2340
gtgcagccag gtgctgcgga acggcgcgac gagcagctgc acgctggggc ctggcaactt 2400
cagcggcgac gagctgctgt cgtggtgcct gcgccgcccg ttcctggaac gcctcccgac 2460
gtcgtcggcg acgctggtga cgctggagag caccgaggtg ttcggcctgg acgccgccga 2520
cgtcaagtac gtcacgcagc acttccgcta caccttcacc aacgacaagg tgcgccgcag 2580
cgctcgctac tactcgcccg gctggcgtac ctgggcggcc gtcgccgttc agctggcctg 2640
gaggaggtac aagcaccgca agacgctctc gtcgctctcc ttcatccgcc cgcggcgccc 2700
gctgtcccgc tgctcctcgc tcggggagga gaagctccgc ctgtacacgg ccatcctcac 2760
ctcgcccaag cccaaccagg acgacgactt ctagctagct tagctaggcc gttccaggcc 2820
ggattctctt ctcctcagcg aggagtatat atatcaaaca acatgcattt atttgtagta 2880
ttcattactc gcatgtcgca tgagagacag agccatgacc gtactccctc cgctttccta 2940
ttagttgtcg tttaggataa cgacacggtc tctaatatat aactttgacc aatatttttt 3000
gttaaaatac aaataaactc ttaatacatt tatactttta taaaagtact ttttatgata 3060
aattggtgca tataaatatt aggtttcaaa actaaataac aaaatagtta tttgtagtca 3120
aaactttata agtttgactc gaaccttatc taaaacgaca attaatagga aaccggaggg 3180
agtattttgc at 3192

<210> SEQ ID NO 30
<211> LENGTH: 2001
<212> TYPE: DNA
<213> ORGANISM: Zea mays

<400> SEQUENCE: 30
atgtcaagcg acctctccac acgctcctcg ccttcctcct ccaccgcgtc gccttccgac 60
gactcgcggc ggcaggagca aggccaggcg gcgggtaacg ccagcgggag ccggcggtgg 120
cggtggcgcc tcgggctggg cgcggcgtgg gcgctggacc cgcgggcgag gtgggtccgg 180
gactggaacc gcgcctacct cctggcctgc gcggccgggc tcatggtcga cccgctcttc 240
ctctacgccg tgtccctgag cggcccgctc atgtgcatat tcgtcgacgg ctggctcgcc 300
gccgccgtca ccgcgctgcg ctgcggggtg gacgccatgc acgtgtggaa cgtcgccacg 360
cagctccgca ccgccaaggc gccgccgggt aagcgcgtgg ccggcgacga ggagcagcag 420
cagaccgtcg ccgaggccgc gcgcaagctc cccgaggacg cggcgtccag gagggggctg 480
ttgctggact tcttcgtcat ccttcccgtg atgcaggtgg tggtgtgggt tgcggcgccg 540
gcgatgatcc gcgcggggct gacgacgccg gtgatgacgg tgctgctggt gtcgttcctg 600
ctggagtacc tgcccaagat ctaccacgcg gcgcgcctgc tccggcggat gcagaggcag 660
tctggctaca tcttcggcac catctggtgg ggcatcgcgc tcaacctcat ggcctacttc 720
gtcgccgccc atgctgtggg cgcgtgctgg tacctgctcg gcgtccagcg ggccagcaag 780

```
tgcctgaaag agcagtgcct ccaggcggcc gggtgcgcgc gcggcagcgc ggtggcctgc     840

gcggcgccgc tgtactacgg cggctccccg tctcccggag tcggcggcgg cgacaggctc     900

gcctgggccg ggaacgcgca ggcccggggc acgtgcctcg ccagcggcga caactaccag     960

tacggcgcgt acacgtggac ggtgatgctg gtggcgaacc cgagccgggt ggagcggatg    1020

ctgctcccca tcttctgggg cctcatgacg ctcagcacgt tcggcaacct ggagagcacg    1080

acggagtggc tggagatcgt gttcaacatc atcaccatca cgggcgggct cgtcctcgtc    1140

accatgctca tcggcaacat caaggtgttc ctgaacgcga ccacgtccaa gaagcaggcc    1200

atgcacacgc ggctgcgcgg cgtggagtgg tggatgaagc gcaagaaact gccgcggagc    1260

ttccgcggcc gggtgcgcca gttcgagcgc cagcggtggg ccgccacgcg cggcgtcgac    1320

gagtgccaga tcgtgcgcga cctccccgag ggcctccgcc gggacatcaa gtaccacctc    1380

tgcctcgacc tcgtccgcca ggtcccattc ttccagcaca tggacgacct cgtgctcgag    1440

aacatctgcg acagggtgaa atccctcatc tttcccaagg gagaaaccat cgtgagggag    1500

ggcgacgtgg tgcagcggat gctgttcatc gtgcggggcc acctgcagtg cagccaggtg    1560

ctgcggaacg gcgcgacgag cagctgcacg ctggggcctg gcaacttcag cggcgacgag    1620

ctgctgtcgt ggtgcctgcg ccgcccgttc ctggaacgcc tcccgacgtc gtcggcgacg    1680

ctggtgacgc tggagagcac cgaggtgttc ggcctggacg ccgccgacgt caagtacgtc    1740

acgcagcact tccgctacac cttcaccaac gacaaggtgc gccgcagcgc tcgctactac    1800

tcgcccggct ggcgtacctg ggcggccgtc gccgttcagc tggcctggag gaggtacaag    1860

caccgcaaga cgctctcgtc gctctccttc atccgcccgc ggcgcccgct gtcccgctgc    1920

tcctcgctcg ggaggagaa gctccgcctg tacacggcca tcctcacctc gcccaagccc    1980

aaccaggacg acgacttcta g                                              2001
```

<210> SEQ ID NO 31
<211> LENGTH: 2076
<212> TYPE: DNA
<213> ORGANISM: Glycine max

<400> SEQUENCE: 31

```
atggctacta ccataacaga gcaagaagcc tcatcacgtg ccccgcacgt gctcgactac      60

gccaccacta catccgacga cgacacggaa aaggaggagg aggagctggt acacgagcaa     120

aacgaatcct ccggcggagg gcggtggttt ccggcggcgt gcggtggcgg cacgcggcgg     180

agcgggggag gcgcgttagg gcgagttctt gacccaaggg cgaagtgggt ccaggaatgg     240

aacagggtgt tcctgctagt gtgcgccgcg gggttgttcg ttgaccctct cttcttctac     300

gcgctctccg tcagcgactc gtgcatgtgc gtcttcgttg acgggtggct cgccgtcacc     360

gtcacggtgc tgcggtgcat gaccgacgca ctgcacgtgt ggaacatggt tataaggtgc     420

aagatggcga aacgcacctt cggactcggc gcctccacca cttcttccgg cagaggaaca     480

tcctcgtcct ctgtcggact cagagatacc cgaccgcgtt ccgtcgcgat gggatatctc     540

atgtcacgga ccggattctt ttttgatctg ttcgttattc ttcctctacc acagattgta     600

ctatgggtgg caatcccctc cttgttggag aaaggttcag tgacattggt gatgacagtg     660

ttcttaatta tctttctctt ccaatacctt cccaaaattt ttcattcggt ttgccatttg     720

cgacgcacgc aaaacctctc tggctacatt tttggaacag tttggtgggg aatcgccctt     780

aacatgatcg cgtattttgt tgcttcccat gcagcagggg catgttggta cttgctaggg     840
```

-continued

```
atacaaaggg cagccaagtg tctcaaagtg cagtgtgaga aaacaagtgg ttgtggcatg    900

aaaatcttgt cttgtcaaac acccatatat tacggaagca acagttttct agttagggat    960

agggcaaggt tggcttgggc agagaacagg gaagtgagac acacatgcct aaatggtcct   1020

gacaactaca actatggagc ttatagatgg tctgttcagc ttgtcacaaa cgataatcga   1080

ttggagaaga tacttttccc tatcttctgg ggcctaatga ctctcagcac ttttggaaac   1140

ctagagagta caaccgaatg gctggaagta gttttcaaca tcattgtgct gaccagtggc   1200

cttcttcttg tcactatgtt gattggaaac atcaaggtat ttttgcatgc aacaacgtca   1260

aaaaagcaag caatgcaatt gaagatgagg aatattgaat ggtggatgag gaaacgacgc   1320

ttgccgctag ggtttaggca gcgcgtgcgt aactatgaga ggcaacgttg ggctgccatg   1380

cgtggggttg atgaatttga gatgactaaa aatcttcctg agggattaag aagagacatt   1440

aaataccatc tttgtctaga cttggtgaga caggtgcctc tatttcaaca catggacgat   1500

ctggttctag agaacatctg tgaccgtgtg aagtctctga tattcacaaa gggagaaaca   1560

atagctagag aaggagaccc agttcagaga atgctatttg tagtaagggg tcaccttcaa   1620

agcagccaag tcctaaggga tggtgtgaag agttgttgca tgttaggtcc aggaaacttc   1680

agtggggacg aactcctctc atggtgttta aggagaccct tcatagaacg ccttccacca   1740

tcttcatcca cactcatcac gttggaaacc accgaggctt ttggccttga agccgaggat   1800

gtgaagtatg tgacacaaca ttttaggtac acatttgtta aggagaaggt gaagagaagt   1860

gcaaggtatt actcaccagg gtggagaact tgggctgctg tggccattca attggcatgg   1920

aggaggtaca agcataggtt gactttgact tcattgtcct ttataaggcc taggaggcct   1980

ttgtcaaggt cctcttccat gggagaggac aggcttcgcc tctacacggc tttgttaacc   2040

tccccaaagc ctaatcagga tgattttgac ttttga                             2076
```

<210> SEQ ID NO 32
<211> LENGTH: 2001
<212> TYPE: DNA
<213> ORGANISM: Oryza sativa

<400> SEQUENCE: 32

```
atggcgtcct cctccgccgc cgccgcctcg tccgctcatg gtgttggtgt tgtgcagagg     60

ttatggctgg aggagcagga gcggaagccg ccgccgaagc gtggcggcgg caagcggagg    120

tgggcgtggg cgccgctcga gccgcggcgg gcggggtggt gggcgcggga gtgggacagg    180

gcgtacctcc tcgcctgcgc ggcggggctc atggtcgacc cgctcttcct gtacgccgtg    240

tccgtcagcg ggccgctcat gtgcgtcttc ctcgacgggt ggttcgccgc cgcggtcacc    300

gtgctccggt gcacggtgga cgccatgcac gcctggaact tgctgatgcg cctccgggcg    360

gcggtgcggc cgccggagga ggacgacggc gccgacgagg aggtggcggc ggagcgggga    420

gccggcggca atggcggcgg gccggcgccg gctcaggtgg cgaggccggt gtccaggaaa    480

gggctcatgc tggacatgtt cgtcattctt cccgtaatgc aggtgatcgt ctgggtggcg    540

gcaccggcga tgatacgcgc cgggtcgacg acggcggtaa tgacggtgct cctggtgtcg    600

ttcctgttcg agtacctgcc caagatatac cacgccgtcc gcctcctgcg ccggatgcag    660

aacacctacg tgttcggcac catctggtgg ggcatcgcgc tcaacctcat ggcctacttc    720

gtcgccgctc acgcggtggg cgcgtgctgg tacctgctcg ggcgcagcg cgcgaccaag     780

tgcctcaagg agcagtgcgc ccagggcggg agcgggtgcg cgcccggtgc gctggcgtgc    840

gcggcgccgc tctactacgg tggcgccgtg ggcggcgtgg gcgcggacag gctcgcctgg    900
```

gccctcgacg cctccgcccg gggcacgtgc ctcgacagcg gcgacaacta ccagtacggg 960
gcgtacaagt ggaccgtcat gctcgtggcg aacccgagcc ggctggagaa gatcttgctc 1020
cccatcttct ggggcctcat gacactcagt acatttggga acttggcgag cacaacagag 1080
tggctggaga tagtgttcaa catcatcact atcaccgggg gcttaatcct cgtgacgatg 1140
ctcataggaa acatcaaggt gttcttgaac gcggcgacgt cgaagaagca ggcgatgcag 1200
acgaggctgc ggggcgtgga gtggtggatg aagcggaaga agctgccgca gagcttccgg 1260
caccgggtgc ggcagcacga gcggcagcgg tgggcggcca cgcgcggcgt cgacgagtgc 1320
cgcatcgtcc gcgacctgcc ggaggggctc cgccgcgaca tcaagtacca cctctgcctc 1380
gacctcgtcc gccaggtgcc actgttccaa cacatggacg acctggtgct cgagaacatc 1440
tgtgacaggg tcaagtccct cgtattcccc aaaggagaaa ttatcgttag agagggcgac 1500
ccggtgcaga ggatgctgtt catagtgcga gggcacctgc agagcagcca ggtgctgagg 1560
accggcgcca cgagctgctg cacgctgggg ccgggcaact tcagcgggga cgagctgctg 1620
tcgtggtgca tgcggcggcc gttcctggag cggctgccgg cgtcgtcgtc gacgctggtg 1680
acgatggaga gcacggaggc gttcgggctg gaggccgcgg acgtcaagta cgtgacgcag 1740
cacttccgct acaccttcac caacgacagg gtgcggcgca gcgcgcgcta ctactcgcac 1800
gggtggcgca cgtgggcggc cgtcgccgtg cagctcgcgt ggcggcggta caagcaccgc 1860
aagacgctcg cgtcgctctc cttcatccgc ccgcgcaggc cgctgtcgcg gtgctcgtcg 1920
ctcggcgagg agaagctccg gctctacacc gcgatcctca cctcacccaa gcccaacccc 1980
aaccaggacg acttggtgtg a 2001

<210> SEQ ID NO 33
<211> LENGTH: 2001
<212> TYPE: DNA
<213> ORGANISM: Oryza sativa

<400> SEQUENCE: 33
atggcgtcct cctccgccgc cgccgcctcg tccgctcatg gtgttggtgt tgtgcagagg 60
ttatggctgg aggagcagga gcggaagccg ccgccgaagc gtggcggcgg caagcggagg 120
tgggcgtggg cgccgctcga gccgcggcgg gcggggtggt gggcgcggga gtgggacagg 180
gcgtacctcc tcgcctgcgc ggcggggctc atggtcgacc cgctcttcct gtacgccgtg 240
tccgtcagcg ggccgctcat gtgcgtcttc ctcgacgggt ggttcgccgc cgcggtcacc 300
gtgctccggt gcacggtgga cgccatgcac gcctggaact tgctgatgcg cctccgggcg 360
gcggtgcggc cgccggagga ggacgacggc gccgacgagg aggtggcggc ggagcgggga 420
gccggcggca atggcggcgg gccggcgccg gctcaggtgg cgaggccggt gtccaggaaa 480
gggctcatgc tggacatgtt cgtcattctt cccgtaatgc aggtgatcgt ctgggtggcg 540
gcaccggcga tgatacgcgc cgggtcgacg acggcggtaa tgacggtgct cctggtgtcg 600
ttcctgttcg agtacctgcc caagatatac cacgccgtcc gcctcctgcg ccggatgcag 660
aacacctacg tgttcggcac catctggtgg ggcatcgcgc tcaacctcat ggcctacttc 720
gtcgccgctc acgcggtggg cgcgtgctgg tacctgctcg gggcgcagcg cgcgaccaag 780
tgcctcaagg agcagtgcgc ccagggcggg agcgggtgcg cgcccggtgc gctggcgtgc 840
gcggcgccgc tctactacgg tggcgccgtg ggcggcgtgg gcgcggacag gctcgcctgg 900
gccctcgacg cctccgcccg gggcacgtgc ctcgacagcg gcgacaacta ccagtacggg 960

-continued gcgtacaagt ggaccgtcat gctcgtggcg aacccgagcc ggctggagaa gatcttgctc 1020
cccatcttct ggggcctcat gacactcagt acatttggga acttggcgag cacaacagag 1080
tggctggaga tagtgttcaa catcatcact atcaccgggg gcttaatcct cgtgacgatg 1140
ctcataggaa acatcaaggt gttcttgaac gcggcgacgt cgaagaagca ggcgatgcag 1200
acgaggctgc ggggcgtgga gtggtggatg aagcggaaga agctgccgca gagcttccgg 1260
caccgggtgc ggcagcacga gcggcagcgg tgggcggcca cgcgcggcgt cgacgagtgc 1320
cgcatcgtcc gcgacctgcc ggaggggctc cgccgcgaca tcaagtacca cctctgcctc 1380
gacctcgtcc gccaggtgcc actgttccaa cacatggacg acctggtgct cgagaacatc 1440
tgtgacaggg tcaagtccct cgtattcccc aaaggagaaa ttatcgttag agagggcgac 1500
ccggtgcaga ggatgctgtt catagtgcga gggcacctgc agagcagcca ggtgctgagg 1560
accggcgcca cgagctgctg cacgctgggg ccgggcaact tcagcgggga cgagctgctg 1620
tcgtggtgca tgcggcggcc gttcctggag cggctgccgg cgtcgtcgtc gacgctggtg 1680
acgatggaga gcacggaggc gttcgggctg gaggccgcgg acgtcaagta cgtgacgcag 1740
cacttccgct acaccttcac caacgacagg gtgcggcgca gcgcgcgcta ctactcgcac 1800
gggtggcgca cgtgggcggc cgtcgccgtg cagctcgcgt ggcggcggta caagcaccgc 1860
aagacgctcg cgtcgctctc cttcatccgc ccgcgcaggc cgctgtcgcg gtgctcgtcg 1920
ctcggcgagg agaagctccg gctctacacc gcgatcctca cctcacccaa gcccaacccc 1980
aaccaggacg acttggtgtg a 2001

<210> SEQ ID NO 34
<211> LENGTH: 25
<212> TYPE: DNA
<213> ORGANISM: Glycine max

<400> SEQUENCE: 34
ggagagagga gaaggtgttg tgcat 25

<210> SEQ ID NO 35
<211> LENGTH: 25
<212> TYPE: DNA
<213> ORGANISM: Glycine max

<400> SEQUENCE: 35
ccagccctcc gtccatgtac aagca 25

<210> SEQ ID NO 36
<211> LENGTH: 25
<212> TYPE: DNA
<213> ORGANISM: Glycine max

<400> SEQUENCE: 36
atgtagcctg tgactttttg cattc 25

<210> SEQ ID NO 37
<211> LENGTH: 25
<212> TYPE: DNA
<213> ORGANISM: Glycine max

<400> SEQUENCE: 37
agcgactccc gcgatacgta cgcca 25

<210> SEQ ID NO 38
<211> LENGTH: 25

<212> TYPE: DNA
<213> ORGANISM: Glycine max

<400> SEQUENCE: 38
caccctgtca cagatgttgt caaga 25

<210> SEQ ID NO 39
<211> LENGTH: 25
<212> TYPE: DNA
<213> ORGANISM: Glycine max

<400> SEQUENCE: 39
aaggcaccat gaaagcagct cgtca 25

<210> SEQ ID NO 40
<211> LENGTH: 25
<212> TYPE: DNA
<213> ORGANISM: Glycine max

<400> SEQUENCE: 40
attcaaggtg gtcatgtggc cttat 25

<210> SEQ ID NO 41
<211> LENGTH: 25
<212> TYPE: DNA
<213> ORGANISM: Glycine max

<400> SEQUENCE: 41
gagtagaaga acagcgggtc tatcg 25

<210> SEQ ID NO 42
<211> LENGTH: 25
<212> TYPE: DNA
<213> ORGANISM: Glycine max

<400> SEQUENCE: 42
atcacgaatg cgtcgaacca gaatc 25

<210> SEQ ID NO 43
<211> LENGTH: 25
<212> TYPE: DNA
<213> ORGANISM: Glycine max

<400> SEQUENCE: 43
tgacaggaag tgcccattgg tagat 25

<210> SEQ ID NO 44
<211> LENGTH: 25
<212> TYPE: DNA
<213> ORGANISM: Glycine max

<400> SEQUENCE: 44
gcagcatatt gcaagagcct gcgtt 25

<210> SEQ ID NO 45
<211> LENGTH: 25
<212> TYPE: DNA
<213> ORGANISM: Glycine max

<400> SEQUENCE: 45
tgctgcccat ctctgacgtt caaaa 25

<210> SEQ ID NO 46

<211> LENGTH: 25
<212> TYPE: DNA
<213> ORGANISM: Glycine max

<400> SEQUENCE: 46
ctaaatggat tgtcatccac aactg 25

<210> SEQ ID NO 47
<211> LENGTH: 25
<212> TYPE: DNA
<213> ORGANISM: Glycine max

<400> SEQUENCE: 47
ttattgtcat aatgatttta atttt 25

<210> SEQ ID NO 48
<211> LENGTH: 25
<212> TYPE: DNA
<213> ORGANISM: Glycine max

<400> SEQUENCE: 48
aaggcaccat gaaagcagct cgtca 25

<210> SEQ ID NO 49
<211> LENGTH: 25
<212> TYPE: DNA
<213> ORGANISM: Glycine max

<400> SEQUENCE: 49
caaaccccaa aaaatgggat aaaga 25

<210> SEQ ID NO 50
<211> LENGTH: 25
<212> TYPE: DNA
<213> ORGANISM: Glycine max

<400> SEQUENCE: 50
aaaatagaag gtatctaatt tttaa 25

<210> SEQ ID NO 51
<211> LENGTH: 25
<212> TYPE: DNA
<213> ORGANISM: Glycine max

<400> SEQUENCE: 51
taaaaaaata gaaataacta catgt 25

<210> SEQ ID NO 52
<211> LENGTH: 25
<212> TYPE: DNA
<213> ORGANISM: Glycine max

<400> SEQUENCE: 52
ctatcttggt ttcttgctaa ctctg 25

<210> SEQ ID NO 53
<211> LENGTH: 25
<212> TYPE: DNA
<213> ORGANISM: Glycine max

<400> SEQUENCE: 53
taattttatc aactattata ccatc 25

<210> SEQ ID NO 54
<211> LENGTH: 25
<212> TYPE: DNA
<213> ORGANISM: Glycine max

<400> SEQUENCE: 54
gaatttttag accattcaac cggga 25

<210> SEQ ID NO 55
<211> LENGTH: 25
<212> TYPE: DNA
<213> ORGANISM: Glycine max

<400> SEQUENCE: 55
acattcttgt aaaatatttt ctctg 25

<210> SEQ ID NO 56
<211> LENGTH: 25
<212> TYPE: DNA
<213> ORGANISM: Glycine max

<400> SEQUENCE: 56
aaggatattt acaaatttga gacat 25

<210> SEQ ID NO 57
<211> LENGTH: 25
<212> TYPE: DNA
<213> ORGANISM: Glycine max

<400> SEQUENCE: 57
tttcatattt tcttcatccc agcat 25

<210> SEQ ID NO 58
<211> LENGTH: 25
<212> TYPE: DNA
<213> ORGANISM: Glycine max

<400> SEQUENCE: 58
atgatggtag catgagatta caccc 25

<210> SEQ ID NO 59
<211> LENGTH: 25
<212> TYPE: DNA
<213> ORGANISM: Glycine max

<400> SEQUENCE: 59
atggctcatt ttagaataaa cttta 25

<210> SEQ ID NO 60
<211> LENGTH: 25
<212> TYPE: DNA
<213> ORGANISM: Artificial
<220> FEATURE:
<223> OTHER INFORMATION: synthetic

<400> SEQUENCE: 60
atgggggctc ccgttaatcc gaaga 25

<210> SEQ ID NO 61
<211> LENGTH: 25
<212> TYPE: DNA
<213> ORGANISM: Artificial
<220> FEATURE:
<223> OTHER INFORMATION: synthetic

<400> SEQUENCE: 61
agcgccggta gcgagcatac gtatg 25

<210> SEQ ID NO 62
<211> LENGTH: 25
<212> TYPE: DNA
<213> ORGANISM: Artificial
<220> FEATURE:
<223> OTHER INFORMATION: synthetic

<400> SEQUENCE: 62
acgactctgc ttattatact cggtc 25

<210> SEQ ID NO 63
<211> LENGTH: 25
<212> TYPE: DNA
<213> ORGANISM: Artificial
<220> FEATURE:
<223> OTHER INFORMATION: synthetic

<400> SEQUENCE: 63
gacatattag gggcgacgtc tccaa 25

<210> SEQ ID NO 64
<211> LENGTH: 644
<212> TYPE: DNA
<213> ORGANISM: Solanum lycopersicum

<400> SEQUENCE: 64
aagtggtttg gcatattccg acgaagatca gttcaacctg ataacagcga cgacaacgat 60
gacgacatca atccaatctc aaattccatt gaatgttatg catgtactca agttggcgtc 120
cctgttttcc actccaccag ttgcgatgga gctaaccaac cggagtggga agcttcagcc 180
ggttcttctc tagttccaat tcaaaaccgg acggattcaa aaaccggaaa atcccggtcc 240
agtcgcagcc ggcacacatc ggggccgttc gggcgtgtat tagaccctcg aagcaagcgc 300
gtgcagagat ggaaccgaat gattttattg gcacgtggca tggctttagc cgttgatcct 360
ctattctttt acgccttatc catcggccgc ggtggatcgc cgtgtttgta catggacggc 420
agcctggcgg ctatcgtcac cgtgattcgg actagcgtcg acgccgtgca cctcttccat 480
ttgtggttgc agtttcgttt ggcttacgtg tcgagagaat cgctggtggt tggttgtggg 540
aaactcgtgt gggatgcgcg tgcgattgct tctcactatg ttaggtccct taaaggattt 600
tggttcgatg cttttgtcat ccttcccgtt ccacaggctg tatt 644

<210> SEQ ID NO 65
<211> LENGTH: 652
<212> TYPE: DNA
<213> ORGANISM: Solanum lycopersicum

<400> SEQUENCE: 65
cgacgccgtg cacctcttcc atttgtggtt gcagtttcgt ttggcttacg tgtcgagaga 60
atcgctggtg gttggttgtg ggaaactcgt gtgggatgcg cgtgcgattg cttctcacta 120
tgttaggtcc cttaaaggat tttggttcga tgcttttgtc atccttcccg ttccacaggc 180
tgtattctgg ctggtggttc caaaactaat aagagaagag cagataaagc ttataatgac 240
gatcctttta ttaatgttct tgttccagtt ccttcccaaa gtttatcact gtataagctt 300
aatgagaagg atgcaaaagg ttacaggata tatttttggt accatctggt ggggatttgg 360
acttaatctc attgcttatt ttattgcttc tcatgttgct gggggatgct ggtatgttct 420

-continued tgcaatacaa agagtggctt catgtctaag gcagcagtgt gagcgcaacc cttcgtgtaa 480
tctatctttg tcttgctcag aggaggtgtg ttatcagttt ctgttgccaa caggaactgt 540
gggaaatcca tgtgctggga actcaacaac agtgaccagg aagccaatgt gtttggatgt 600
caatggacca tttccatatg ggatatacca atgggcactt cctgttgttt ct 652

<210> SEQ ID NO 66
<211> LENGTH: 656
<212> TYPE: DNA
<213> ORGANISM: Solanum lycopersicum

<400> SEQUENCE: 66
atctttgtct tgctcagagg aggtgtgtta tcagtttctg ttgccaacag gaactgtggg 60
aaatccatgt gctgggaact caacaacagt gaccaggaag ccaatgtgtt tggatgtcaa 120
tggaccattt ccatatggga tataccaatg ggcacttcct gttgtttcta gcagatccgt 180
cactgttaag attctttacc ccatcttttg gggattgatg acccttagca catttggcaa 240
tgacttagaa ccaacaagtc actggctgga agttattttc agtatatgcc ttgtgcttag 300
tggattgatg ctcttcactt tgctgattgg taacattcag gtgtttttac acgcggtcat 360
ggcaaagaag cgaaaaatgc aattaagatg tagggatatg gaatggtgga tgaggaggag 420
acaattacca tcacaattaa gacaaagagt tcgccacttt gaacaccaga gatgggctat 480
gatgggtggc gaagatgaga tggaacttgt aaaagacctg ccagaaggac tacgaaggga 540
catcaaacgc tttctttgcc ttgatcttat taagaaggtt cctctgttcg aaagtttgga 600
tgatctgatt ctagataaca tttgtgatcg cgttaagcca cttgtgttct ctaaag 656

<210> SEQ ID NO 67
<211> LENGTH: 651
<212> TYPE: DNA
<213> ORGANISM: Solanum lycopersicum

<400> SEQUENCE: 67
atggaacttg taaaagacct gccagaagga ctacgaaggg acatcaaacg ctttctttgc 60
cttgatctta ttaagaaggt tcctctgttc gaaagtttgg atgatctgat tctagataac 120
atttgtgatc gcgttaagcc acttgtgttc tctaaagatg agaagatcat aagagaagga 180
gatccagtgc acagggttgt gttcattgtt cgtggacgtg taaaaagtag ccaaaacctc 240
agtaaaggag tgattgccac aagcatactt gagcctggag gcttctttgg agatgaactt 300
ctttcctggt gcttacgccg tccctttatt gacagacttc cagcttcttc cgcaaccttc 360
acttgcattg aatctacaga agcatttggc ttagatgcaa accaccttcg atttatcacg 420
gatcacttca gatacaaatt tgcaaacgag aggctgaaga gaacagcaag gtattattca 480
tccaattgga gaacctgggc tgctgtgaat atacagttag cttggcgacg ttacatgatg 540
aggactagcc gtcccactat acatgtgatc gaaaatgggg ataatgatca tcgtcttcgc 600
aagtatgctg caatgttctt gtcaatcaga ccacatgatc atcttgaata g 651

<210> SEQ ID NO 68
<211> LENGTH: 649
<212> TYPE: DNA
<213> ORGANISM: Aqueoria victoria

<400> SEQUENCE: 68
ctggatggtg atgtgaacgg gcacaagttc tccgtcagcg gagagggtga aggtgatgcc 60

-continued

```
acctacggaa agctcaccct gaagttcatc tgcactaccg gaaagctccc tgttccgtgg    120

ccaaccctcg tcaccacttt cacctacggt gttcagtgct tctcccggta cccagatcac    180

atgaagcagc atgacttctt caagagcgcc atgcccgaag gctacgtgca agaaaggact    240

atctctttca aggatgacgg gaactacaag acacgtgccg aagtcaagtt cgaaggtgat    300

accctggtga accgcatcga gctgaaaggt atcgatttca aggaagatgg aaacatcctc    360

ggacacaagc tggagtacaa ctacaactcc cacaacgtat acatcacggc cgacaagcag    420

aagaacggca tcaaggctaa cttcaagatc aggcacaaca tcgaagatgg aagcgtgcaa    480

ctggcggacc actaccagca gaacacgccc atcggcgatg gccctgtcct gctgccggac    540

aaccattacc tgtccacgca atctgccctc tccaaggacc ccaacgagaa gagggaccac    600

atggtcctgc tggagttcgt gacggctgct gggatcacgc atggcatgg                649
```